United States Patent
Al-Ali et al.

(10) Patent No.: US 11,992,308 B2
(45) Date of Patent: May 28, 2024

(54) PATIENT MONITORING DEVICE WITH IMPROVED USER INTERFACE

(71) Applicant: MASIMO CORPORATION, Irvine, CA (US)

(72) Inventors: Ammar Al-Ali, San Juan Capistrano, CA (US); Faisal Kashif, Irvine, CA (US); Mohammad Usman, Mission Viejo, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 17/844,530

(22) Filed: Jun. 20, 2022

(65) Prior Publication Data

US 2023/0037434 A1 Feb. 9, 2023

Related U.S. Application Data

(63) Continuation of application No. 16/599,000, filed on Oct. 10, 2019, now Pat. No. 11,406,286.
(Continued)

(51) Int. Cl.
*A61B 5/11* (2006.01)
*A61B 5/00* (2006.01)

(52) U.S. Cl.
CPC .......... *A61B 5/1116* (2013.01); *A61B 5/0006* (2013.01); *A61B 5/0008* (2013.01);
(Continued)

(58) Field of Classification Search
None
See application file for complete search history.

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

CN 104127181 11/2014
CN 104586398 5/2015
(Continued)

OTHER PUBLICATIONS

US 2022/0192529 A1, 06/2022, Al-Ali et al. (withdrawn)
(Continued)

*Primary Examiner* — Benjamin S Melhus
(74) *Attorney, Agent, or Firm* — Knobbe, Martens, Olson & Bear, LLP

(57) ABSTRACT

A patient monitor for monitoring a patient's orientation to reduce a risk of the patient developing a pressure ulcer can include one or more hardware processors that can receive and process data from a sensor to determine the patient's orientation. The one or more hardware processors can maintain a plurality of timers associated with available orientations of the patient. Each of the plurality of timers can account for a non-consecutive duration said patient is in an associated available orientation. The non-consecutive duration can vary depending on whether a patient is in the available orientation. The patient monitor can include a structured display including an orientation trend and a patient representation illustrating a current orientation of the patient. The orientation trend can include a heat map that graphically illustrates said non-consecutive durations of the patient in the available orientations and/or an orientation graph that displays the patient' orientation history.

20 Claims, 27 Drawing Sheets

Related U.S. Application Data

(60) Provisional application No. 62/744,560, filed on Oct. 11, 2018.

(52) U.S. Cl.
CPC ......... *A61B 5/1115* (2013.01); *A61B 5/1121* (2013.01); *A61B 5/6823* (2013.01); *A61B 5/744* (2013.01); *A61B 2562/0219* (2013.01); *A61B 2562/0223* (2013.01)

(56) References Cited

U.S. PATENT DOCUMENTS

| | | | |
|---|---|---|---|
| 5,319,355 A | 6/1994 | Russek | |
| 5,337,744 A | 8/1994 | Branigan | |
| 5,341,805 A | 8/1994 | Stavridi et al. | |
| 5,355,880 A | 10/1994 | Thomas | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,590,649 A | 1/1997 | Caro et al. | |
| 5,602,924 A | 2/1997 | Durand et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| D384,341 S | 9/1997 | Hoffman et al. | |
| 5,671,914 A | 9/1997 | Kalkhoran et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,890,929 A | 4/1999 | Mills et al. | |
| 5,919,134 A | 7/1999 | Diab | |
| 5,938,690 A | 8/1999 | Law et al. | |
| 5,950,189 A | 9/1999 | Cohen et al. | |
| 5,987,343 A | 11/1999 | Kinast | |
| 5,997,343 A | 12/1999 | Mills et al. | |
| 6,002,952 A | 12/1999 | Diab et al. | |
| 6,010,937 A | 1/2000 | Karam et al. | |
| 6,027,452 A | 2/2000 | Flaherty et al. | |
| 6,040,578 A | 3/2000 | Malin et al. | |
| 6,066,204 A | 5/2000 | Haven | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,129,686 A | 10/2000 | Friedman | |
| 6,144,868 A | 11/2000 | Parker | |
| 6,152,754 A | 11/2000 | Gerhardt et al. | |
| 6,184,521 B1 | 2/2001 | Coffin, IV et al. | |
| 6,188,407 B1 | 2/2001 | Smith et al. | |
| D441,761 S | 5/2001 | Machida et al. | |
| 6,232,609 B1 | 5/2001 | Snyder et al. | |
| 6,241,683 B1 | 6/2001 | Macklem et al. | |
| 6,253,097 B1 | 6/2001 | Aronow et al. | |
| 6,255,708 B1 | 7/2001 | Sudharsanan et al. | |
| 6,280,381 B1 | 8/2001 | Malin et al. | |
| 6,285,896 B1 | 9/2001 | Tobler et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,334,065 B1 | 12/2001 | Al-Ali et al. | |
| 6,360,114 B1 | 3/2002 | Diab et al. | |
| 6,368,283 B1 | 4/2002 | Xu et al. | |
| 6,393,325 B1 | 5/2002 | Mann et al. | |
| 6,411,373 B1 | 6/2002 | Garside et al. | |
| 6,415,167 B1 | 7/2002 | Blank et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| D467,937 S | 12/2002 | Grundel et al. | |
| 6,505,059 B1 | 1/2003 | Kollias et al. | |
| 6,525,386 B1 | 2/2003 | Mills et al. | |
| 6,526,300 B1 | 2/2003 | Kiani et al. | |
| 6,534,012 B1 | 3/2003 | Hazen et al. | |
| 6,542,764 B1 | 4/2003 | Al-Ali et al. | |
| D474,197 S | 5/2003 | Nguyen | |
| 6,580,086 B1 | 6/2003 | Schulz et al. | |
| 6,584,336 B1 | 6/2003 | Ali et al. | |
| 6,587,196 B1 | 7/2003 | Stippick et al. | |
| 6,587,199 B1 | 7/2003 | Luu | |
| 6,595,316 B2 | 7/2003 | Cybulski et al. | |
| 6,597,932 B2 | 7/2003 | Tian et al. | |
| 6,606,511 B1 | 8/2003 | Ali et al. | |
| 6,635,559 B2 | 10/2003 | Greenwald et al. | |
| 6,639,668 B1 | 10/2003 | Trepagnier | |
| 6,640,116 B2 | 10/2003 | Diab | |
| 6,640,117 B2 | 10/2003 | Makarewicz et al. | |
| D482,040 S | 11/2003 | Itai et al. | |
| 6,658,276 B2 | 12/2003 | Kiani et al. | |
| 6,661,161 B1 | 12/2003 | Lanzo et al. | |
| 6,684,276 B2 | 1/2004 | Walker et al. | |
| 6,690,397 B1 | 2/2004 | Daignault, Jr. | |
| 6,697,656 B1 | 2/2004 | Al-Ali | |
| 6,697,658 B2 | 2/2004 | Al-Ali | |
| RE38,476 E | 3/2004 | Diab et al. | |
| RE38,492 E | 4/2004 | Diab et al. | |
| 6,738,652 B2 | 5/2004 | Mattu et al. | |
| 6,760,607 B2 | 7/2004 | Al-Ali | |
| 6,788,965 B2 | 9/2004 | Ruchti et al. | |
| 6,816,241 B2 | 11/2004 | Grubisic | |
| 6,822,564 B2 | 11/2004 | Al-Ali | |
| 6,850,787 B2 | 2/2005 | Weber et al. | |
| 6,850,788 B2 | 2/2005 | Al-Ali | |
| 6,876,931 B2 | 4/2005 | Lorenz et al. | |
| D505,135 S | 5/2005 | Sapp et al. | |
| 6,920,345 B2 | 7/2005 | Al-Ali et al. | |
| 6,934,570 B2 | 8/2005 | Kiani et al. | |
| 6,943,348 B1 | 9/2005 | Coffin, IV | |
| 6,956,649 B2 | 10/2005 | Acosta et al. | |
| 6,961,598 B2 | 11/2005 | Diab | |
| 6,970,792 B1 | 11/2005 | Diab | |
| 6,985,764 B2 | 1/2006 | Mason et al. | |
| 6,990,364 B2 | 1/2006 | Ruchti et al. | |
| 6,998,247 B2 | 2/2006 | Monfre et al. | |
| 7,003,338 B2 | 2/2006 | Weber et al. | |
| 7,015,451 B2 | 3/2006 | Dalke et al. | |
| 7,027,849 B2 | 4/2006 | Al-Ali | |
| D523,441 S | 6/2006 | Sapp et al. | |
| D526,719 S | 8/2006 | Richie, Jr. et al. | |
| 7,096,052 B2 | 8/2006 | Mason et al. | |
| 7,096,054 B2 | 8/2006 | Abdul-Hafiz et al. | |
| D529,038 S | 9/2006 | Sapp et al. | |
| D529,616 S | 10/2006 | Deros et al. | |
| 7,133,710 B2 | 11/2006 | Acosta et al. | |
| 7,142,901 B2 | 11/2006 | Kiani et al. | |
| 7,225,006 B2 | 5/2007 | Al-Ali et al. | |
| RE39,672 E | 6/2007 | Shehada et al. | |
| D544,496 S | 6/2007 | Evans et al. | |
| D549,713 S | 8/2007 | Lewin et al. | |
| D549,721 S | 8/2007 | Ito et al. | |
| 7,254,429 B2 | 8/2007 | Schurman et al. | |
| 7,254,431 B2 | 8/2007 | Al-Ali et al. | |
| 7,254,434 B2 | 8/2007 | Schulz et al. | |
| 7,274,955 B2 | 9/2007 | Kiani et al. | |
| D554,263 S | 10/2007 | Al-Ali et al. | |
| 7,280,858 B2 | 10/2007 | Al-Ali et al. | |

(56) References Cited

U.S. PATENT DOCUMENTS

| | | |
|---|---|---|
| 7,289,835 B2 | 10/2007 | Mansfield et al. |
| 7,292,883 B2 | 11/2007 | De Felice et al. |
| D561,193 S | 2/2008 | O'Mullan et al. |
| 7,341,559 B2 | 3/2008 | Schulz et al. |
| 7,343,186 B2 | 3/2008 | Lamego et al. |
| D566,282 S | 4/2008 | Al-Ali et al. |
| D566,722 S | 4/2008 | Jackson |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D586,355 S | 2/2009 | Mori et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D613,301 S | 4/2010 | Lee et al. |
| D614,305 S | 4/2010 | Al-Ali et al. |
| D614,634 S | 4/2010 | Nilsen |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| D619,609 S | 7/2010 | Meziere |
| 7,761,127 B2 | 7/2010 | Al-Ali et al. |
| 7,764,982 B2 | 7/2010 | Dalke et al. |
| D621,516 S | 8/2010 | Kiani et al. |
| D623,658 S | 9/2010 | Fitzmaurice et al. |
| 7,791,155 B2 | 9/2010 | Diab |
| D624,933 S | 10/2010 | Fitzmaurice et al. |
| D625,327 S | 10/2010 | Fitzmaurice et al. |
| D625,328 S | 10/2010 | Fitzmaurice et al. |
| D626,143 S | 10/2010 | Karten et al. |
| RE41,912 E | 11/2010 | Parker |
| D629,410 S | 12/2010 | Ray et al. |
| D630,645 S | 1/2011 | Tokunaga et al. |
| 7,880,626 B2 | 2/2011 | Al-Ali et al. |
| D634,332 S | 3/2011 | van der Spek |
| 7,909,772 B2 | 3/2011 | Popov et al. |
| D636,399 S | 4/2011 | Vance et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| D645,871 S | 9/2011 | Khan et al. |
| 8,028,701 B2 | 10/2011 | Al-Ali et al. |
| D648,346 S | 11/2011 | Anzures |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,130,219 B2 | 3/2012 | Fleury et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| D665,163 S | 8/2012 | Leifeld et al. |
| 8,255,026 B1 | 8/2012 | Al-Ali |
| D667,842 S | 9/2012 | Ouilhet |
| 8,265,723 B1 | 9/2012 | McHale et al. |
| 8,274,360 B2 | 9/2012 | Sampath et al. |
| 8,280,473 B2 | 10/2012 | Al-Ali |
| 8,314,789 B2 | 11/2012 | Fitzmaurice et al. |
| 8,315,683 B2 | 11/2012 | Al-Ali et al. |
| RE43,860 E | 12/2012 | Parker |
| 8,323,218 B2 | 12/2012 | Davis et al. |
| D673,964 S | 1/2013 | Cojuangco et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| D681,651 S | 5/2013 | Fletcher et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| D687,063 S | 7/2013 | Myung et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,017 S | 10/2013 | Andersson et al. |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,572,509 B2 | 10/2013 | Gobeil |
| D693,365 S | 11/2013 | Gardner et al. |
| 8,577,431 B2 | 11/2013 | Lamego et al. |
| 8,577,433 B2 | 11/2013 | McKenna |
| 8,579,834 B2 | 11/2013 | Davis et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| D699,248 S | 2/2014 | Pearson et al. |
| 8,641,631 B2 | 2/2014 | Sierra et al. |
| 8,652,060 B2 | 2/2014 | Al-Ali |
| D701,521 S | 3/2014 | Kim et al. |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,761,851 B2 | 6/2014 | Benni et al. |
| D709,905 S | 7/2014 | Bohmfalk et al. |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |

(56) References Cited

U.S. PATENT DOCUMENTS

| | | |
|---|---|---|
| D714,336 S | 9/2014 | Cojuangco et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| D716,316 S | 10/2014 | Behzadi et al. |
| D716,318 S | 10/2014 | Fan et al. |
| D716,325 S | 10/2014 | Brudnicki |
| 8,852,094 B2 | 10/2014 | Al-Ali et al. |
| 8,852,994 B2 | 10/2014 | Wojtczuk et al. |
| D716,829 S | 11/2014 | Sik |
| 8,897,847 B2 | 11/2014 | Al-Ali |
| D719,175 S | 12/2014 | Nguyen |
| 8,911,377 B2 | 12/2014 | Al-Ali |
| 8,932,217 B2 | 1/2015 | Gibson et al. |
| D722,079 S | 2/2015 | Charlès et al. |
| D724,618 S | 3/2015 | Shin |
| 8,989,831 B2 | 3/2015 | Al-Ali et al. |
| 8,998,809 B2 | 4/2015 | Kiani |
| D728,601 S | 5/2015 | Angelides |
| D732,050 S | 6/2015 | Lee et al. |
| D733,172 S | 6/2015 | Angelides |
| 9,066,666 B2 | 6/2015 | Kiani |
| 9,066,680 B1 | 6/2015 | Al-Ali et al. |
| D735,229 S | 7/2015 | Lim |
| D735,733 S | 8/2015 | Hontz, Jr. |
| D736,808 S | 8/2015 | Soegiono et al. |
| 9,095,316 B2 | 8/2015 | Welch et al. |
| 9,106,038 B2 | 8/2015 | Telfort et al. |
| 9,107,625 B2 | 8/2015 | Telfort et al. |
| D738,383 S | 9/2015 | Lim et al. |
| D738,928 S | 9/2015 | Mahaffey |
| D738,929 S | 9/2015 | Mahaffey |
| D739,422 S | 9/2015 | Jeong et al. |
| 9,131,881 B2 | 9/2015 | Diab et al. |
| 9,138,180 B1 | 9/2015 | Coverston et al. |
| 9,153,112 B1 | 10/2015 | Kiani et al. |
| D742,896 S | 11/2015 | Comfort et al. |
| D742,907 S | 11/2015 | Lee et al. |
| D743,982 S | 11/2015 | Lee et al. |
| 9,180,302 B2 | 11/2015 | Drees et al. |
| 9,192,329 B2 | 11/2015 | Al-Ali |
| 9,192,330 B2 | 11/2015 | Lin et al. |
| 9,192,351 B1 | 11/2015 | Telfort et al. |
| 9,195,385 B2 | 11/2015 | Al-Ali et al. |
| D745,046 S | 12/2015 | Shin et al. |
| D746,314 S | 12/2015 | Jung et al. |
| 9,211,095 B1 | 12/2015 | Al-Ali |
| 9,211,096 B2 | 12/2015 | Tremper et al. |
| 9,218,454 B2 | 12/2015 | Kiani et al. |
| D747,731 S | 1/2016 | Oliveira |
| 9,245,668 B1 | 1/2016 | Vo et al. |
| 9,267,572 B2 | 2/2016 | Barker et al. |
| D750,642 S | 3/2016 | Lee |
| D751,574 S | 3/2016 | Forsblom |
| D752,076 S | 3/2016 | Guesnon, Jr. |
| D752,622 S | 3/2016 | Cojuangco et al. |
| D752,646 S | 3/2016 | Miles et al. |
| 9,277,880 B2 | 3/2016 | Poeze et al. |
| D753,173 S | 4/2016 | Cojuangco et al. |
| D753,669 S | 4/2016 | Chen |
| D753,716 S | 4/2016 | Torres et al. |
| D754,179 S | 4/2016 | Angelides |
| D754,705 S | 4/2016 | Angelides |
| 9,304,659 B2 | 4/2016 | Sherrard et al. |
| 9,307,928 B1 | 4/2016 | Al-Ali et al. |
| 9,323,894 B2 | 4/2016 | Kiani |
| D755,392 S | 5/2016 | Hwang et al. |
| D756,372 S | 5/2016 | Bertnick et al. |
| 9,326,712 B1 | 5/2016 | Kiani |
| D760,158 S | 6/2016 | Vandaele et al. |
| D760,790 S | 7/2016 | Ishii et al. |
| 9,392,945 B2 | 7/2016 | Al-Ali et al. |
| D762,665 S | 8/2016 | Lee et al. |
| D763,317 S | 8/2016 | Kim et al. |
| 9,408,542 B1 | 8/2016 | Kinast et al. |
| D766,302 S | 9/2016 | Phelan et al. |
| D767,605 S | 9/2016 | Mensinger et al. |
| 9,436,645 B2 | 9/2016 | Al-Ali et al. |
| 9,445,759 B1 | 9/2016 | Lamego et al. |
| D768,652 S | 10/2016 | Yang |
| D768,673 S | 10/2016 | Kim et al. |
| D769,278 S | 10/2016 | Ukrainsky et al. |
| 9,474,474 B2 | 10/2016 | Lamego et al. |
| D772,905 S | 11/2016 | Ingenlath |
| D772,931 S | 11/2016 | Vulk et al. |
| 9,480,401 B2 | 11/2016 | Koehler et al. |
| 9,480,435 B2 | 11/2016 | Olsen |
| 9,510,779 B2 | 12/2016 | Poeze et al. |
| 9,517,024 B2 | 12/2016 | Kiani et al. |
| D775,663 S | 1/2017 | Akana et al. |
| D777,191 S | 1/2017 | Polimeni |
| 9,532,722 B2 | 1/2017 | Lamego et al. |
| 9,560,996 B2 | 2/2017 | Kiani |
| 9,579,039 B2 | 2/2017 | Jansen et al. |
| D781,876 S | 3/2017 | Wang |
| D783,032 S | 4/2017 | Cashner et al. |
| D783,652 S | 4/2017 | Guan et al. |
| D784,390 S | 4/2017 | Dye et al. |
| 9,622,692 B2 | 4/2017 | Lamego et al. |
| D785,656 S | 5/2017 | Bramer et al. |
| D785,658 S | 5/2017 | Moroney et al. |
| D786,279 S | 5/2017 | McKim et al. |
| D786,301 S | 5/2017 | Napper et al. |
| D788,312 S | 5/2017 | Al-Ali et al. |
| 9,649,054 B2 | 5/2017 | Lamego et al. |
| D789,404 S | 6/2017 | Modestine et al. |
| D789,963 S | 6/2017 | Agashiwala et al. |
| D790,577 S | 6/2017 | Hatzikosta et al. |
| D790,597 S | 6/2017 | Kayimoglu et al. |
| D791,817 S | 7/2017 | Sun |
| 9,697,928 B2 | 7/2017 | Al-Ali et al. |
| D793,427 S | 8/2017 | Sun |
| D794,075 S | 8/2017 | Park et al. |
| D795,899 S | 8/2017 | Carrigan et al. |
| D795,902 S | 8/2017 | Ahmad et al. |
| D795,903 S | 8/2017 | Chen et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| D796,526 S | 9/2017 | Kim et al. |
| D797,118 S | 9/2017 | Van Every et al. |
| D797,119 S | 9/2017 | Kim et al. |
| D797,769 S | 9/2017 | Li |
| D798,320 S | 9/2017 | Gouvernel et al. |
| D798,331 S | 9/2017 | Fong et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| D803,247 S | 11/2017 | Mistry et al. |
| 9,808,188 B1 | 11/2017 | Perea et al. |
| 9,830,424 B2 | 11/2017 | Dixon |
| D804,499 S | 12/2017 | Eklund et al. |
| D805,102 S | 12/2017 | Stamatiou |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| D807,918 S | 1/2018 | Cohen et al. |
| D807,919 S | 1/2018 | Cohen et al. |
| D808,404 S | 1/2018 | Agashiwala et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| D809,544 S | 2/2018 | Ambielli |
| 9,891,079 B2 | 2/2018 | Dalvi |
| 9,898,651 B2 | 2/2018 | Gurman et al. |
| D812,640 S | 3/2018 | Spector et al. |
| 9,924,897 B1 | 3/2018 | Abdul-Hafiz |

(56) References Cited

U.S. PATENT DOCUMENTS

| | | |
|---|---|---|
| D815,131 S | 4/2018 | Thompson et al. |
| D815,135 S | 4/2018 | Spector |
| D815,660 S | 4/2018 | Spector |
| 9,936,917 B2 | 4/2018 | Poeze et al. |
| D816,695 S | 5/2018 | Spector |
| 9,955,937 B2 | 5/2018 | Telfort |
| 9,962,081 B2 | 5/2018 | Mensinger et al. |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| D822,684 S | 7/2018 | Clausen-Stuck et al. |
| 10,010,276 B2 | 7/2018 | Al-Ali et al. |
| 10,020,075 B2 | 7/2018 | Perlman et al. |
| 10,061,896 B2 | 8/2018 | Jordan et al. |
| D829,236 S | 9/2018 | Chauhan et al. |
| 10,086,138 B1 | 10/2018 | Novak, Jr. |
| 10,111,591 B2 | 10/2018 | Dyell et al. |
| D833,624 S | 11/2018 | DeJong et al. |
| D834,601 S | 11/2018 | Felt |
| 10,123,729 B2 | 11/2018 | Dyell et al. |
| 10,140,837 B2 | 11/2018 | Shen et al. |
| D835,145 S | 12/2018 | Cashner et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| D835,312 S | 12/2018 | Yang |
| D835,648 S | 12/2018 | Begin et al. |
| D836,123 S | 12/2018 | Poillalamarri et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| D837,815 S | 1/2019 | Biberger et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| D841,669 S | 2/2019 | Hansen et al. |
| 10,205,291 B2 | 2/2019 | Scruggs et al. |
| D843,401 S | 3/2019 | Spector |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| D848,482 S | 5/2019 | Lee et al. |
| 10,279,247 B2 | 5/2019 | Kiani |
| 10,292,664 B2 | 5/2019 | Al-Ali |
| 10,299,720 B2 | 5/2019 | Brown et al. |
| 10,310,616 B2 | 6/2019 | Rose et al. |
| 10,327,337 B2 | 6/2019 | Schmidt et al. |
| 10,327,697 B1 | 6/2019 | Stein et al. |
| 10,327,713 B2 | 6/2019 | Barker et al. |
| 10,332,630 B2 | 6/2019 | Al-Ali |
| D855,064 S | 7/2019 | Lei |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,391,008 B2 | 8/2019 | Zerhusen et al. |
| D859,460 S | 9/2019 | Kaminer et al. |
| D859,461 S | 9/2019 | Madison et al. |
| D861,013 S | 9/2019 | Chang |
| 10,402,650 B1 | 9/2019 | Suiter et al. |
| D864,120 S | 10/2019 | Forrest et al. |
| D864,229 S | 10/2019 | Frakulic et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| D865,804 S | 11/2019 | Warner et al. |
| D867,384 S | 11/2019 | Siccardi et al. |
| 10,463,340 B2 | 11/2019 | Telfort et al. |
| 10,471,159 B1 | 11/2019 | Lapotko et al. |
| D869,495 S | 12/2019 | Pillalamarri et al. |
| D870,751 S | 12/2019 | Peeters et al. |
| D870,773 S | 12/2019 | Marrufo |
| 10,505,311 B2 | 12/2019 | Al-Ali et al. |
| D872,737 S | 1/2020 | Ressel et al. |
| D873,290 S | 1/2020 | Burnett et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| D879,110 S | 3/2020 | Matsushita |
| 10,588,565 B2 | 3/2020 | Larson et al. |
| 10,600,204 B1 | 3/2020 | Rush et al. |
| 10,608,817 B2 | 3/2020 | Haider et al. |
| D880,477 S | 4/2020 | Forrest et al. |
| D880,498 S | 4/2020 | Shahidi et al. |
| 10,617,302 B2 | 4/2020 | Al-Ali et al. |
| 10,617,335 B2 | 4/2020 | Al-Ali et al. |
| 10,631,732 B2 | 4/2020 | Larson et al. |
| 10,637,181 B2 | 4/2020 | Al-Ali et al. |
| D886,849 S | 6/2020 | Muhsin et al. |
| D887,426 S | 6/2020 | Matsushita |
| D887,548 S | 6/2020 | Abdul-Hafiz et al. |
| D887,549 S | 6/2020 | Abdul-Hafiz et al. |
| D888,732 S | 6/2020 | Momchilov et al. |
| 10,667,764 B2 | 6/2020 | Ahmed et al. |
| D889,496 S | 7/2020 | Giannino et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| D914,717 S | 3/2021 | Mensinger et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D916,803 S | 4/2021 | Birolo et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D918,932 S | 5/2021 | Gkanatsios et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| D921,654 S | 6/2021 | Burnett et al. |
| D922,423 S | 6/2021 | Frueh et al. |
| D922,425 S | 6/2021 | Frueh et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| D928,188 S | 8/2021 | Giannino et al. |
| D928,189 S | 8/2021 | Giannino et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |

(56) References Cited

U.S. PATENT DOCUMENTS

| | | |
|---|---|---|
| D938,979 S | 12/2021 | Miyai et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| D948,549 S | 4/2022 | Zheng et al. |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| D958,161 S | 7/2022 | Gkanatsios et al. |
| 11,382,567 B2 | 7/2022 | O'Brien et al. |
| 11,389,093 B2 | 7/2022 | Triman et al. |
| D959,450 S | 8/2022 | Nahavandi et al. |
| 11,406,286 B2 | 8/2022 | Al-Ali et al. |
| 11,417,426 B2 | 8/2022 | Muhsin et al. |
| D962,979 S | 9/2022 | Kim et al. |
| 11,439,329 B2 | 9/2022 | Lamego |
| 11,445,948 B2 | 9/2022 | Scruggs et al. |
| D965,789 S | 10/2022 | Al-Ali et al. |
| D967,152 S | 10/2022 | Lu et al. |
| D967,153 S | 10/2022 | Mazz et al. |
| D967,174 S | 10/2022 | Kodama |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D975,112 S | 1/2023 | Vojan et al. |
| D975,739 S | 1/2023 | Elgena et al. |
| D976,956 S | 1/2023 | Katz et al. |
| D976,960 S | 1/2023 | Chase et al. |
| D979,516 S | 2/2023 | Al-Ali et al. |
| D980,091 S | 3/2023 | Forrest et al. |
| D980,263 S | 3/2023 | Koch et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0063522 A1 | 4/2003 | Sagar |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0210402 A1 | 9/2005 | Gunn et al. |
| 2005/0234317 A1 | 10/2005 | Kiani |
| 2006/0073719 A1 | 4/2006 | Kiani |
| 2006/0074321 A1 | 4/2006 | Kouchi |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0054743 A1 | 2/2009 | Stewart |
| 2009/0055735 A1 | 2/2009 | Zaleski et al. |
| 2009/0093687 A1 | 4/2009 | Telfort et al. |
| 2009/0095926 A1 | 4/2009 | MacNeish, III |
| 2009/0149743 A1 | 6/2009 | Barron et al. |
| 2009/0167706 A1 | 7/2009 | Tan et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0010385 A1 | 1/2010 | Skelton et al. |
| 2010/0010584 A1 | 1/2010 | Skelton et al. |
| 2010/0030040 A1 | 2/2010 | Poeze et al. |
| 2010/0099064 A1 | 4/2010 | O'Reilly et al. |
| 2010/0234718 A1 | 9/2010 | Sampath et al. |
| 2010/0270257 A1 | 10/2010 | Wachman et al. |
| 2010/0277571 A1 | 11/2010 | Xu et al. |
| 2010/0298660 A1 | 11/2010 | McCombie et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0046498 A1 | 2/2011 | Klap et al. |
| 2011/0071420 A1 | 3/2011 | St. Pierre et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0208076 A1 | 8/2011 | Fong et al. |
| 2011/0230733 A1 | 9/2011 | Al-Ali |
| 2011/0263950 A1 | 10/2011 | Larson et al. |
| 2012/0026308 A1 | 2/2012 | Johnson et al. |
| 2012/0089419 A1 | 4/2012 | Huster et al. |
| 2012/0123231 A1 | 5/2012 | O'Reilly |
| 2012/0159372 A1 | 6/2012 | Stallings et al. |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0232520 A1 | 9/2012 | Sloan et al. |
| 2012/0283524 A1 | 11/2012 | Kiani et al. |
| 2012/0323501 A1 | 12/2012 | Sarrafzadeh et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0117696 A1 | 5/2013 | Robertson et al. |
| 2013/0222565 A1 | 8/2013 | Guerin et al. |
| 2013/0249695 A1 | 9/2013 | Hann |
| 2013/0267861 A1 | 10/2013 | Vassallo et al. |
| 2013/0283530 A1 | 10/2013 | Main et al. |
| 2013/0296672 A1 | 11/2013 | O'Neil et al. |
| 2013/0317393 A1 | 11/2013 | Weiss et al. |
| 2013/0345921 A1 | 12/2013 | Al-Ali et al. |
| 2014/0005502 A1 | 1/2014 | Klap et al. |
| 2014/0022256 A1 | 1/2014 | Carnes et al. |
| 2014/0039351 A1 | 2/2014 | Mix et al. |
| 2014/0098933 A1 | 4/2014 | Profio et al. |
| 2014/0129178 A1 | 5/2014 | Meduna et al. |
| 2014/0155755 A1 | 6/2014 | Pinter et al. |

(56) References Cited

U.S. PATENT DOCUMENTS

| | | |
|---|---|---|
| 2014/0157911 A1 | 6/2014 | Sarrafzadeh et al. |
| 2014/0166076 A1 | 6/2014 | Kiani et al. |
| 2014/0180160 A1 | 6/2014 | Brown et al. |
| 2014/0184422 A1 | 7/2014 | Mensinger et al. |
| 2014/0187973 A1 | 7/2014 | Brown et al. |
| 2014/0270082 A1 | 9/2014 | Moellmer et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0320391 A1 | 10/2014 | Bazaz |
| 2014/0323897 A1 | 10/2014 | Brown et al. |
| 2014/0323898 A1 | 10/2014 | Purdon et al. |
| 2014/0343628 A1 | 11/2014 | Kaula et al. |
| 2014/0344740 A1 | 11/2014 | Kaula et al. |
| 2014/0348417 A1 | 11/2014 | Moore et al. |
| 2014/0368499 A1 | 12/2014 | Kaur |
| 2015/0005600 A1 | 1/2015 | Blank et al. |
| 2015/0011907 A1 | 1/2015 | Purdon et al. |
| 2015/0045630 A1 | 2/2015 | Poliakine-Baruchi et al. |
| 2015/0051462 A1 | 2/2015 | Olsen |
| 2015/0073241 A1 | 3/2015 | Lamego |
| 2015/0080754 A1 | 3/2015 | Purdon et al. |
| 2015/0094618 A1 | 4/2015 | Russell et al. |
| 2015/0099950 A1 | 4/2015 | Al-Ali et al. |
| 2015/0106121 A1 | 4/2015 | Muhsin et al. |
| 2015/0135108 A1 | 5/2015 | Pope et al. |
| 2015/0164417 A1 | 6/2015 | Tupin, Jr. |
| 2015/0205509 A1 | 7/2015 | Scriven et al. |
| 2015/0301796 A1 | 10/2015 | Visser et al. |
| 2015/0320339 A1 | 11/2015 | Larson et al. |
| 2015/0320365 A1 | 11/2015 | Schulze et al. |
| 2016/0019352 A1 | 1/2016 | Cohen et al. |
| 2016/0073935 A1 | 3/2016 | van Beest |
| 2016/0081594 A1 | 3/2016 | Gaddipati et al. |
| 2016/0162131 A1 | 6/2016 | Zamor et al. |
| 2016/0196388 A1 | 7/2016 | Lamego |
| 2016/0199240 A1 | 7/2016 | Newkirk et al. |
| 2016/0206277 A1 | 7/2016 | Bidichandani et al. |
| 2016/0220181 A1 | 8/2016 | Rigoard et al. |
| 2016/0228050 A1 | 8/2016 | Sugla et al. |
| 2016/0278652 A1 | 9/2016 | Kaib et al. |
| 2016/0283665 A1 | 9/2016 | Sampath et al. |
| 2016/0296159 A1 | 10/2016 | Larson et al. |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0143281 A1 | 5/2017 | Olsen |
| 2017/0173632 A1 | 6/2017 | Al-Ali |
| 2017/0251974 A1 | 9/2017 | Shreim et al. |
| 2017/0270260 A1 | 9/2017 | Shetty et al. |
| 2017/0311891 A1 | 11/2017 | Kiani et al. |
| 2017/0325683 A1 | 11/2017 | Larson et al. |
| 2017/0357765 A1 | 12/2017 | Fauss et al. |
| 2018/0064595 A1 | 3/2018 | Srinivasan |
| 2018/0103874 A1 | 4/2018 | Lee et al. |
| 2018/0125412 A1 | 5/2018 | Ferber |
| 2018/0125433 A1 | 5/2018 | Ferber |
| 2018/0129357 A9 | 5/2018 | Imes et al. |
| 2018/0146917 A1 | 5/2018 | Iida et al. |
| 2018/0184984 A1 | 7/2018 | Zerhusen et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0277255 A1 | 9/2018 | Martin et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0315247 A1 | 11/2018 | Van Andel |
| 2018/0317826 A1 | 11/2018 | Muhsin et al. |
| 2018/0349008 A1 | 12/2018 | Manzari et al. |
| 2018/0350451 A1 | 12/2018 | Ohnemus et al. |
| 2018/0374577 A1 | 12/2018 | Bhimavarapu |
| 2019/0015023 A1 | 1/2019 | Monfre |
| 2019/0117070 A1 | 4/2019 | Muhsin et al. |
| 2019/0117124 A1 | 4/2019 | Hsu et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0012423 A1 | 1/2020 | Cinek et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0126284 A1 | 4/2020 | Garofalo et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0219167 A1 | 7/2020 | Jikomes et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0058843 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |

(56) References Cited

U.S. PATENT DOCUMENTS

| | | |
|---|---|---|
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |

FOREIGN PATENT DOCUMENTS

| | | |
|---|---|---|
| EP | 2 375 978 | 8/2013 |
| JP | 1622485 S | 1/2019 |
| KR | 10-2015-0084586 | 7/2015 |
| WO | WO 2010/125096 | 11/2010 |

OTHER PUBLICATIONS

Baxter, Nancy, "Will a New Pillow Help My Neck Pain?" Sep. 30, 2017, Lakeview Physiotherapy, site visited Oct. 21, 2020, 2 pages, https://lakeviewphysio.ca/blog/will-a-new-pi11ow-help-my-neck-pain.

"Clip Studio Paint useful features: 3D drawing figures" Apr. 8, 2018, YouTube, site visited Oct. 21, 2020, 1 page, https://www.youtube.com/watch?v=RuWpou1XTK4.

"Create a Speedometer like Semi Circle", Nov. 14, 2016, Stack Overflow, as visited Feb. 16, 2021, 1 page, https://stackoverflow.com/questions/40586460/create-a-speedometer-like-semi-circle.

IconBros, https://www.iconbros.com/icons/ib-mi-f-map, retrieved Nov. 3, 2020, Medical Item Collection, Map Icon Image, 1 page.

IPhoneNess, "6 Best Heart Monitor Apps for iPhone", posted by Ci Dec. 12, 2012. Archived Jan. 29, 2019 to https://web.archive.org/web/20130129233623/https://www.iphoneness.com/iphone-apps/best-heart-monitor-apps-for-iphone/.

"Know yourself and others by sleeping positions" Aug. 19, 2015, Blogspot, site visited Oct. 21, 2020, 1 page, http://anurawla.blogspot.com/2015/08/happyclub.html.

Niolay, Kurkin, "Man is Lying on the Floor . . . ", Nov. 28, 2016, Alamy, site visited Oct. 21, 2020, 1 page, https://www.alamy.com/man-is-lying-on-the-floor-time-to-relax-man-relaxing-and-dreaming-3d-human-body-model-vector-illustration-image239976040.html.

Pannurat et al., "Automatic Fall Monitoring: A Review", Sensors, 2014, vol. 14, pp. 12900-12936.

"Pressure Injury in the ICU: Major Reconstructive Surgery Required" Sep. 2017, ResearchGate, site visited Oct. 21, 2020, 1 page, https://www.researchgate.net/figure/30-40-side-lying-position_fig15_319897168.

"Unity 5 UI Custom Radial Slider Circular Slider", Uploaded by Andrei Bylov Jun. 29, 2016, 1 page, https://www.youtube.com/watch?v=rcfQG1I8Qq0.

Patient Monitoring Device With Improved User Interface, U.S. Appl. No. 17/938,435, filed Oct. 6, 2022.

Display Screen or Portion Thereof With Graphical User Interface, U.S. Appl. No. 29/666,325, U.S. Pat. No. D916,135, filed Oct. 11, 2018, Apr. 13, 2021.

Display Screen or Portion Thereof With Graphical User, U.S. Appl. No. 29/773,988, filed Mar. 12, 2021.

Display Screen or Portion Thereof With Graphical User Interface, U.S. Appl. No. 29/778,924, filed Apr. 15, 2021.

Display Screen or Portion Thereof With Graphical User Interface, U.S. Appl. No. 29/824,367, filed Jan. 24, 2022.

Display Screen or Portion Thereof With Graphical User Interface, U.S. Appl. No. 29/666,332, U.S. Pat. No. D917,550, filed Oct. 11, 2018, Apr. 27, 2021.

Display Screen or Portion Thereof With Graphical User Interface, U.S. Appl. No. 29/774,878, filed Mar. 19, 2021.

Display Screen or Portion Thereof With Graphical User Interface, U.S. Appl. No. 29/824,366, filed Jan. 24, 2022.

Display Screen or Portion Thereof With Graphical User Interface, U.S. Appl. No. 26/666,340, filed Oct. 11, 2018.

Display Screen or Portion Thereof With Graphical User Interface, U.S. Appl. No. 29/774,884, filed Mar. 19, 2021.

"9+ Free Body Diagram—Free Printable Download" Feb. 2016, template.net, http://www.template.net/design-templates/print/free-body-diagram/, 1 page.

Davoudi et al., "Intelligent ICU for Autonomous Patient Monitoring Using Pervasive Sensing and Deep Learning", Scientific Reports, vol. 9, May 2019, pp. 13.

"EPM 4600 Power Meter", Feb. 29, 2016, General Electric, https://web.archive.org/web/20160229194607/https://www.gegridsolutions.com/multilin/catalog/epm4600.htm#https://www.gegridsolutions.com/multilin/catalog/#4, 1 page.

"How CT Scan Machine Works", Dec. 27, 2012, YouTube, https://youtu.be/tqGmqRrxajQ, 1 page.

"How to Measure Sound in Android Phone for Free (Sound Meter)", Jan. 28, 2016, YouTube, https://www.youtube.com/watch?v=slgDJunUhNk, 1 page.

Leichman, Abigail, "Worlds First Bedsore Monitoring System", Jan. 6, 2014, https://www.israel21c.org/worlds-first-bedsore-monitoring-system/, pp. 5.

Letter from Todd Courtney to Masimo Corporation re 510(k) No. K191882, U.S. Food & Drug Administration, dated Apr. 22, 2020 in 16 pages.

"Male body masculine", Nov. 25, 2016, pixabay, https://pixabay.com/illustrations/male-body-masculine-human-figure-1859518/, 1 page.

"Medical Scans Explained", Nov. 2019, NIH News in Health, https://newsinhealth.nih.gov/2019/11/medical-scans-explained, 1 page.

"Multimeter", TiePie.com, https://web.archive.org/web/20220119045205/https://www.tiepie.com/en/oscilloscope-software/multimeter, Jan. 19, 2022, pp. 2.

NCS Company, "Showmotion: How Can I Not Like It !? ", https://www.youtube.com/watch?v=xEAmM4qOfqs, posted to youtube.com Nov. 5, 2020, 3 pages.

Schuller, Orfenn, "Studying the Human Figure: Part IV", Aug. 12, 2015, Behance, https://www.behance.net/gallery/16510861/Studying-The-Human-Figure-Part-IV, 1 page.

Sheth, Sarang, "This Sensor-Equipped Resistance Band Gives You a Fully Personalized Gym Workout . . . at Home", Yanko Design, https://www.yankodesign.com/2020/03/14/this-sensor-equipped-resistance-band-gives-you-a-fully-personalized-gym-workout-at-home/, Mar. 14, 2020, pp. 20.

Tscholl et al., "Situation Awareness-Oriented Patient Monitoring with Visual Patient Technology: A Qualitative Review of the Primary Research", Sensors, Apr. 9, 2020, pp. 23.

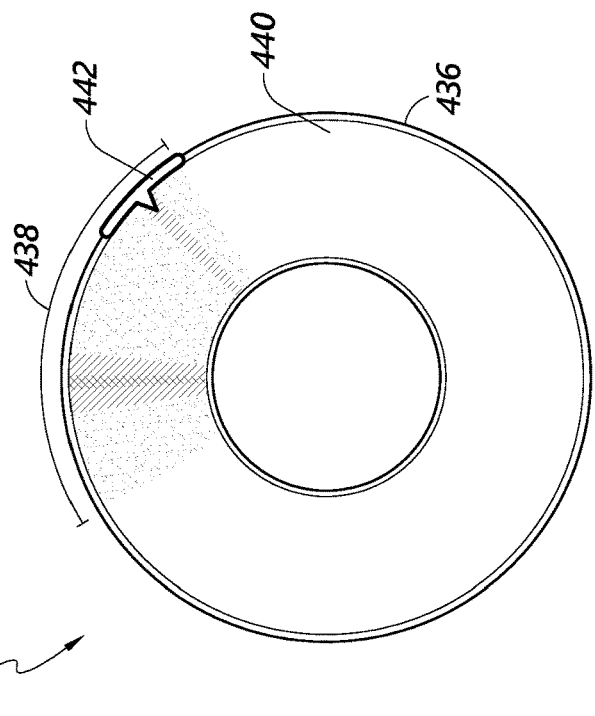
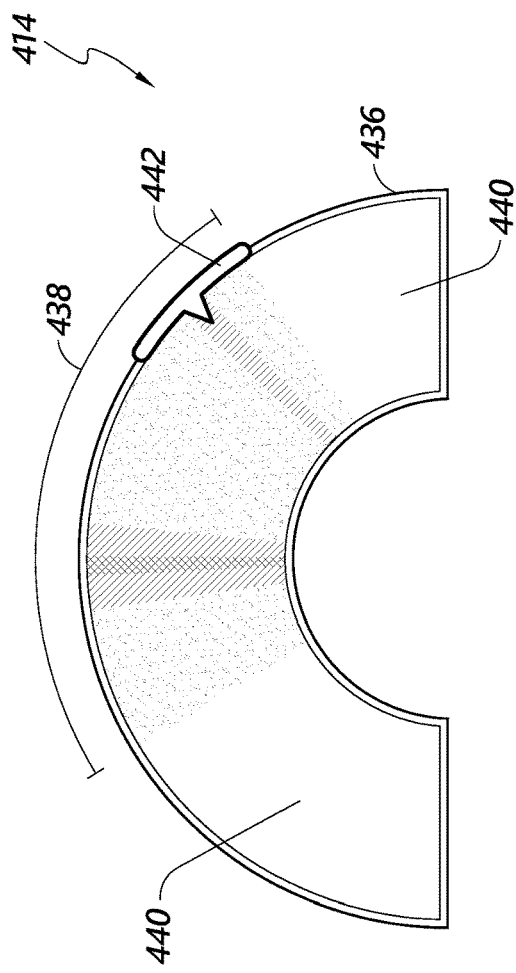
FIG. 8A
FIG. 8B

PATIENT MONITORING DEVICE WITH IMPROVED USER INTERFACE

INCORPORATION BY REFERENCE TO ANY PRIORITY APPLICATIONS

This application is a continuation of U.S. patent application Ser. No. 16/599,000, filed Oct. 10, 2019, which claims the benefit of priority under 35 U.S.C. § 119(e) from U.S. Provisional Application No. 62/744,560, filed Oct. 11, 2018. Each of the aforementioned applications is incorporated by reference herein in its entirety.

FIELD

The present disclosure relates to the field of patient monitoring. More specifically, the disclosure describes, among other things, devices, systems, and methods for monitoring and/or displaying information regarding a patient's position, orientation, and/or movement in a medical environment, and an improved graphical user interface.

BACKGROUND

In clinical settings, such as hospitals, nursing homes, convalescent homes, skilled nursing facilities, post-surgical recovery centers, and the like, patients are frequently confined to a bed for extended periods of time. Sometimes the patients are unconscious or sedated to such an extent that they have limited ability to change or control their position and/or orientation in the bed. Such patients can be at risk of forming pressure ulcers, which pose a serious risk to the patient's health and well-being. Pressure ulcers, which may also be referred to as "bed sores," "pressure sores," and "decubitus ulcers," involve injury to a patient's skin, and often the underlying tissue, which results from prolonged pressure forces applied to a site on the patient's body. Frequently, pressure ulcers develop on skin that covers bony areas of the body which have less muscle and/or fat tissue below the surface to distribute pressure applied thereto. Pressure ulcers can develop when such skin is subjected to prolonged contact with a surface of a bed or chair. Examples of such body locations include the back or side of the head, shoulders, shoulder blades, elbows, spine, hips, lower back, tailbone, heels, ankles, and skin behind the knees.

Pressure ulcers are caused by application of pressure at an anatomical site that occludes blood flow to the skin and other tissue near the location. Sustained pressure between a structural surface (such as a bed) and a particular point on the patient's body can restrict blood flow when the applied pressure is greater than the blood pressure flowing through the capillaries that deliver oxygen and other nutrients to the skin and other tissue. Deprived of oxygen and nutrients, the skin cells can become damaged, leading to tissue necrosis in as few as 2 to 6 hours. While hospital-acquired pressure ulcers commonly occur in elderly and mobility-impaired populations, such ulcers are considered to be preventable and have been termed "never events." In some cases, medical insurance carriers have imposed restrictions on the amount they will reimburse a hospital for pressure ulcer treatment, and state and federal legislation now requires hospitals to report the occurrence of pressure ulcers in their facilities.

Risk factors for pressure ulcers can be categorized as modifiable and non-modifiable. Modifiable risk factors include actions that healthcare providers can take, while non-modifiable risk factors include aspects of patient health and behavior. It is valuable to document such non-modifiable risk factors so that caregivers can identify and attend to patients at risk of developing pressure ulcers. It is recommended that caregivers develop a documented risk assessment policy to predict the risk of a patient developing a pressure ulcer. Such an assessment can encompass all aspects of a patient's health and environment, and may employ commonly used measures in the field, such as the Braden and Norton scales. Such risk assessment tools may be used to direct preventative strategies not only when a patient is at rest in his or her bed, but also when undergoing surgery.

Additional factors that can contribute to the formation of pressure ulcers include friction and shear forces. Friction can occur when skin is dragged across a surface which can happen when patients are moved, especially when the skin is moist. Such frictional forces can damage the skin and make it more vulnerable to injury, including formation of a pressure ulcer. Shear forces occur when two forces move in opposite directions. For example, when the head portion of a bed is elevated at an incline, the patient's spine, tailbone, and hip regions tend to slide downward due to gravity. As the bony portion of the patient's body moves downward, the skin covering the area can stay in its current position, thereby pulling in the opposite direction of the skeletal structure. Such shear motion can injure the skin and blood vessels at the site, causing the skin and other local tissue to be vulnerable to formation of a pressure ulcer.

An established practice for patients at risk of forming pressure ulcers is to follow a turning protocol by which the patient is periodically repositioned, or "turned" to redistribute pressure forces placed on various points of the patient's body. Individuals at risk for a pressure ulcer are repositioned regularly. It is commonly suggested that patients be repositioned every 2 hours at specific inclination angles, and that the method of doing so minimizes the amount of friction and shear on the patient's skin. A repositioning log can be maintained and include key information, such as the time, body orientation, and outcome.

Pressure ulcer prevention programs have been effective and can reduce long-term costs associated with treatment. A 2002 study employed a comprehensive prevention program in two long-term care facilities, costing $519.73 per resident per month. Results of the program revealed pressure ulcer prevalence to be reduced by 87% and 76% in the two facilities. A later study found that prevention strategies were able to reduce pressure ulcer prevalence from 29.6% to 0% in a medical intensive care unit, and from 9.2% to 6.6% across all units of the hospital. These interventions employed strategies such as manual patient repositioning and logging, tissue visualization and palpation, pressure-reducing mattresses, and use of risk assessment tools. Turning protocols, however, do not take into consideration position changes made by the patient between established turn intervals, which, in common practice, are neither observed nor recorded. Thus, it is possible that in some circumstances, the act of following a turn protocol can have an unintended negative clinical effect.

Caregivers employ a variety of medical devices (for example, physiological sensors) that interact with patient monitoring devices which display a significant amount of patient health information. Such information is typically displayed on handheld monitoring devices or stationary monitoring devices with limited visual "real estate." Often if not always, multiple patients are being monitored at once. Further, such health information is constantly fluctuating for multiple patients in a simultaneous manner, increasing the difficulty for a caregiver to locate, evaluate, and respond to a particular piece of health information for a particular patient. Because caregivers are under significant time pressure and only have a small amount of time to monitor, respond to, and/or treat individual patients under their care, it is incredibly difficult for caregivers to quickly obtain information regarding a patient's orientation at any given time, let alone evaluate such information and determine if the patient's orientation needs to be adjusted. Even the slightest speed advantage for caregivers in such situation can greatly reduce the likelihood that a patient will develop pressure ulcers and/or can enable caregivers to provide potentially life-saving treatment.

SUMMARY

This disclosure describes, among other things, embodiments of devices, systems, and/or methods for monitoring and/or displaying the orientation, position, and/or movement of a patient. As discussed throughout this disclosure, such monitoring can help to reduce or eliminate the formation of pressure ulcers in patients. This disclosure further describes an improved graphical user interface for displaying information related to a patient's orientation, position, and/or movement.

A patient monitor for monitoring an orientation of a patient to reduce a risk of the patient developing a pressure ulcer can comprise one or more hardware processors configured to receive output signals from a sensor attached to the patient. The sensor can be a wireless sensor and/or can include one or more accelerometers. The one or more hardware processors can be further configured to process said output signals and determine the patient's orientation. The one or more hardware processors can be further configured to maintain a plurality of timers, each of the plurality of timers associated with an available orientation of the patient and configured to account for a non-consecutive duration said patient is in said associated available orientation, wherein said non-consecutive duration is configured to vary in a first manner when said patient is oriented in said associated available orientation and vary in a second manner when said patient is not oriented in said associated available orientation. The patient monitor can further comprise a display screen configured to display an orientation trend of the patient in relation to a flat surface (for example, a bed) based on the maintained plurality of timers, wherein the one or more hardware processors are further configured to generate a structured display on the display screen. The structured display can comprise a patient representation configured to illustrate a current orientation of the patient in a bed, said current orientation being one of said available orientations. The non-consecutive duration can be configured to vary in the first manner by increasing when said patient is oriented in said associated available orientation and vary in the second manner by decreasing when said patient is not oriented in said associated available orientation. The non-consecutive duration can be configured to decrease down to a minimum of zero (0) when said patient is not oriented in said associated available orientation. The non-consecutive duration can be configured to increase up to a maximum value when said patient is oriented in said associated available orientation. The maximum value can equal, for example, 2 hours. When said non-consecutive duration increases above a maximum value, the one or more hardware processors of the patient monitor can be further configured to generate an alarm. The alarm can comprises at least one of a visual alarm and an auditory alarm. The one or more hardware processors of the patient monitor can be configured to generate a visual alarm by generating a flash or changing a color of the structured display. When said non-consecutive duration increases beyond a maximum value, the patient monitor can be configured to transmit a notification signal. The non-consecutive duration can be configured to vary in the first manner by decreasing when said patient is oriented in said associated available orientation and vary in the second manner by increasing when said patient is not oriented in said associated available orientation. The non-consecutive duration can be configured to decrease down to a minimum of zero (0) when said patient is oriented in said associated available orientation. The non-consecutive duration can be configured to increase up to a maximum value when said patient is not oriented in said associated available orientation. The maximum value can equal, for example, 2 hours. When said non-consecutive duration decreases below a minimum value, the one or more hardware processors of the patient monitor can be configured to generate an alarm. The alarm can comprise at least one of a visual alarm and an auditory alarm. The one or more hardware processors of the patient monitor can be configured to generate the visual alarm by generating a flash or changing a color of the structured display. When said non-consecutive duration decreases below a minimum value, the patient monitor can be configured to transmit a notification signal. The patient representation of the structured display can comprise at least a portion of a model patient. The patient representation of the structured display can comprise at least one of a 3D image of the model patient laying in a model hospital bed; an upper body of a 3D model patient; and a 3D image of the model patient in a walking or running position. The patient representation can further comprise one or more injury points. The structured display can comprise a heat map configured to graphically illustrate said non-consecutive durations of the patient in one or more of the available orientations. The heat map can be configured to vary in color based on the variability of said non-consecutive duration. The heat map can comprise a curved region bounded by a first curved segment and a second curved segment separated by a distance. The curved region can further comprise: a left end corresponding to a left side orientation of the patient in the hospital bed; and a right end corresponding to a right side orientation of the patient in the hospital bed, wherein a middle of the curved region corresponds to a supine position of the patient in the hospital bed and represents a line of symmetry of the curved region. The one or more hardware processors can be further configured to fill one or more of a plurality of lines in a selected portion of the curved region with a first color when the patient is in a first orientation less than a first time or a second color when the patient is in the first orientation greater than or equal to the first time. The one or more hardware processors can be configured to fill the one or more of the plurality of lines with either the first or second color in response to signal processing of data received from the sensor, and each of the plurality of lines can extend from the first curved segment to the second curved segment and represent a degree of orientation of the patient in the hospital bed. The one or more hardware processors can be configured to fill one or more of the plurality of lines with a third color representing an un-allowed patient orientation, and wherein the third color is different than both the first and second colors. The one or more hardware processors can be configured to display a hatched pattern between two of the plurality of lines in the curved region, wherein the hatched patent represents an un-allowed patient orientation. The structured display can further comprise an indicator located along the curved region and configured to indicate the current orientation of the patient in the hospital bed. The structured display can further comprise a patient inclination indicator configured to illustrate an incline position of the patient in the bed. The patient inclination indicator can be further configured to display an inclination degree of the patient in the bed. The structured display can further comprise a color legend. The structured display can further comprise an orientation graph configured to display a history of the patient's orientation over a time range.

For purposes of summarizing the disclosure, certain aspects, advantages, and novel features have been described herein. Of course, it is to be understood that not necessarily all such aspects, advantages, or features will be embodied in any particular embodiment.

BRIEF DESCRIPTION OF THE DRAWINGS

Throughout the drawings, reference numbers can be re-used to indicate correspondence between referenced elements. The following drawings and the associated descriptions are provided to illustrate embodiments of the present disclosure and do not limit the scope of the disclosure.

FIG. 8A-8D illustrate various shapes for a heat map of a structured display for a display screen of patient monitor in accordance with aspects of this disclosure.

Figure 1:
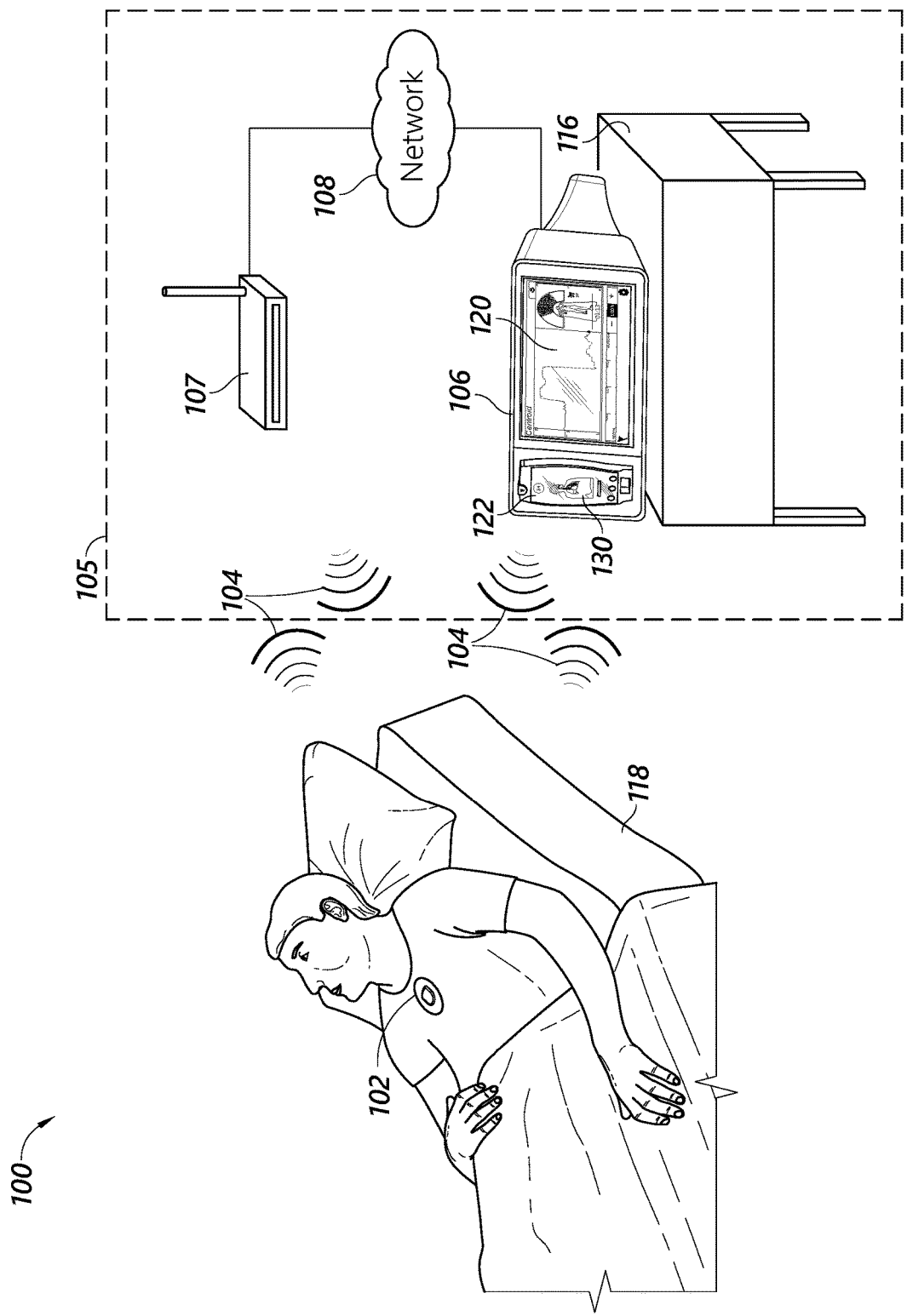
FIG. 1 is a perspective view of an embodiment of a patient monitoring system including a patient-worn wireless sensor and a patient monitor.

While the foregoing "Brief Description of the Drawings" references generally various embodiments of the disclosure, an artisan will recognize from the disclosure herein that such embodiments are not mutually exclusive. Rather the artisan would recognize a myriad of combinations of some or all of such embodiments.

DETAILED DESCRIPTION

Various embodiments will be described hereinafter with reference to the accompanying drawings. The drawings and the associated descriptions are provided to illustrate embodiments of the present disclosure and do not limit the scope of the claims. In the drawings, similar elements have similar reference numerals.

The present disclosure relates to devices, systems, and methods for monitoring and/or displaying information regarding a patient's position, orientation, and/or movement in a medical environment. The present disclosure also relates to an improved graphical user interface for displaying such information.

A system and/or method for monitoring and/or displaying information regarding a patient's position, orientation, and/or movement in a medical environment can include a patient-worn, wireless sensor including one or more sensors configured to obtain position, orientation and/or movement information from a patient and transmit such information to a patient monitor for display. The one or more sensors can include, for example, one or more accelerometers, gyroscopes, and/or magnetometers (i.e., compasses). Illustratively, the sensors can continuously or periodically (e.g., every second) obtain information that describes the patient's orientation in three dimensions. The wireless sensor can include a processor that is configured to process the obtained sensor information. The wireless sensor can also include a transmitter or transceiver configured to wirelessly transmit the processed sensor data, and/or information representative to and/or responsive to the sensor data, to a patient monitor (or other processing device) for further processing. The patient monitor can be configured to store and further process the received information, to display information indicative of or derived from the received data, and to transmit information to other patient care systems such as a multi-patient monitoring system which may be accessible from, for example, a nurses' station. The patient monitor can be configured to display and/or transmit alarms, alerts, and/or notifications to an external device and/or patient care system. The patient monitor can include a structured graphical user interface which displays the above-mentioned information in a static and/or dynamic fashion.

FIG. 1 is a perspective illustration of a patient monitoring system 100 in a clinical setting. The patient monitoring system 100 can include a wireless sensor 102 (also referred to herein as "a wireless physiological sensor 102," "a patient-worn sensor 102," "a movement sensor 102," and "a wearable wireless sensor 102") that can be worn by and/or attached to a patient and a patient monitor 106 that can wirelessly communicate with the wireless sensor 102. As an example, the wireless sensor 102 and the patient monitor 106 can be positioned in proximity with one another in a hospital room, and the patient monitor 106 can be located on a table 116 at the side of the patient's bed 118. While the disclosure below discusses a wireless sensor 102, the patient monitoring system 100 can include a plurality of wireless sensors 102, such as one, two, three four, five, six or seven or more wireless sensors 102. The wireless sensor 102 includes one or more sensors configured to measure the patient's position, orientation, and/or motion. The wireless sensor 102 can include one or more accelerometers configured to measure linear acceleration of the patient in one or more directions (for example, axes). The wireless sensor 102 can additionally or alternatively include one or more gyroscopes configured to measure angular velocity of the patient. The measured linear acceleration and/or angular velocity information can be processed to determine the patient's orientation in three dimensions. In some embodiments, a magnetometer is included in the wireless sensor 102 to measure the Earth's gravitational field. Information measured by the magnetometer can be used to improve accuracy of the determined orientation of the patient.

The wireless sensor 102 can also include a wireless transceiver 206 (see FIGS. 4A and 4B) which can transmit to the patient monitor 106 information representative of sensor data obtained by the wireless sensor 102 from the patient. Advantageously, the patient can be physically decoupled from the bedside patient monitor 106 and can therefore move freely into and/or out of different positions and/or orientations on the bed 118.

The wireless sensor 102 can be affixed to the skin of the patient's body under the patient's garment as shown in FIG. 1. For example, the wireless sensor 102 can be placed on the patient's torso. For example, the sensor 102 can be placed on the patient's chest over the patient's manubrium, the broad upper portion of the sternum. In this position, the wireless sensor 102 can be approximately centered relative to the longitudinal axis of the patient's body and near the patient's center of mass, a position that is useful in determining the patient's orientation when, for example, the patient is in a bed 118. The wireless sensor 102 can be affixed to or otherwise placed on various portions of the patient's body in addition to or as an alternative to placement on the patient's chest. For example, the wireless sensor 102 can be placed on the patient's back or more specifically, may be placed between a patient's shoulder blades or on other portions of the patient's back. The wireless sensor 102 can receive and/or measure signals indicative of and/or responsive to a temperature, a vibration, a movement, and/or a heartbeat, among other parameters.

The wireless sensor 102 can be affixed to the patient's skin using any form of medically-appropriate adherent material, including a pressure-sensitive adhesive that is coated or applied to the bottom surface of the wireless sensor 102. One skilled in the art will appreciate that many other materials and techniques can be used to affix the wireless sensor 102 to the patient without departing from the scope of the present disclosure.

Frequently in clinical settings, multiple medical sensors are attached or adhered to a patient to concurrently monitor multiple physiological parameters. Some examples of medical sensors include, but are not limited to, position, orientation, and/or movement sensors, temperature sensors, respiration sensors, heart rate sensors, blood oxygen sensors (such as pulse oximetry sensors), acoustic sensors, electroencephalography (EEG) sensors, electrocardiogram (ECG) sensors, blood pressure sensors, sedation state sensors, to name a few. Typically, each sensor that is attached to a patient transmits, often by cable, the obtained physiological data to a nearby monitoring device configured to receive and process the sensor data, and transform it into clinical information to be used by care providers to monitor and manage the patient's condition. When a patient is concurrently monitored by several physiological sensors, the number of cables and the number of bedside monitoring devices used can be excessive and can limit the patient's freedom of movement and impede care providers' access to the patient. The cables connecting the patient to the bedside monitoring devices can also make it more difficult to move the patient from room to room or to switch to different bedside monitors.

Advantageously, the disclosed wireless sensor 102 can transmit data, wirelessly, to a patient data processing environment 105 in which the sensor data can be processed using one or more processing capabilities. As illustrated in FIG. 1, the wireless sensor 102 can transmit data, via a wireless communications link 104, to a bedside patient monitor 106 and/or an extender/repeater 107. Both the patient monitor 106 and extender/repeater 107 provide access, by way of high-speed and reliable communications interfaces, to the patient data processing environment 105. For illustration purposes, both the patient monitor 106 and the extender/repeater 107 are illustrated in FIG. 1. However, typically only one such device is required to establish a wireless connection between the wireless sensor 102 and the patient data processing environment 105. The wireless communications link 104 can use any of a variety of wireless technologies, such as Wi-Fi (802.11x), Bluetooth, ZigBee, cellular telephony, infrared, RFID, satellite transmission, proprietary protocols, combinations of the same, and the like. The wireless sensor 102 can be configured to perform telemetry functions, such as measuring and reporting position, orientation, and movement information about the patient. According to one embodiment, the wireless sensor 102 uses the Bluetooth wireless communications standard to communicate wirelessly with the patient monitor 106.

The extender/repeater 107 can receive sensor data from the wireless sensor 102 by way of the wireless communications link 104 and forward the received sensor data, via a network 108, to one or more processing nodes within the patient data processing environment 105. For example, the extender/repeater 107 can forward the received sensor data to a patient monitor 106 that might be located beyond the range of the wireless communications link 104 of a particular wireless sensor 102. Alternatively, the extender/repeater 107 can route the sensor data to other processing nodes within the patient data processing environment 105, such as, for example, a multi-patient monitoring system 110 or a nurses' station system 113 (see FIG. 3B). A skilled artisan will appreciate that numerous processing nodes and systems can be used to process the data transmitted by the wireless sensor 102.

FIG. 1 also illustrates the patient monitor 106, which may also be referred to herein as "a processing device 106," "a portable computing device 106," and "a patient monitoring device 106." An example of a patient monitor 106 is disclosed in U.S. Pat. No. 10,010,276, which is incorporated by reference herein in its entirety. The patient monitor 106 is a processing device, and therefore includes the necessary components to perform the functions of a processing device, including at least one hardware processor, a memory device, a storage device, input/output devices, and communications connections, all connected via one or more communication buses. In some embodiments, the patient monitor 106 is a mobile phone (e.g., a smartphone), which can be configured to display the structured display 410, 610, 710 or components thereof, which are described further below. For example, the patient monitor 106 can be a mobile phone configured to display the patient representation 424, bed 422, heat map 414, 514, 614, 714, legend 418, orientation graph 433, and/or timer 426, or portions or aspects thereof. As another example, the patient monitor 106 can be a mobile phone (e.g., a smartphone), which can be configured to display that which appears in FIGS. 6, 7, 8A, 8B, 8C, 8D, 9A, 9B, 10, 11, 12, 13, and/or 14. As another example, the patient monitor 106 can be a mobile phone (e.g., a smartphone), which can be configured to display that which appears in the display portion 415 and/or 412 as shown in any of FIGS. 6, 7, 9A, 11, 12, and/or 13. For example, the patient monitor 106 can be a mobile phone (e.g., a smartphone), which can be configured to display only the heat map 414, 514, 614, 714, the patient representation 424, the model bed 422, patient inclination indicator 421, patient inclination degree indicator 420, timer 426, and/or legend 418. As another example, the patient monitor 106 can be a mobile phone (e.g., a smartphone), which can be configured to display only the orientation graph 433, patient inclination indicator 421, patient inclination degree indicator 420, timer 426, and/or legend 418. Given the limited visual "real estate" that may be available in many patient monitors 106 (such as mobile phones), limiting the display to include only one or more of these components can allow a caregiver to quickly obtain a holistic sense of the patient's orientation history and/or condition in order to provide better treatment.

In certain embodiments, the patient monitor 106 can process the sensor data provided by the wireless sensor 102. In other embodiments, processing of the sensor data can be performed by other processing nodes within the patient data processing environment 105. The patient monitor 106 can wirelessly communicate with the wireless sensor 102. The patient monitor 106 can include a display 120 (also referred to herein as a "display screen") and/or a docking station that can mechanically and electrically mate with a portable patient monitor 122 also having a display 130. The patient monitor 106 can be contained within a movable, mountable, and portable housing formed in a generally upright, inclined shape configured to rest on a horizontal flat surface, as shown in FIG. 1. Of course, a person skilled in the art will appreciate that the housing of the patient monitor 106 can be affixed in a wide variety of positions and mountings and can have a wide variety of shapes and sizes.

The display 120, alone or in combination with the display 130 of the portable patient monitor 122, can present a wide variety of measurement and/or treatment data in numerical and/or graphical (e.g., waveform) forms and/or can contain various display indicia. For example, the display 120 can display a variety of patient-specific configurations and/or parameters, such as the patient's weight, age, type of treatment, type of disease, type of medical condition, nutrition, hydration and/or length of stay, among others. In an embodiment, the display 120 occupies much of a front face of a housing of the patient monitor 106, although an artisan will appreciate the display 120 may comprise a table or tabletop horizontal configuration, a laptop-like configuration, or the like. Other embodiments may include communicating display information and data to a tablet computer, smartphone, television, or any display system recognizable to an artisan. Advantageously, the upright inclined configuration of the patient monitor 106, as illustrated in FIG. 1, displays information to a caregiver in an easily viewable manner. In an embodiment, the display 120 is a single screen display with a limited amount of screen space (also referred to herein as "real estate"). For example, the single screen display may be about 10 inches diagonal. In an embodiment, the display 120 is that made commercially available by Masimo Corporation of Irvine, CA on the patient monitoring platform called Root®.

The portable patient monitor 122 of FIG. 1 can advantageously include an oximeter, co-oximeter, respiratory monitor, depth of sedation monitor, noninvasive blood pressure monitor, and/or vital signs monitor. The portable patient monitor 122 may communicate with a variety of noninvasive and/or minimally invasive devices such as, by way of non-limiting example, wireless sensor 102, optical sensors with light emission and detection circuitry, acoustic sensors, devices that measure blood parameters from a finger prick, cuffs, ventilators, and the like. The portable patient monitor 122 can include its own display 130 presenting its own display indicia related to physiological parameters of a patient. The display indicia may change based on a docking state of the portable patient monitor 122. When undocked, the display 130 may include parameter information and may alter its display orientation based on information provided by, for example, a gravity sensor or an accelerometer. Although disclosed with reference to particular portable patient monitors 122, an artisan will recognize from the disclosure herein there is a large number and wide variety of medical devices that may advantageously dock with the patient monitor 106.

Figure 2A:
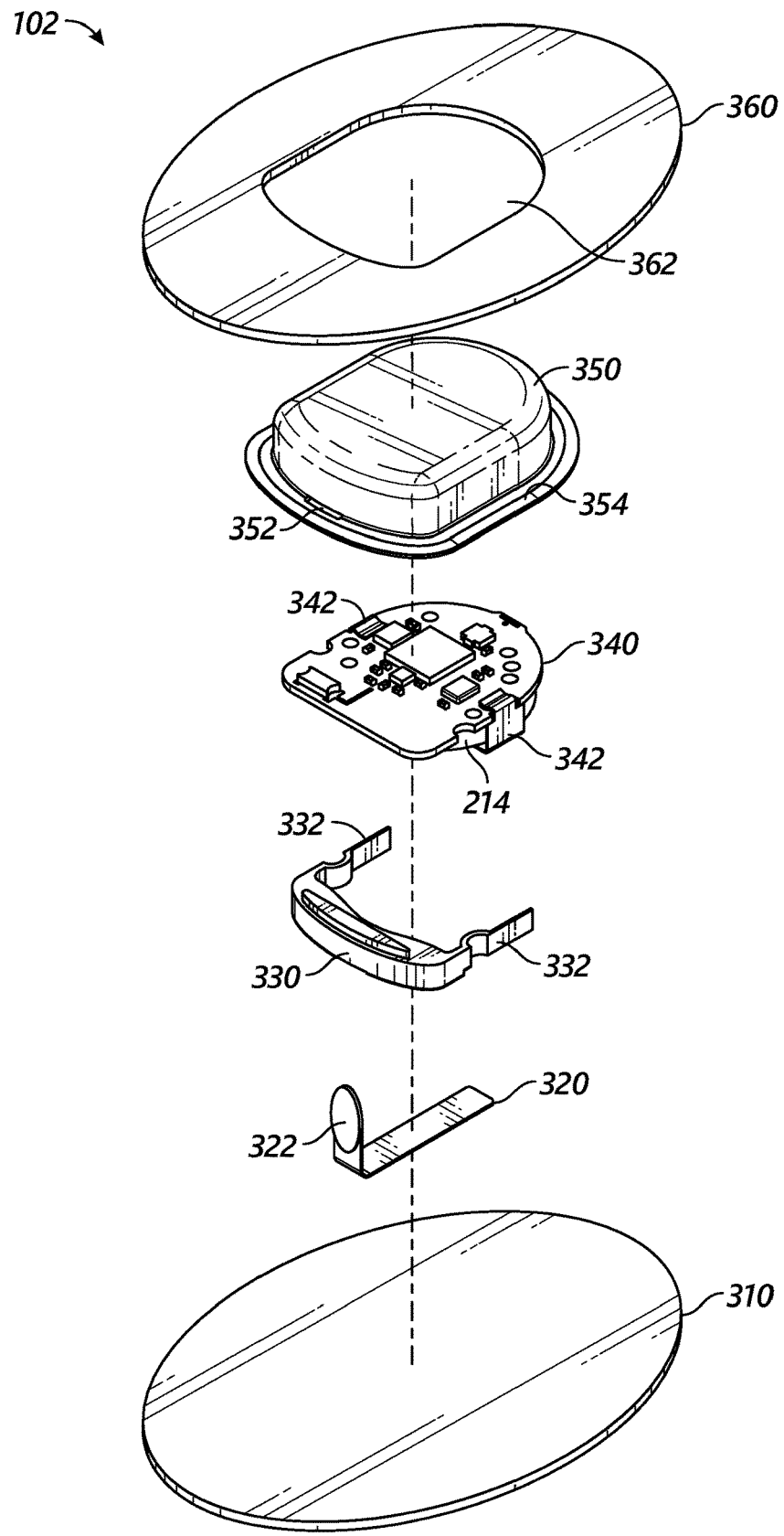
FIG. 2A is an exploded perspective view of the wireless sensor of FIG. 1.

FIG. 2A is a schematic exploded perspective view of an embodiment of the disclosed wireless sensor 102 including a bottom base 310, a removable battery isolator 320, a mounting frame 330, a circuit board 340, a housing 350, and a top base 360. The bottom base 310 can be a substrate having a top surface on which various components of the wireless sensor 102 are positioned, and a bottom surface that is used to affix the wireless sensor 102 to the patient's body. The bottom base 310 and top base 360 can be made of medical-grade foam material such as white polyethylene, polyurethane, or reticulated polyurethane foams, to name a few. As illustrated in the embodiment illustrated in FIG. 2A, the bottom base 310 and the top base 360 can each have a substantially oval shape, with a thickness of approximately 1 mm, for example. The top base 360 can include a cut-out 362 through which the housing 350 fits during assembly. Of course, a skilled artisan will understand that there are numerous sizes and shapes suitable for the top and bottom bases 310 and 360 that can be employed without departing from the scope of the present disclosure. The bottom surface of the bottom base 310 can be coated with a high tack, medical-grade adhesive, which when applied to the patient's skin, can be suitable for long-term monitoring, such as, for example two days or longer. Portions of the top surface of the bottom base 310 can also be coated with a medical-grade adhesive, as the bottom base 310 and the top base 360 are adhered together during assembly of the wireless sensor 102.

The removable battery isolator 320 can be a flexible strip made of an electrically insulating material that serves to block electrical communication between the battery 214 and an electrical contact (not shown) on the circuit board 340. The battery isolator 320 can be used to preserve battery power until the wireless sensor 102 is ready for use. The battery isolator 320 can block electrical connection between the battery 214 and the circuit board 340 until the battery isolator 320 is removed from the wireless sensor 102. The battery isolator 320 can be made of any material that possesses adequate flexibility to be slidably removed from its initial position and adequate dielectric properties so as to electrically isolate the battery from the circuit board 340. For example, the battery isolator 320 can be made of plastic, polymer film, paper, foam, combinations of such materials, or the like. The battery isolator 320 can include a pull tab 322 that extends through a slot 352 of the housing 350 when the wireless sensor 102 is assembled. The pull tab 322 can be textured to provide a frictional surface to aid in gripping and sliding the pull tab 322 out of its original assembled position. Once the battery isolator 320 is removed the battery 214 can electrically connect with the battery contact to energize the electronic components of the wireless sensor 102.

The mounting frame 330 is a structural support element that can help secure the battery 214 to the circuit board 340. The mounting frame 340 has wings 342 that, when assembled are slid between battery contacts 342 and the battery 214. Additionally, the mounting frame 330 serves to provide rigid structure between the circuit board 340 and the bottom base 310. According to some embodiments that include an acoustic respiratory sensor, the rigid structure transmits vibrational motion (vibrations) emanating from the patient (such as, for example, vibrational motions related to respiration, heartbeat, snoring, coughing, choking, wheezing, respiratory obstruction, and the like) to the accelerometer 210 positioned on the circuit board 340.

The circuit board 340, which may also be referred to herein as a substrate layer 340 and a circuit layer 340, mechanically supports and electrically connects electrical components to perform many of the functions of the wireless sensor 102. The circuit board 340 can include conduction tracks and connection pads. Such electrical components can include without limitation, a processor 202, a storage device 204, a wireless transceiver 206, an accelerometer 210, a gyroscope 212, a magnetometer 216, a temperature sensor 218, an acoustic respiration sensor 220, an ECG sensor 222, an oximetry sensor 224, a moisture sensor 226, and/or an impedance sensor 228 (see FIGS. 4A-4B). In an embodiment, the circuit board 340 is double-sided and has electronic components mounted on a top side and a battery contact (not shown) on a bottom side. Of course a skilled artisan will recognize other possibilities for mounting and interconnecting the electrical and electronic components of the wireless sensor 102.

As illustrated in FIG. 2A, a battery holder 342 can be attached to two sides of the top portion circuit board 340 and can extend (forming a support structure) under the bottom side of the circuit board 340 to hold the battery 214 in position relative to the circuit board 340. The battery holder 342 can be made of electrically conductive material. In some embodiments, the battery 214 is a coin cell battery having a cathode on the top side and an anode on the bottom side. Electrical connection between the anode of the battery 214 and the circuit board 340 can be made by way of the battery holder which is in electrical contact with the anode of the battery 214 and the circuit board 340. The cathode of the battery 214 can be positioned to touch a battery contact (not shown) on the bottom side of the circuit board 340. In some embodiments, the battery contact includes a spring arm that applies force on the battery contact to ensure that contact is made between the anode of the battery 214 and the battery contact. During assembly and prior to use, the battery isolator 320 is inserted between the anode of the battery 214 and the battery connector to block electrical contact.

The housing 350 is a structural component that serves to contain and protect the components of the wireless sensor 102. The housing 350 can be made of any material that is capable of adequately protecting the electronic components of the wireless sensor 102. Examples of such materials include without limitation thermoplastics and thermosetting polymers. The housing 350 can include a slot 352 through which the battery isolator 320 is inserted during assembly. The housing 350 can also include a rim 354 that extends around the outer surface of the housing 350. The rim 354 can be used to secure the housing 350 in position relative to the bottom base 310 and the top base 360 when the wireless sensor 102 is assembled.

The wireless sensor 102 can be assembled in a variety of ways. The circuit board 340 and battery holder 342 holding the battery 214 can be placed into the housing 350. The wings 332 of the mounting frame 330 can be inserted in between the battery 214 and the battery holder 342 so as to align the mounting frame 330 with the circuit board 340. The battery isolator 320 can then be positioned between the battery contact and the battery 214. The pull tab 322 of the battery isolator 320 can then be fed through the slot 352 in the housing 350. The top base 360 can then be positioned over the housing 350, which can house the assembled circuit board 340, battery holder 342, battery 214, mounting frame 330, and battery isolator 320, using the cut-out 362 for alignment. The rim 354 of the housing 350 can adhere to the bottom surface of the top base 360, which can be coated with high tack, medical-grade adhesive. The partial assembly, which now includes the top base 360, the housing 350, the circuit board 340, the battery holder 342, the battery 214, the mounting frame 330, and the battery isolator 320, can be positioned centrally onto the top surface of the bottom base 310, aligning the edges of the base top 360 with the edges of the base bottom 310. In some embodiments, a coupon (or die cutting tool) is used to cut away excess portions of the now combined top and bottom bases 360 and 310 to form a final shape of the wireless sensor 102. The bottom surface of the bottom base 310 can then be coated with a high tack, medical-grade adhesive, and a release liner (not shown) can be placed on the bottom surface of the bottom base 310 to protect the adhesive until it is time for use.

Figure 2B:
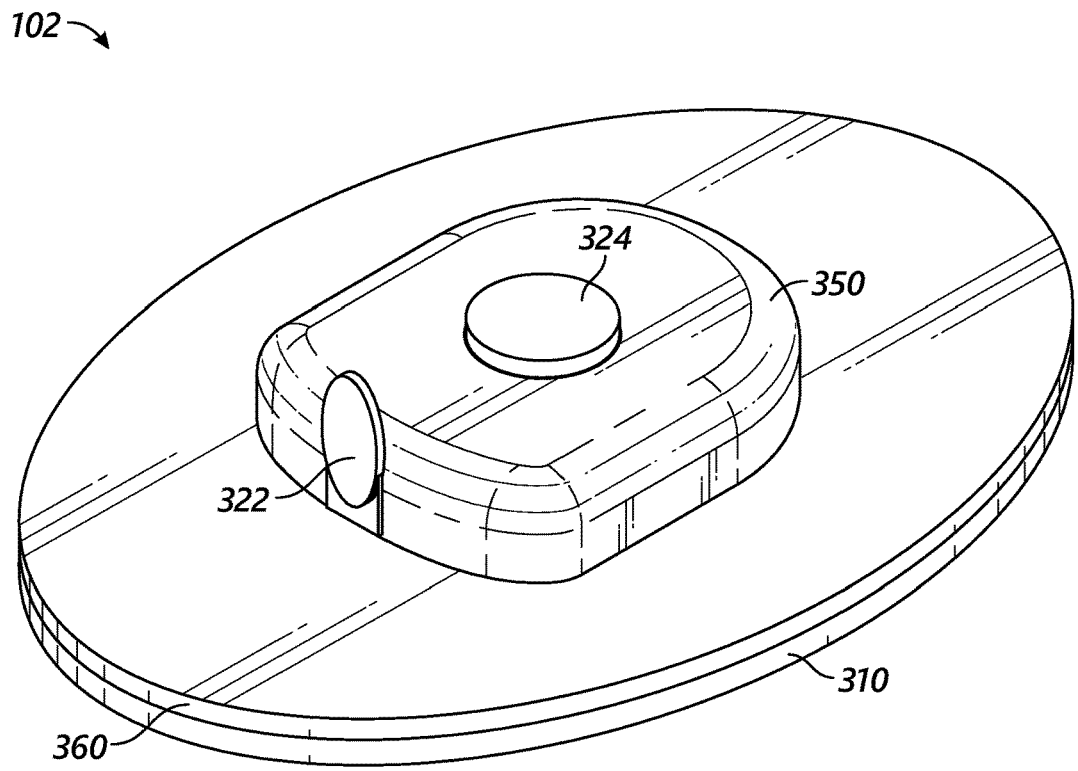
FIG. 2B is an assembled perspective view of the wireless sensor of FIG. 1.
Figure 2C:
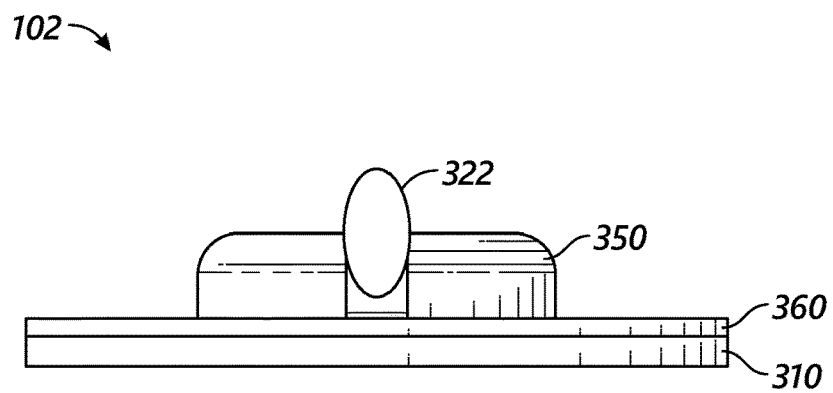
FIG. 2C is a side view of the wireless sensor of FIG. 1.

A perspective view of the assembled wireless sensor 102 is illustrated in FIG. 2B. Also illustrated in FIG. 2B is a button/switch 324 located on a top portion of the housing 350. The button/switch 324 can be used to change modes of the wireless sensor 102. For example, in some embodiments, pressing and holding the button/switch 324 can cause the wireless sensor 102 to switch into a pairing mode of operation. The pairing mode can be used to associate the wireless sensor 102 with a patient monitor 106 or with an extender/repeater 107. Methods and systems for pairing a sensor to a patient monitor are disclosed in U.S. Pat. No. 10,383,527, which is hereby incorporated by reference in its entirety. FIG. 2C provides a side view of an embodiment of the assembled wireless sensor 102.

Figure 3A:
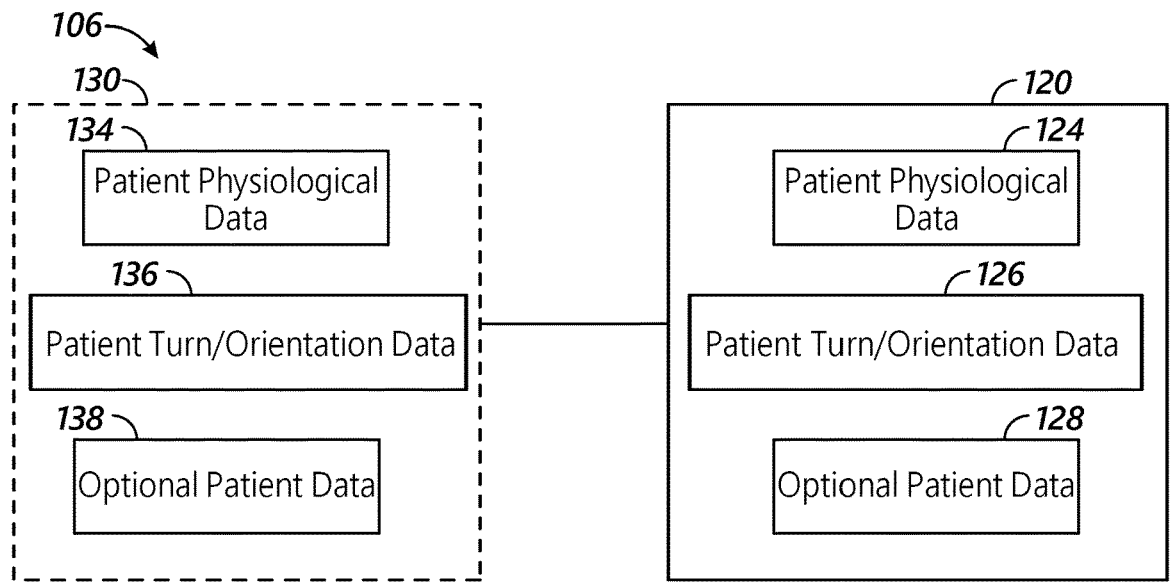
FIG. 3A is a functional block diagram of an embodiment of a display of the patient monitor of FIG. 1 in accordance with aspects of this disclosure.

FIG. 3A is a functional block diagram of an embodiment of the display 120 of the disclosed patient monitor 106 and the display 130 of the portable patient monitor 122. Display 120 of the patient monitor 106 can be configured to present patient physiological data 124, patient turn and/or orientation data 126, and/or additional, optional patient data 128. Patient physiological data 124 can include, by way of non-limiting example, oxygen saturation, pulse rate, respiration rate, fractional arterial oxygen saturation, total hemoglobin, plethysmograph variability index, methemoglobin, carboxyhemoglobin, perfusion index, and/or oxygen content. Advantageously, the display 120 can be configurable to permit the user to adjust the manner by which the physiologic parameters 124, patient turn data 126, and optional patient data 128 are presented on the display 120. In particular, information of greater interest or importance to the clinician may be displayed in larger format and may also be displayed in both numerical and graphical formats to convey the current measurement as well as a historical trend of measurements for a period of time, such as, for example, the preceding hour. Further, the display 120 can be configurable to permit the user to modify which of patient physiological data 124, patient turn and/or orientation data 126, and/or optional patient data 128 is shown. For example, the display 120 can be configurable such that only patient turn and/or orientation data 126 is shown.

As illustrated by dotted lines in FIG. 3A, the display 130 of the portable patient monitor 130 is an optional feature of the patient monitor 106 which may be configured to present patient physiological data 134, patient turn and/or orientation data 136, and additional, optional patient data 138.

Figure 3B:
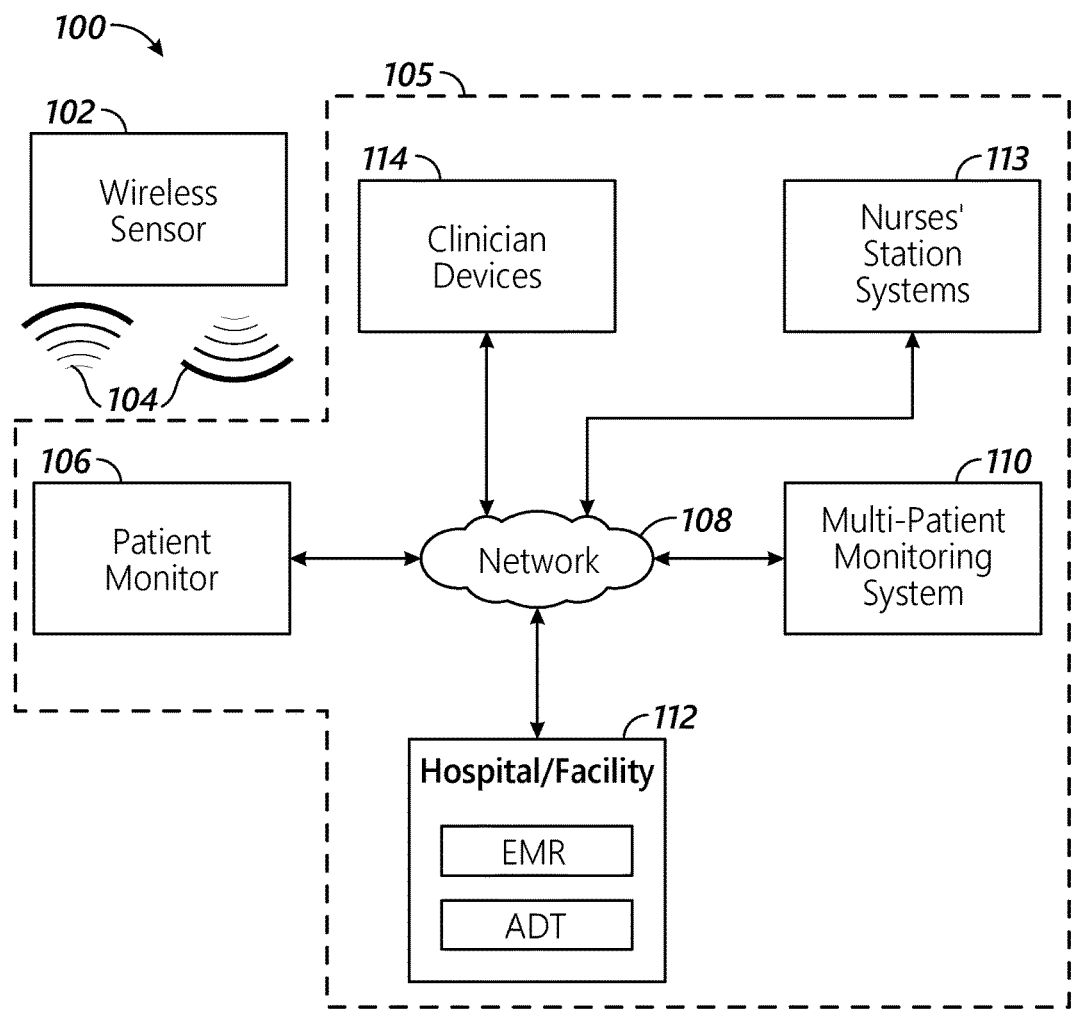
FIG. 3B is a functional block diagram of an embodiment of a patient monitoring system in accordance with aspects of this disclosure.

FIG. 3B is a simplified functional block diagram of an embodiment of patient monitoring system 100. The system can include the patient-worn wireless sensor 102, a wireless communications link 104, through which sensor data from the wireless sensor 102 can be transmitted, and the patient data processing environment 105. The patient data processing environment 105 can include a patient monitor 106, a communications network 108, a multi-patient monitoring system 110, a hospital or facility information system 112, one or more nurses' station systems 113, and/or one or more clinician devices 114. An artisan will appreciate that numerous other computing systems, servers, processing nodes, display devices, printers, and the like can be included in the disclosed patient monitoring system 100.

The wireless sensor 102 can be worn by a patient who has been determined to be at risk of forming one or more pressure ulcers, for example, a patient who is confined to bed for an extended period of time. The wireless sensor 102 can continuously or periodically (e.g., every second) monitor the orientation of the patient to help determine whether the patient is repositioned frequently enough to reduce the patient's risk of forming a pressure ulcer. In certain embodiments, the wireless sensor 102 minimally processes measured acceleration and/or angular velocity data and wirelessly transmits the minimally-processed data to the patient monitor 106 by way of the wireless communications link 104. In some cases, such minimal processing can conserve power of the wireless sensor 102.

The wireless sensor 102 and the patient monitor 106 can be configured to utilize different wireless technologies to form the wireless communications link 104. In certain scenarios, it may be desirable to transmit data over Bluetooth or ZigBee, for example, when the distance between the wireless sensor 102 and the patient monitor 106 is within range of Bluetooth or ZigBee communication. Transmitting data using Bluetooth or ZigBee can be advantageous because these technologies require less power than other wireless technologies. Accordingly, longevity of embodiments of the disclosed wireless sensor 102 using batteries may be increased by using Bluetooth or ZigBee protocols.

In other scenarios, it may be desirable to transmit data using Wi-Fi or cellular telephony, for example, when the distance between the wireless sensor 102 and the patient monitor 106 is out of range of communication for Bluetooth or ZigBee. A wireless sensor 102 may be able to transmit data over a greater distance using Wi-Fi or cellular telephony than other wireless technologies. In still other scenarios, it may be desirable to transmit data using a first wireless technology and then automatically switching to a second wireless technology in order to maximize data transfer and/or energy efficiency.

In some embodiments, the wireless sensor 102 automatically transmits data over Bluetooth or ZigBee when the wireless sensor 102 is within a pre-determined distance from the bedside patient monitor 106. The wireless sensor 102 automatically transmits data over Wi-Fi or cellular telephony when the wireless sensor 102 is beyond a pre-determined distance away from the bedside patient monitor 106. In certain embodiments, the wireless sensor 102 can automatically convert from Bluetooth or ZigBee to Wi-Fi or cellular telephony, and vice versa, depending on the distance between the wireless sensor 102 and the bedside patient monitor 106.

In some embodiments, the wireless sensor 102 automatically transmits data over Bluetooth or ZigBee when the Bluetooth or ZigBee signal strength is sufficiently strong or when there is interference with Wi-Fi or cellular telephony. The wireless sensor 102 automatically transmits data over Wi-Fi or cellular telephony when the Bluetooth or ZigBee signal strength is not sufficiently strong. In certain embodiments, the wireless sensor 102 can automatically convert from Bluetooth or ZigBee to Wi-Fi or cellular telephony, and vice versa, depending on signal strength.

The patient monitor 106 can be operable to receive, store, and process the measured acceleration and angular velocity data transmitted by the wireless sensor 102 to determine the patient's orientation. Once determined, the patient monitor 106 can display the patient's current orientation and/or information related to the orientation. In some embodiments, the patient monitor 106 can display the patient's current orientation along with the patient's previous orientations over time, thereby providing a user (for example, a caregiver) the ability to view a historical record of the patient's orientation. As discussed in more detail below, the patient orientation and/or information related to the patient's orientation over time can be displayed and/or illustrated by a patient representation, historical graph, "heat map" (defined below), and/or timer, enabling the clinician to readily understand the patient's present positional state and the patient's position and/or orientation history. The patient monitor 106 can also be configured to keep track of the length of time the patient remains in a particular orientation. In some embodiments, the patient monitor 106 can display the amount of time the patient has been in the current (e.g., present) orientation. Additionally, the patient monitor 106 can determine when the patient remains in a particular orientation for a duration greater than that prescribed by a clinician according to a repositioning (e.g., turning) protocol. Under such conditions, the patient monitor 106 can issue alarms, alerts, and/or notifications to the patient and/or to caregivers indicating that the patient should be repositioned to adhere to the prescribed repositioning protocol to reduce the risk of pressure ulcer formation.

As illustrated in FIG. 3B, the patient monitor 106 can communicate over a network 108 in a patient data processing environment 105 that can include a multi-patient monitoring system 110, a hospital/facility system 112, nurses' station systems 113, and/or clinician devices 114. In general, the multi-patient monitoring system 110 can communicate with the hospital/facility system 112, the nurses' station systems 113, and/or clinician devices 114. The hospital/facility system 112 can include systems such as electronic medical record (EMR) and/or and admit, discharge, and transfer (ADT) systems. The multi-patient monitoring system 110 may advantageously obtain through push, pull or combination technologies patient information entered at patient admission, such as patient identity information, demographic information, billing information, and the like. The patient monitor 106 can access this information to associate the monitored patient with the hospital/facility systems 112. Communication between the multi-patient monitoring system 110, the hospital/facility system 112, the nurses' station systems 113, the clinician devices 114, and the patient monitor 106 may be accomplished by any technique recognizable to an artisan from the disclosure herein, including wireless, wired, over mobile or other computing networks, or the like.

Figure 3C:
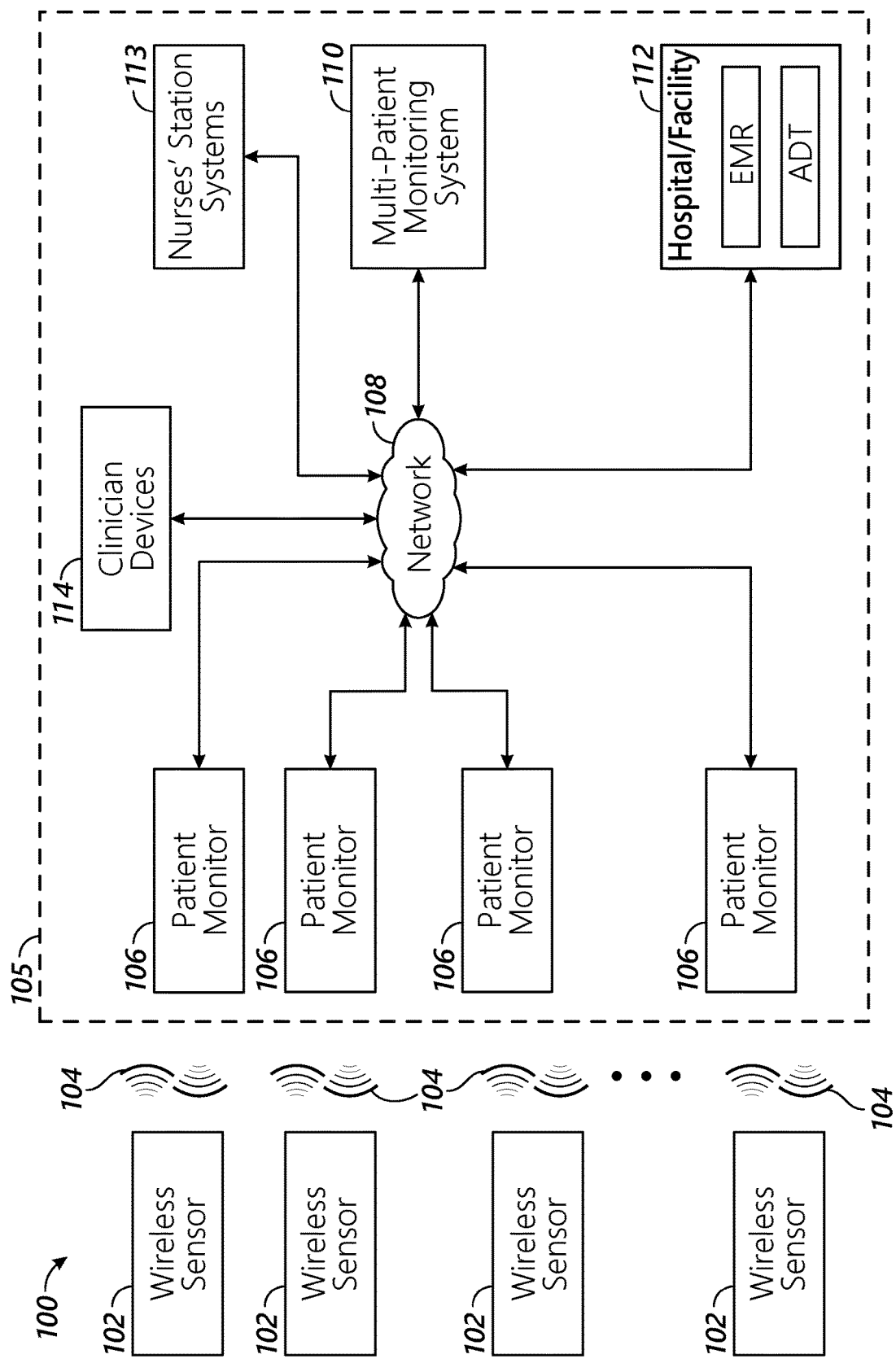
FIG. 3C is a functional block diagram of another embodiment of a patient monitoring system in accordance with aspects of this disclosure.

FIG. 3C is a simplified functional block diagram of the disclosed patient monitoring system 100 of FIG. 3B expanded to illustrate use of multiple wireless sensors 102 with multiple patients within a caretaking environment. Advantageously, the patient monitoring system 100 can provide individual patient information on, for example, a patient monitor 106, as well as aggregated patient information on, for example, a nurses' station server or system 113. Thus, a caretaker can be presented with an overview of positional information corresponding to a population of patients located, for example, in a hospital floor or unit.

Figure 4A:
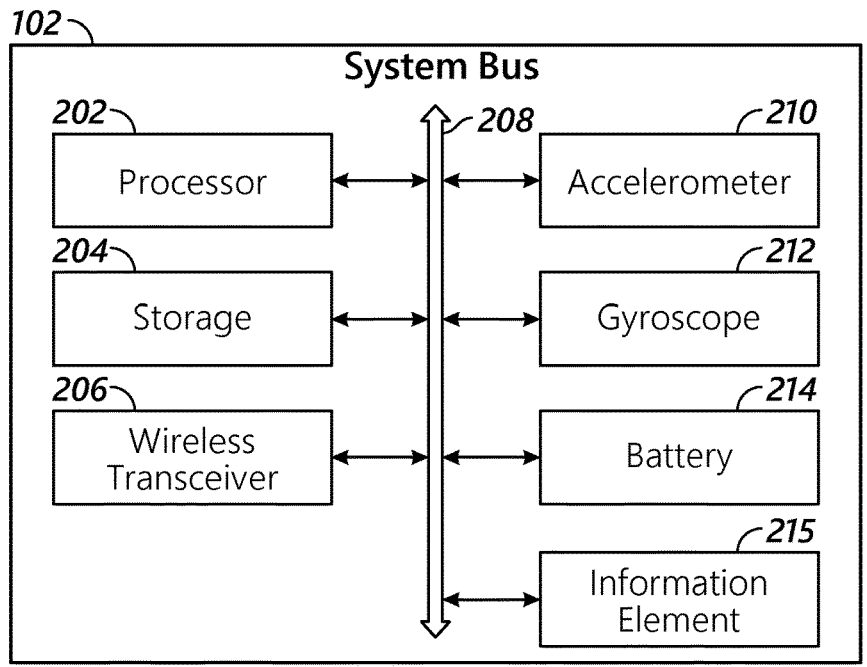
FIG. 4A is a functional block diagram of an embodiment of the wireless sensor of FIG. 1 in accordance with aspects of this disclosure.

FIG. 4A illustrates a simplified hardware block diagram of an embodiment of the disclosed wireless sensor 102. As shown in FIG. 4A, the wireless sensor 102 can include a processor 202, a data storage device 204, a wireless transceiver 206, a system bus 208, an accelerometer 210, a gyroscope 212, a battery 214, and an information element 215. The processor 202 can be configured, among other things, to process data, execute instructions to perform one or more functions, such as the methods disclosed herein, and control the operation of the wireless sensor 102. The data storage device 204 can include one or more memory devices that store data, including without limitation, random access memory (RAM) and read-only memory (ROM). The wireless transceiver 206 can be configured to use any of a variety of wireless technologies, such as Wi-Fi (802.11x), Bluetooth, ZigBee, cellular telephony, infrared, RFID, satellite transmission, proprietary protocols, combinations of the same, and the like. The components of the wireless sensor 102 can be coupled together by way of a system bus 208, which may represent one or more buses. The battery 214 provides power for the hardware components of the wireless sensor 102 described herein. As illustrated in FIG. 4A, the battery 214 communicates with other components over system bus 208. One skilled in the art will understand that the battery 214 can communicate with one or more of the hardware functional components depicted in FIG. 4A by one or more separate electrical connections. The information element 215 can be a memory storage element that stores, in non-volatile memory, information used to help maintain a standard of quality associated with the wireless sensor 102. Illustratively, the information element 215 can store information regarding whether the sensor 102 has been previously activated and whether the sensor 102 has been previously operational for a prolonged period of time, such as, for example, four hours. The information stored in the information element 215 can be used to help detect improper re-use of the wireless sensor 102.

The accelerometer 210 can be a three-dimensional (3D) accelerometer. The term 3D accelerometer as used herein includes its broad meaning known to a skilled artisan. Measurements from the accelerometer 210 of the wireless sensor 102 can be used to determine the patient's orientation. The accelerometer 210 can measure and output signals related to a linear acceleration of the patient with respect to gravity along three axes (for example, three, mutually orthogonal axes). For example, one axis, referred to as "roll," can correspond to the longitudinal axis of and/or extending through the patient's body (for example, along a length and/or height of the patient). Accordingly, the roll reference measurement can be used to determine whether the patient is in the prone position (for example, face down), the supine position (for example, face up), or on a side. Another reference axis of the accelerometer 210 is referred to as "pitch." The pitch axis can correspond to the locations about the patient's hip (for example, an axis extending between and/or through the patient's hips). The pitch measurement can be used to determine whether the patient is sitting up or lying down. A third reference axis of the accelerometer 210 is referred to as "yaw." The yaw axis can correspond to a horizontal plane in which the patient is located. When in bed, the patient can be supported by a surface structure that generally fixes the patient's orientation with respect to the yaw axis. Thus, in certain embodiments, the yaw measurement is not used to determine the patient's orientation when in a bed. The three axes that the accelerometer 210 can measure linear acceleration with respect to can be referred to as the "X," "Y," and "Z" axes.

The accelerometer 210 can provide acceleration information along three axes, and it can provide acceleration information which is the equivalent of inertial acceleration minus local gravitational acceleration. The accelerometer 210 may be a micro-electromechanical system (MEMS), and it may include piezo-resistors, among other forms of implementation. The accelerometer 210 may be a high-impedance charge output or a low-impedance charge output accelerometer 210. In some embodiments, the accelerometer 210 may be a tri-axial accelerometer, and the output of the accelerometer 210 may include three signals, each of which represents measured acceleration along a particular axis. The output of the accelerometer 210 can be 8-bit, 12-bit, or any other appropriate-sized output signal. The outputs of the accelerometer may be in analog or digital form. The accelerometer 210 can be used to determine the position, orientation, and/or motion of the patient to which the wireless sensor 102 is attached.

In some embodiments, the gyroscope 212 is a three-axis digital gyroscope with angle resolution of two degrees and with a sensor drift adjustment capability of one degree. The term three-axis gyroscope as used herein includes its broad meaning known to a skilled artisan. The gyroscope 212 can provide outputs responsive to sensed angular velocity of the wireless sensor 102 (as affixed to the patient) with respect to three orthogonal axes corresponding to measurements of pitch, yaw, and roll (for example, see description provided above). A skilled artisan will appreciate that numerous other gyroscopes 212 can be used in the wireless sensor 102 without departing from the scope of the disclosure herein. In certain embodiments, the accelerometer 210 and gyroscope 212 can be integrated into a single hardware component which may be referred to as an inertial measurement unit (IMU). In some embodiments, the IMU can also include an embedded processor that handles, among other things, signal sampling, buffering, sensor calibration, and sensor fusion processing of the sensed inertial data. In other embodiments, the processor 202 can perform these functions. And in still other embodiments, the sensed inertial data are minimally processed by the components of the wireless sensor 102 and transmitted to an external system, such as the patient monitor 106, for further processing, thereby minimizing the complexity, power consumption, and cost of the wireless sensor 102, which may be a single-use, disposable product.

Figure 4B:
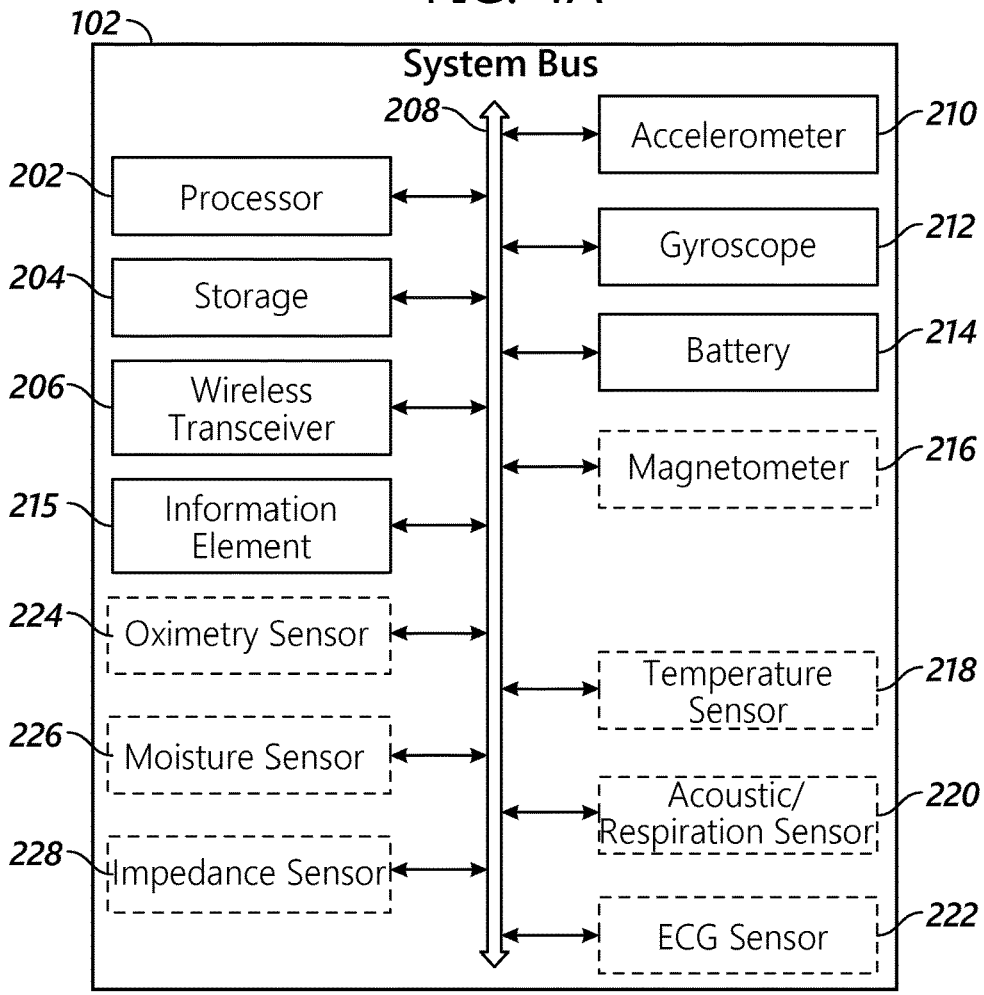
FIG. 4B is a functional block diagram of another embodiment of the wireless sensor of FIG. 1 in accordance with aspects of this disclosure.

FIG. 4B is a simplified hardware functional block diagram of an embodiment of the disclosed wireless sensor 102 that includes the following optional (as reflected by dotted lines) sensing components: a magnetometer 216 (which may also be referred to as a compass), a temperature sensor 218, an acoustic respiration sensor 220, an electrocardiogram (ECG) sensor 222, one or more oximetry sensors 224, a moisture sensor 226, and an impedance sensor 228. In some embodiments, the magnetometer 216 is a three-dimensional magnetometer that provides information indicative of magnetic fields, including the Earth's magnetic field. While depicted in FIG. 4B as separate functional elements, a skilled artisan will understand that the accelerometer 210, gyroscope 212, and magnetometer 214 can be integrated into a single hardware component such as an inertial measurement unit.

According to an embodiment, a system and method are described herein to calculate three-dimensional position and orientation of an object derived from inputs from three sensors attached to the object: an accelerometer 210 configured to measure linear acceleration along three axes; a gyroscope 212 configured to measure angular velocity around three axes; and a magnetometer 214 configured to measure the strength of a magnetic field (such as the Earth's magnetic field) along three axes. In an embodiment, the three sensors 210, 212, and 214 are attached to or contained within to the wireless sensor 102 which is affixed to the patient. According to an embodiment, the sensors 210, 212, and 214 are sampled at a rate between approximately 10 Hz and approximately 100 Hz. One skilled in the art will appreciate that the sensors 210, 212, and 214 can be sampled at different rates without deviating from the scope of the present disclosure. The sampled data from the three sensors 210, 212, and 214, which provide nine sensor inputs, can be processed to describe the patient's position and orientation in three-dimensional space. In an embodiment, the patient's position and orientation are described in terms of Euler angles as a set of rotations around a set of X-Y-Z axes of the patient (for example, three, mutually orthogonal axes).

Also illustrated in FIG. 4B is a temperature sensor 218 which may be used to measure the patient's body core temperature which is a vital sign used by clinicians to monitor and manage patient conditions. The temperature sensor 218 can include a thermocouple, a temperature-measuring device having two dissimilar conductors or semiconductors that contact each other at one or more spots. A temperature differential is experienced by the different conductors. The thermocouple produces a voltage when the contact spot differs from a reference temperature. Advantageously, thermocouples are self-powered and therefore do not require an external power source for operation. In an embodiment, the temperature sensor 218 includes a thermistor. A thermistor is a type of resistor whose resistance value varies depending on its temperature. Thermistors typically offer a high degree of precision within a limited temperature range.

The acoustic respiration sensor 220 can be used to sense vibrational motion from the patient's body (for example, the patient's chest) that are indicative of various physiologic parameters and/or conditions, including without limitation, heart rate, respiration rate, snoring, coughing, choking, wheezing, and respiratory obstruction (for example, apneic events). The ECG sensor 222 can be used to measure the patient's cardiac activity. According to an embodiment, the ECG sensor 222 includes two electrodes and a single lead. The oximetry sensor(s) 224 can be used to monitor the patient's pulse oximetry, a widely accepted noninvasive procedure for measuring the oxygen saturation level of arterial blood, an indicator of a person's oxygen supply. A typical pulse oximetry system utilizes an optical sensor clipped onto a portion of the patient's body (such as, for example, a fingertip, an ear lobe, a nostril, and the like) to measure the relative volume of oxygenated hemoglobin in pulsatile arterial blood flowing within the portion of the body being sensed. Oxygen saturation (SpO2), pulse rate, a plethysmograph waveform, perfusion index (PI), pleth variability index (PVI), methemoglobin (MetHb), carboxyhemoglobin (CoHb), total hemoglobin (tHb), glucose, and/or otherwise can be measured and monitored using the oximetry sensor(s) 224. The moisture sensor 226 can be used to determine a moisture content of the patient's skin which is a relevant clinical factor in assessing the patient's risk of forming a pressure ulcer. The impedance sensor 228 can be used to track fluid levels of the patient. For example, the impedance sensor 228 can monitor and detect edema, heart failure progression, and sepsis in the patient.

Figure 5A:
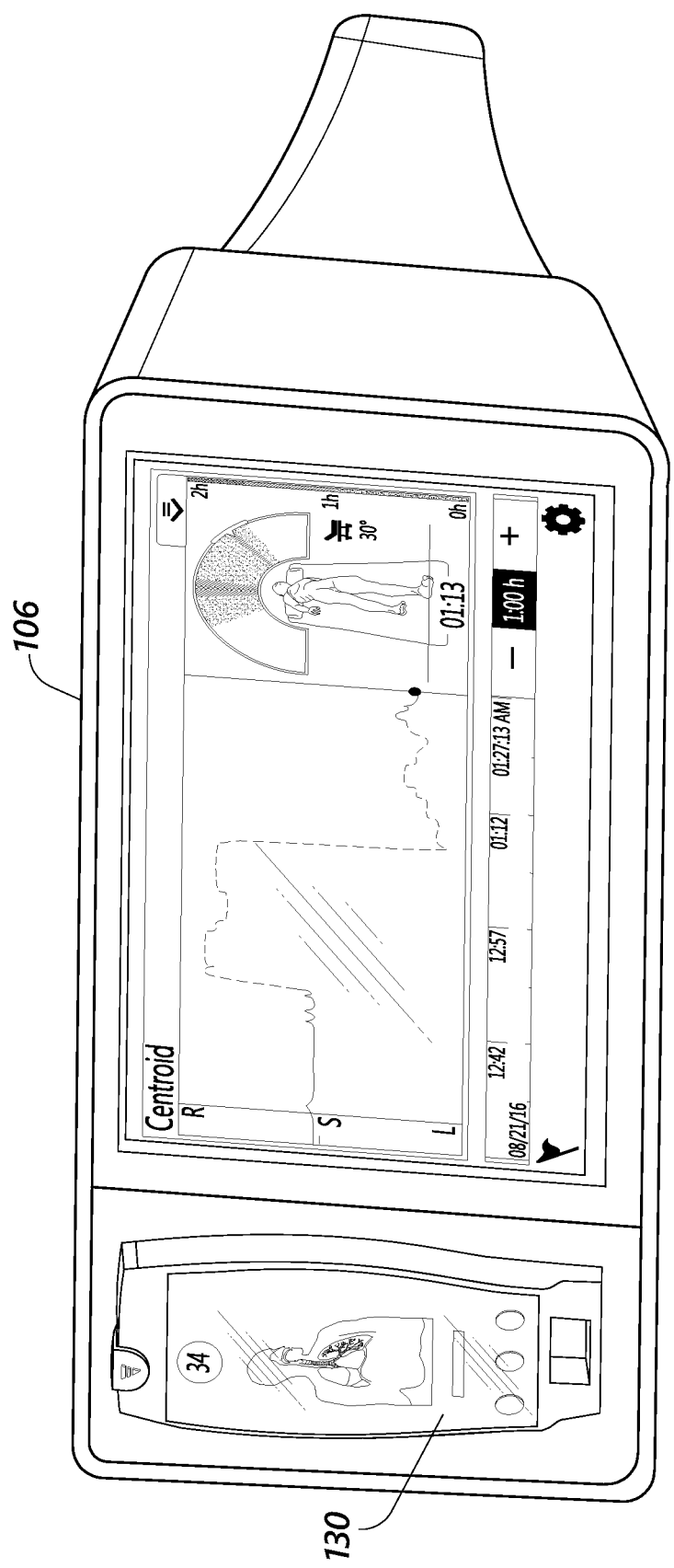
FIG. 5A illustrates an embodiment of a display of the patient monitor of FIG. 1 in accordance with aspects of this disclosure.
Figure 5B:
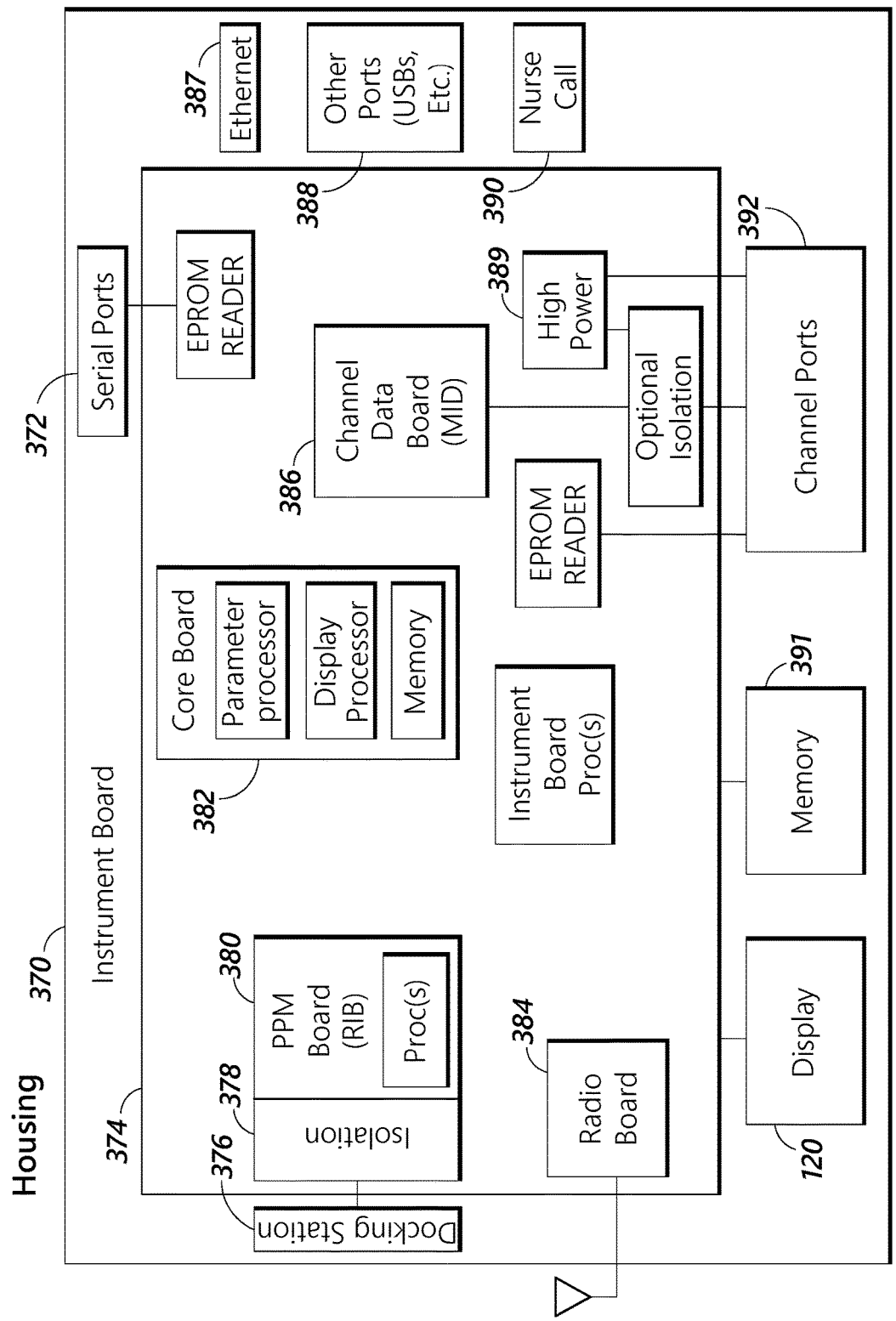
FIG. 5B is a simplified hardware block diagram of an embodiment of the patient monitor of FIG. 1 in accordance with aspects of this disclosure.

FIG. 5A illustrates an enlarged perspective view of patient monitor 106 from FIG. 1. FIG. 5B illustrates a simplified hardware block diagram of an embodiment of the patient monitor 106. As shown, the housing 370 of the patient monitor 106 can position and/or contain an instrument board 374, the display 120, a memory 391, and/or various communication connections, including the serial ports 372, the channel ports 392, Ethernet ports 387, nurse call port 390, other communication ports 388 including standard USB or the like, and/or a docking station interface 378. The instrument board 374 can include one or more substrates having communication interconnects, wiring, ports and the like to enable the communications and functions described herein, including inter-board communications. A core board 382 can include the main parameter, signal, and other processor(s) and memory. For example, the core board 382 can include a parameter processor configured to process one or more parameters, such as physiological parameters relating to the patient, one or more display processors configured to interact with and/or configure the display 120 of the patient monitor 106, and/or a memory. A portable patient monitor board ("RIB") 380 can include patient electrical isolation for the portable patient monitor 102 and one or more processors. A channel board ("MID") 386 can control the communication with the channel ports 392, including optional patient electrical isolation and/or power supply 389. A radio board 384 can include components configured for wireless communications. Additionally, the instrument board 374 may advantageously include one or more processors and controllers, buses, all manner of communication connectivity and electronics, memory, memory readers including EPROM readers, and other electronics recognizable to an artisan from the disclosure herein. Each board can include substrates for positioning and support, interconnect for communications, electronic components including controllers, logic devices, hardware/software combinations and the like to accomplish the tasks designated above and others.

An artisan will recognize from the disclosure herein that the instrument board 374 may comprise a large number of electronic components organized in a large number of ways. Using different boards such as those disclosed above advantageously provides organization and compartmentalization to the complex system.

As discussed elsewhere herein, the patient monitor 106 can keep track of the orientation of a monitored patient over time and across a plurality of orientations of the patient while in a bed (for example, a hospital bed). Methods and systems for monitoring the orientation of a patient are described in U.S. Pat. No. 10,383,527, which is incorporated by reference in its entirety. The patient monitor 106 can receive data (continuously or intermittently) from sensor 102 regarding the patient's orientation over time and can store such data in memory (such as memory 391). The patient monitor 106 can determine the time spent in each of a plurality of available orientations (for example, orientations that a patient can assume when lying on a flat surface such as a hospital bed) when the patient is in each orientation, and can store the accumulated time in such orientations in a portion of memory associated with that given orientation. For example, the patient monitor 106 can associate a timer with each of a plurality of available patient orientations and associate each of the plurality of available patient orientations with a degree of orientation (for example, left side position equals +90°) as discussed in more detail below. As such, the patient monitor 106 can keep a running log of time spent by the patient in a plurality of orientations, which can be advantageous for the purposes of following a turning protocol to avoid the development of pressure ulcers. Further, the patient monitor 106 can track time not spent in a plurality of orientations so as to provide a more holistic sense of the patient's orientation over time as discussed in more detail below. Monitoring non-consecutive durations of assumed patient orientations while also keeping track of accumulated and de-accumulated time in each of the assumed patient orientations can provide valuable information for caregivers in monitoring patients and preventing the patient from developing pressure ulcers, as also described in more detail below.

As mentioned above, the patient monitor 106 can keep a running log of time spent by the patient in a plurality of orientations to keep track of accumulated and de-accumulated time in assumed orientations. The patient monitor 106 can associate a plurality of timers with a plurality of available patient orientations. In an embodiment, the timers are implemented as counters. The patient monitor 106 can obtain data from the sensor 102 regarding the orientation of the patient, such as the degree of orientation of the patient relative to a reference point (for example, a hospital bed). Such degree of orientation can be indicative and/or representative of an angle between an axis extending normal to (for example, upward or downward from) a patient's torso or chest and an axis extending along a length and/or height of the patient (for example, the "roll" axis discussed above). Each of the plurality of timers can be associated with a degree of orientation of the patient. For example, each of the plurality of timers can be associated with a degree selected within a range between 0° and 360° or 0° and 180°, or −90° and 90°. As another example, each of the plurality of timers can be associated with a degree of orientation equal to 0°, 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or 360°, or any value therebetween, or any range bounded by any combination of these values, although values outside these values or ranges can be used in some cases. As another example, each of the plurality of timers can be associated with a degree of orientation equal to −90°, −80°, −70°, −60°, −50°, −40°, −30°, −20°, −10°, 0°, 10°, 20°, 30°, 40°, 50°, 60°, 70°, 80°, or 90°, or any value therebetween, or any range bounded by any combination of these values, although values outside these values or ranges can be used in some cases. As another example, the plurality of timers can include 180 timers, each of which are associated with a different one of the degrees from 0° to 180°. As another example, each of the plurality of timers can be associated with a degree "range," such as 0°-45°, 46°-90°, 91°-135°, 136°-180°, and/or a different range selected from any combination of the values or ranges described above.

As shown in Table 1, −90° can represent a right side position of the patient with respect to a flat plane or surface used as a reference point (such as the hospital bed). When monitoring a patient and attempting to ensure that the patient does not develop pressure ulcers, it is important to make sure the patient does not remain in a particular orientation for too long. Additionally, it is important to keep track of non-consecutive durations of assumed orientations and accumulated and de-accumulated time in assumed orientations so that a patient does not return to a previously assumed orientation before enough time has elapsed. Advantageously, the patient monitor 106 can track time spent in assumed orientations over time and allow tracked (for example, "accumulated") time in previous orientations to de-accumulate (for example, decrease) when the patient is not in those orientations.

Table 1 shows a simplified diagram/format that can be utilized by the patient monitor 106 to keep a running log of time spent in (and/or time not spent in) a plurality of orientations. While the simplified diagram contains only 5 columns and illustrates three "degree" orientations (−90°, 0°, +90°), the patient monitor 106 can generate a time log for any orientation and/or degree in between these values/orientations or beyond these values/orientations (for example, between 0°-180° or 0°-360°). As shown in the non-limiting, illustrative example of Table 1, the accumulated time in the 0° (supine) orientation—which is, as illustrated by the highlighted cells, a current orientation of the patient—is 22 minutes and 15 seconds. Exemplary Table 1 can be, for example, stored in a memory of the patient monitor 106, such as memory 391. As also illustrated in Table 1, the accumulated time in the −90° (right side) orientation is 58 minutes and 34 seconds, and the accumulated time in the 90° (left side) orientation is 20 minutes and 25 seconds.

While the accumulated time is illustrated as having a "minute" and "second" value, the accumulated time can have additionally have an "hour" value. For example, the accumulated time can be "1:20:35" representing 1 hour, 20 minutes, and 35 seconds. As discussed above, the one or more hardware processors can track the change of accumulated time in a current orientation (in Table 1, the supine position as indicated by the underlining), and also simultaneously track the change of accumulated time in all other previously-used orientations, such as the right and left side positions. While Table 1 and the foregoing discussion mentions patient orientations with respect to and/or between −90° (right side) and 90° (left side) orientations, one skilled in the art will recognize that the same disclosure is applicable to degrees and/or orientations beyond these values and/or ranges. For example, the patient monitor 106 can keep track of time spent in orientations where the patient is prone (on stomach) and/or between the prone orientation and/or the right or left side position, where orientations and degrees associated with such orientations can be between −90° (right side) and 180° (stomach), for example.

TABLE 1

| −90° (right side) | ... | 0° (supine) | ... | 90° (left side) |
|---|---|---|---|---|
| 58:34 | | 22:15 | | 20:25 |

Each of the plurality of timers associated with an orientation of the patient (such as a degree of orientation or range of degrees of the patient) can increase (for example, count up) from a value (such as zero) when the patient assumes a given orientation. For example, assuming the patient was recently placed in a hospital bed and therefore has spent no prior time in each of the plurality of orientations, each of the timers associated with one of the plurality of available orientations can have zero accumulated time. As soon as the patient assumes a particular orientation (for example, a "first orientation") among the plurality of available orientations, the patient monitor 106 can receive and process orientation data from the sensor 102 and begin tracking and storing the time spent in that particular, "first" orientation. Thus, the timer associated with that particular, first orientation can begin to increase. If and/or when the patient switches to another, "second" orientation (which can be associated with a different degree of orientation compared to the first orientation, for example), the one or more hardware processors of the patient monitor 106 can determine that such switch or change occurred based on data received from the wireless sensor 102 and determine the new orientation, and thereafter trigger a timer associated with the new, second orientation, which can then begin increasing or counting up, for example. Simultaneous to the "counting up" of the timer associated with the second orientation, the timer associated with the previous, first orientation can begin changing, for example, by decreasing downward toward zero. Further, if and/or when the patient returns to the first orientation, the timer associated with the second orientation can begin counting down simultaneous to the timer associated with the first orientation counting up. Thus, the timers associated with the plurality of patient orientations can advantageously keep track of non-consecutive durations of orientations assumed by a patient.

Keeping track of non-consecutive durations of a plurality of patient orientations and such accumulation/de-accumulation of time in assumed/non-assumed orientations advantageously provides a holistic view of time spent in the plurality of orientations. Further, keeping track of time not spent in previously-assumed orientations incorporates the concept that time not spent in a previously-assumed orientation "relieves" portions of the patient's body from pressure and allows the portions to restore in their capacity to withstand pressure without developing pressure ulcers.

The patient monitor 106 can log accumulated and/or de-accumulated time in each of a plurality of orientations (for example, degree of orientation) in relation to time limits or maximums, for example. In following a turning and/or monitoring protocol to avoid the development of pressure ulcers in patients, caregivers may have maximum time limits that a patient can be in a given orientation. For example, the maximum time that a patient can be in a given orientation can be 15 minutes, 30 minutes, 45 minutes, 1 hour, 1 hour and 15 minutes, 1 hour and 30 minutes, 1 hour and 45 minutes, or 2 hours, among other values. This maximum time limit can be the same for each of the plurality of available orientations or it may be different. For example, if a portion of the patient's body is more susceptible or vulnerable to develop pressure ulcers, a maximum time limit associated with an orientation that corresponds to that portion of the patient's body can have a smaller maximum time limit than other patient orientations. The timers associated with each of the plurality of positions can also keep track of overage time—time spent in an orientation that is beyond the maximum time limit. For example, where the maximum time limit for a given orientation is 1 hour, when the patient is in the given orientation for more than 1 hour, the timer can continue to count up to keep track of the overage time. Alternatively, the timers can stop counting up and hold steady at the maximum time limit when such limit is reached.

While the patient monitor 106 can keep track of accumulated and de-accumulated time spent in a particular orientation by having a timer associated with such orientation count up when a patient assumes the orientation and count down when the patient is not in such orientation, the patient monitor 106 can track time spent in a particular orientation in an alternative manner. For example, the patient monitor 106 can keep track of accumulated and de-accumulated time spent in a particular orientation by having a timer associated with such orientation count down when a patient assumes the orientation and count up when the patient is not in such orientation. For example, when a patient transitions to a new orientation, a timer associated with that orientation can count down from a maximum time limit. As discussed above, the maximum time limit can be any limit prescribed or predetermined by a caregiver, such as 2 hours, 1 hour, 30 minutes, among others. Thus, as the patient remains in that orientation, the timer associated with that orientation can continue to count down towards, for example, zero. The value of time in such timer therefore can show the instantaneous time "available" or left for the patient to remain in that orientation. When the patient switches to another orientation, a timer associated with the new orientation can begin to count down from a maximum time limit (which can be the same or different from the maximum time limit associated with the previous orientation) while the timer associated with the previous orientation can simultaneously count up, thus "restoring" the time available for the patient to assume that orientation. The timers associated with each of the plurality of positions can also keep track of time spent in an orientation that is beyond the maximum time limit. For example, where the maximum time limit for a given orientation is 1 hour, when the patient is in the given orientation for more than 1 hour, the timer can continue to count down past zero (for example, can show or keep track of a negative time value) to keep track of the overage time. Alternatively, the timers can stop counting down and hold steady when the maximum time limit is reached or runs out.

Regardless of whether the timers associated with each of a plurality of patient orientations count up when a patient is in a given position and count down when the patient is not in the given position, or count down when a patient is in a given position and count up when the patient is not in the given position, the patient monitor 106 can provide valuable information that can be used by a caregiver in following a patient turn protocol to prevent patients from developing pressure ulcers. As will be discussed below, such tracking of accumulated and/or de-accumulated time in various orientations can advantageously be utilized in a structured display of the patient monitor 106 in a variety of ways to provide valuable insight to caregivers, such as in providing visual or audio alarms or generating an orientation trend of the patient.

While the systems and methods of keeping track of the orientation of a patient are described above with reference to patient monitor 106, one of skill in the art will recognize that the same can be implemented by utilizing the multi-patient monitoring system 110, nurses' station systems 113, and/or other components or system.

Figure 6:
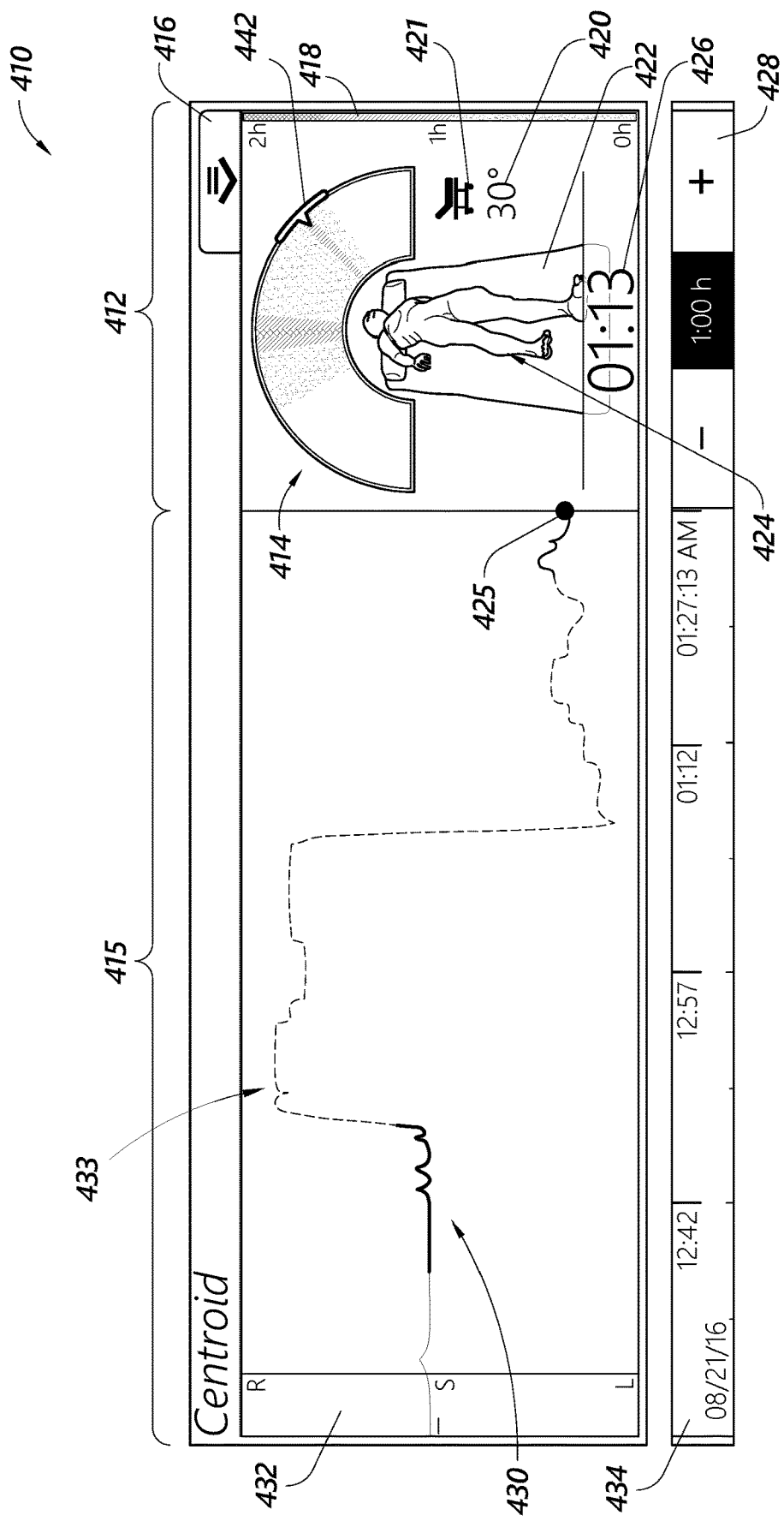
FIG. 6 illustrates an embodiment of a structured display on a display screen of a patient monitor in accordance with aspects of this disclosure.

FIG. 6 illustrates an embodiment of a structured display 410 on a display screen of patient monitor 106. The structured display 410 can include a variety of components that can provide information to a caregiver relating to the patient's orientation, position, and/or movement with respect to a hospital bed. For example, various components within the structured display 410 can provide information regarding the patient's past and present orientation (for example, degree of orientation), among other information. The structured display 410 can include a patient representation 424. Patient representation 424 and other patient representations discussed herein (e.g., 624, 724) can be any graphic used to illustrate the orientation and/or position of a patient, such as a current orientation of the patient. For example, as shown in FIG. 6, the patient representation 424 can include a model or image of a patient. The model or image of the patient can be a 3D or 2D model. While FIG. 6 illustrates a 3D model of a patient, a patient representation 424 can be a more simplistic and/or less realistic model or image, or can even be a shape or object not resembling a human patient. For example, the patient representation 424 can be a square, rectangle, among other shapes, which can rotate to illustrate an orientation of the patient. As discussed above, the patient monitor 106 can receive and process data relating to a monitored patient's orientation from a sensor attached to a patient, such as wireless sensor 102. The patient monitor 106 can include one or more hardware processors which can process such data and display the patient's orientation using a patient representation 424. As can be seen in FIG. 6, the patient representation 424 illustrates that the actual patient is currently oriented partially along its left side, more precisely, somewhere between a supine (back) position and a left side position. The patient representation 424 can be associated with and/or can illustrate a particular degree of orientation that the actual patient is assuming (e.g., currently assuming). For example, the patient representation 424 can illustrate a current orientation of the patient associated with a degree between 0° and 360°, between 0° and 180°, between −90° and 90°, among others. As another example, the patient representation 424 can illustrate a current orientation of the patient that is equal to 0°, 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or 360°, or any value therebetween, or any range bounded by any combination of these values, although values outside these values or ranges can be used in some cases. As another example, the patient representation 424 can illustrate a current orientation of the patient that is equal to −90°, −80°, −70°, −60°, −50°, −40°, −30°, −20°, −10°, 0°, 10°, 20°, 30°, 40°, 50°, 60°, 70°, 80°, or 90°, or any value therebetween, or any range bounded by any combination of these values, although values outside these values or ranges can be used in some cases. Such degrees of orientation can be indicative and/or representative of an angle between an axis extending normal to (for example, upward or downward from) a patient's torso or chest and an axis extending along a length and/or height of the patient (for example, the "roll" axis discussed above). For example, the degrees listed above can represent an angle between a normal axis extending from a patient's chest and the roll axis.

The structured display 410 can include a bed 422 proximate to the patient representation 424. The bed 422 can be a 3D or 2D model of a hospital bed, for example. The bed 422 can be located adjacent, proximate, and/or underneath the patient representation 424. The bed 422 can help provide context and/or can aid a caregiver in assessing a monitored patient's orientation with reference to the patient representation 424. For example, the bed 422 can act as a reference point to further illustrate the orientation of the patient representation 424. The bed 422 can be configured to blink or disappear if the patient monitor 106 detects that the patient is not in the hospital bed as discussed further below.

The structured display 410 can include a timer 426 configured to show the time that the patient has spent in the current orientation. Timer 426 can display the accumulated time in a given orientation when the patient is currently in the given orientation. As discussed above, the one or more hardware processors of the patient monitor 106 can associate each of a plurality of available orientations with a timer configured to keep track of accumulated and de-accumulated time spent in each of the plurality of available orientations. The current orientation of the patient is one of such plurality of available orientations. Timer 426 can display the current value of accumulated/de-accumulated time associated with one of the timers associated with one of the plurality of available orientations when the patient is currently in that orientation. Timer 426 can be configured to count up when the patient remains in an orientation or alternatively count down when the patient remains in an orientation in a similar or identical manner as that described above with reference to the timers associated with each of the plurality of patient orientations. For example, if a patient is in a first orientation for 30 minutes, switches to a second orientation for 2 minutes, and then switches back to the first orientation thereafter, the timer 426 can be configured to show the accumulated/de-accumulated time associated with the first orientation, which in such case will be 28 minutes. Once the first orientation is resumed by the patient in this example, the timer 426 can count up from 28 minutes. Alternatively, as discussed further above, the timers associated with each of the plurality of positions can be configured to count down when a patient is in a given orientation. In such alternative scenario, if the patient is in a first orientation for 30 minutes and the timer associated with the first orientation is configured to count down from 1 hour (which can be a maximum time limit for the first orientation), and the patient switches to a second orientation for 2 minutes and then back to the first orientation thereafter, the timer 426 will display 32 minutes. Regardless of whether the timers for each of the plurality of orientations and the timer 426 is configured to count up or down when the patient is in a given orientation, the timer 426 can advantageously display an accumulated/de-accumulated time value associated with assumed patient orientations and therefore greatly assist a caregiver in monitoring a patient's orientation and following a turn protocol.

Timer 426 can display the current value of the accumulated/de-accumulated time of the orientation with hour, minute, and/or second values. For example, as shown in FIG. 6, "01:13" can represent that the accumulated time the patient has been in a given orientation is 1 minute and 13 seconds. Additionally or alternatively, timer 426 can display a value such as "01:03:30" representing that the accumulated time the patient has been in an orientation is 1 hour, 3 minutes, and 30 seconds. One of skill in the art can recognize a variety of ways to display the accumulated time the patient has been in an orientation with timer 426.

Timer 426 can alert a caregiver when a patient has exceeded a maximum time limit in a given orientation. For example, if the patient has been in a given orientation for more than the maximum time limit, the timer 426 can be configured to blink at different speeds. Additionally or alternatively, if the patient has been in a given orientation for more than the maximum time limit, the timer 426 can be configured to change in color. For example, the timer 426 can display the current time in red when the patient has been in a given orientation for a time greater than the maximum time limit. Additionally or alternatively, if the patient has been in a given orientation for more than the maximum time limit, the timer 426 can be configured to change in size. For example, as shown in FIG. 6, the time display ("01:13") can increase in size (for example, font size) if the patient has been in a given orientation for more than the maximum time limit. Thus, the timer 426 can be configured to alert a caregiver when a patient has exceeded a maximum time limit in a given orientation. Such alerts of the timer 426 can operate independently or in combination with other alerts of the patient monitor 106 such as the visual and/or audio alerts discussed elsewhere herein. While the timer 426 is shown in FIG. 6 as appearing below the patient representation 424, timer 426 can be displayed in a variety of locations within the structured display 410.

The structured display 410 can include a patient inclination indicator 421 and/or a patient inclination degree indicator 420. The patient inclination indicator 421 can be configured to display an inclination of a hospital bed and/or a patient within the hospital bed. Further, the patient inclination degree indicator 420 can display the degree of inclination of the patient in or with respect to the hospital bed. For example, if the patient is laying inclined at a degree of 30° with respect to a flat plane (such as a lower portion of the hospital bed), the patient inclination indicator 421 can visually depict such inclination by showing an upper portion of a hospital bed inclined with respect to a lower portion of the hospital bed and/or the patient inclination degree indictor can visually display "30°" as illustrated in FIG. 6.

As discussed in more detail above, the one or more hardware processors of patient monitor 106 can be configured to log accumulated and/or de-accumulated time in each of a plurality of orientations in relation to time limits or maximums. In following a turning and/or monitoring protocol to avoid the formation of pressure ulcers in patients, caregivers may have maximum time limits that a patient can be in a given orientation. For example, the maximum permissible time a patient should be in a given orientation can be selected by a caregiver to be 30 minutes, 1 hour, or 2 hours, among other values. The patient monitor 106 can incorporate maximum limit adjuster which can allow a caregiver or user to select an appropriate time limit by which an alert can be triggered when the patient's accumulated time in a given orientation exceeds the time limit. The alerts that can be triggered in such situations can be any of the alerts discussed herein.

As discussed above, the patient monitor 106 can include one or more hardware processors that receive output signals from sensor 102 attached to the patient and process the output signals to determine information relating to the patient's orientation in, for example, a hospital bed. The one or more hardware processors can generate structured display 410 on a display screen of the patient monitor 106 which can include an orientation trend of a patient in a bed. The orientation trend can contain and/or illustrate information related to the patient's orientation. Further, this orientation trend can be associated with the plurality of timers—which are themselves associated with available orientations of the patient in a bed—that are configured to account for non-consecutive durations of the patient in one or more of the available orientations. The orientation trend can display (for example, illustrate) the accumulated/de-accumulated time of the patient in various orientations in a convenient and simple manner so that caregivers can quickly assess the orientation history of a patient and determine whether the patient is likely to develop a pressure ulcer or needs to be rotated and/or moved.

The orientation trend of the structured display 410 can include a heat map 414 configured to graphically illustrate the accumulated/de-accumulated time of the patient in a variety of orientations. The shape and/or structure of the heat map 414 can coincide and/or correspond with the plurality of available orientations discussed above. For example, the heat map 414 can be made up of a plurality of lines where each of the lines represent a degree of orientation of the patient in a hospital bed. As discussed above, the one or more hardware processors can keep track of the accumulated/de-accumulated time of a patient in a plurality of orientations. The one or more hardware processors can incorporate this information into the heat map 414 by varying a contrast of the heat map 414 as the accumulated/de-accumulated time of the patient in a given orientation increases and/or decreases. For example, the one or more hardware processors can keep a log of the patient's accumulated/de-accumulated time in a given orientation and vary a color of one of the plurality of lines of the heat map 414 that is associated with that given orientation. Each of the plurality of lines and/or plurality of orientations can be associated with a degree of orientation of the patient in and/or with respect to a flat plane (for example, a bed). For example, each of the plurality of lines can be associated with a degree of orientation available to the patient that is equal to 0°, 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or 360°, or any value therebetween, or any range bounded by any combination of these values, although values outside these values or ranges can be used in some cases. As another example, each of the plurality of lines can be associated with a degree of orientation available to the patient that is equal to −90°, −80°, −70°, −60°, −50°, −40°, −30°, −20°, −10°, 0°, 10°, 20°, 30°, 40°, 50°, 60°, 70°, 80°, or 90°, or any value therebetween, or any range bounded by any combination of these values, although values outside these values or ranges can be used in some cases. The above-listed degrees of orientation can be indicative and/or representative of an angle between an axis extending normal to (for example, upward or downward from) a patient's torso or chest and an axis extending along a length and/or height of the patient (for example, the "roll" axis discussed above). For example, the degrees listed above can represent an angle between a normal axis extending from a patient's chest and the roll axis.

With reference to FIG. 6, one end of the heat map 414 (left end) and/or a line located at such end can be associated with a right side orientation of the patient, which can be associated with a −90° orientation, for example. The other end of the heat map 414 (right end) and/or a line located at such end can be associated with a left side orientation of the patient, which can be associated with a +90° orientation, for example. A middle position, region, or line of the heat map 414 can be associated with a supine (back) position of the patient, which can be associated with a 0° orientation. Additionally, between these three degree orientations, there can be a plurality of lines which can each be associated with a given degree of orientation of the patient in the bed. Regardless of the precise thickness, angle, length, and/or other properties of such lines, however, each of these lines can be associated with an orientation of the patient (e.g., a degree of orientation) and can be linked or otherwise associated with each of the plurality of available orientations discussed above.

Based on the accumulated/de-accumulated time of the patient in the plurality of available positions as monitored by the plurality of timers, the one or more hardware processors can vary a contrast of the plurality of lines in the heat map 414. The structured display 410 of FIG. 6 illustrates how the one or more hardware processors can vary the contrast of the heat map 414 based on such information. FIG. 8A shows a close up view of heat map 414 from FIG. 6. As shown in FIG. 8A, heat map 414 can include a first region 438 and a second region 440. As discussed above, the heat map 414 can be made up of a plurality of lines associated with a plurality of available orientations of the patient. The first and second regions 438, 440 can thus contain some of these plurality of lines. The first region 438 can represent orientations that the patient has assumed, for example, in a recent timeframe (e.g., a 2 hour period). More specifically, the first region 438 can represent orientations of the patient where the accumulated time in each of the orientations is greater than zero and has not "counted down" to zero, or, as discussed above, "counted up" (restored back) to some value. For example, where the plurality of timers associated with available orientations of the patient are configured to count up when the patient is in a given orientation and count down when the patient is not in such orientation, the first region 438 can represent that the patient still has accumulated time in these orientations. The second region(s) 440 can represent some of the plurality of lines/available orientation that patient has not been in over a recent time range (e.g., 2 hours) and/or orientations where the patient has no accumulated time. Thus, by examining the first region 438 in heat map 414, a caregiver can determine that certain portions of the patient's body have recently experienced some level of contact and/or pressure. For example, in the exemplary illustration of FIGS. 6 and 8A, a caregiver can determine that, based on the varied contrast of the lines forming heat map 414, the patient's back has been subject to more pressure than some other portions of the patient's body.

As discussed above and shown in FIGS. 6 and 8A (among others), the plurality of lines contained within the first region 438 can be varied in contrast according to how much and/or how little accumulated/de-accumulated time is associated with these lines. For example, the one or more hardware processors can be configured to shade and/or hatch lines in heat map 414 associated with orientations having more accumulated time with a darker shade, more shading, and/or with more hatching, than lines associated with orientations which have less accumulated time. As can be seen in at least FIG. 8A, hatching in a middle region of heat map 414 can indicate that the patient has more accumulated time in orientations at and/or near a supine (back) orientation, whereas the sparse dotting outside this middle region may indicate that the patient has spent some, but little or less time in orientations outside this range. Further, the lack of shading and/or hatching at and proximate to the left and right ends of the heat map 414 may indicate that the patient has no accumulated time in orientations at and near to the left side orientation (+90 degrees) and right side orientation (−90 degrees). Advantageously, the lack of shading and/or hatching in these areas can quickly indicate to a caregiver that these positions are not only available orientations for the patient to be turned to, but that they are likely to be "safe" and/or suggested orientations, because the patient has spent no recent time there (thus the chances of developing a pressure ulcer from being placed in that orientation are low or negligible for at least the near future).

The varying of contrast discussed above can be, for example, varying of color of one or more of the plurality of lines of the heat map 414. For example, based on the accumulated/de-accumulated time of the patient in the plurality of available positions as monitored by the plurality of timers, the one or more hardware processors can vary the color plurality of lines associated with the plurality of available positions and plurality of timers. The one or more hardware processors can vary the color of the plurality of lines based on a color spectrum. For example, the one or more hardware processors can vary the color of one or more of the plurality of lines between purple or blue to red, and/or vary the color based on a wavelength range, such as from 380-450 nm (representing approximate violet/purple wavelength range) to 625-750 nm (representing approximate red wavelength range). The one or more hardware processors can vary the color of the one or more of the plurality of lines from green (at or near a wavelength of 520-560 nm) to red. For example, the color of one or more of the plurality of lines can be green when the patient has some minimum accumulated time in an orientation but less than a first threshold, and the color can be varied from green to red as the patient's time in such orientation increases. For example, after the accumulated time the patient has been in a given orientation increases beyond the first threshold, the color of a line associated with that orientation can increase in wavelength from a wavelength associated with the color green to a wavelength associated with the color red). When the color is red, such color can indicate that the patient has accumulated time in the orientation at and/or greater than a second threshold (for example, a maximum time limit or threshold). The minimum accumulated time in the orientation sufficient to trigger a green color designation can be, for example, 5 seconds, 2 seconds, 1 second, or some other value. The first threshold can be, for example 30 minutes, 20 minutes, 10 minutes, 5 minutes, or some other value. The second threshold can be similar and/or identical to the maximum time limit that can be preset and/or predetermined by a caregiver and which is discussed further above. The structured display 410 can include a color legend 418 (see FIG. 6), which can include a range of utilized colors/wavelengths and reference time markers proximate to the legend (e.g., "2 h", "1 h", "0 h") to provide the caregiver guidance as to what the varying colors mean.

Utilization of a color spectrum associated with accumulated time of a patient in orientations in the heat map 414 of structured display 410 can be significantly advantageous for caregivers. Caregivers monitor a great number of patients in clinical environments, and such monitoring involves keeping track of a large number of patient parameters and other data. Further, caregivers often employ multiple devices for monitoring such patients and patient parameters. The ability of the caregiver to simply glance at the heat map 414 and instantly obtain a holistic sense of the patient's recent orientation history and condition gives the caregiver a realistic opportunity to prevent and/or treat potentially life-threatening pressure ulcers.

Advantageously, the heat map 414 can include an indicator 442 (see FIGS. 6-8D) which can identify a current orientation of the patient. The indicator 442 can be positioned along a border 436 of the heat map 414, and can slide or otherwise move depending on the current orientation of the patient. This indicator 442 can be linked to one of the plurality of orientations whose associated timer is currently "counting up" or "counting down", as discussed above. Further, the indicator 442 can include a pointer which can point to one of the plurality of lines within the heat map 414 which is associated with the current orientation of the patient. While the indicator 442 is shown as positioned on the border 436 of the heat map 414 and can slide along the border 436 in accordance with the patient's variable orientation, the indicator 442 can be shaped and/or otherwise positioned in a different portion of the heat map 414. For example, the indicator 442 could represent a dot or short line and could be positioned within an interior of the heat map 414.

Figure 7:
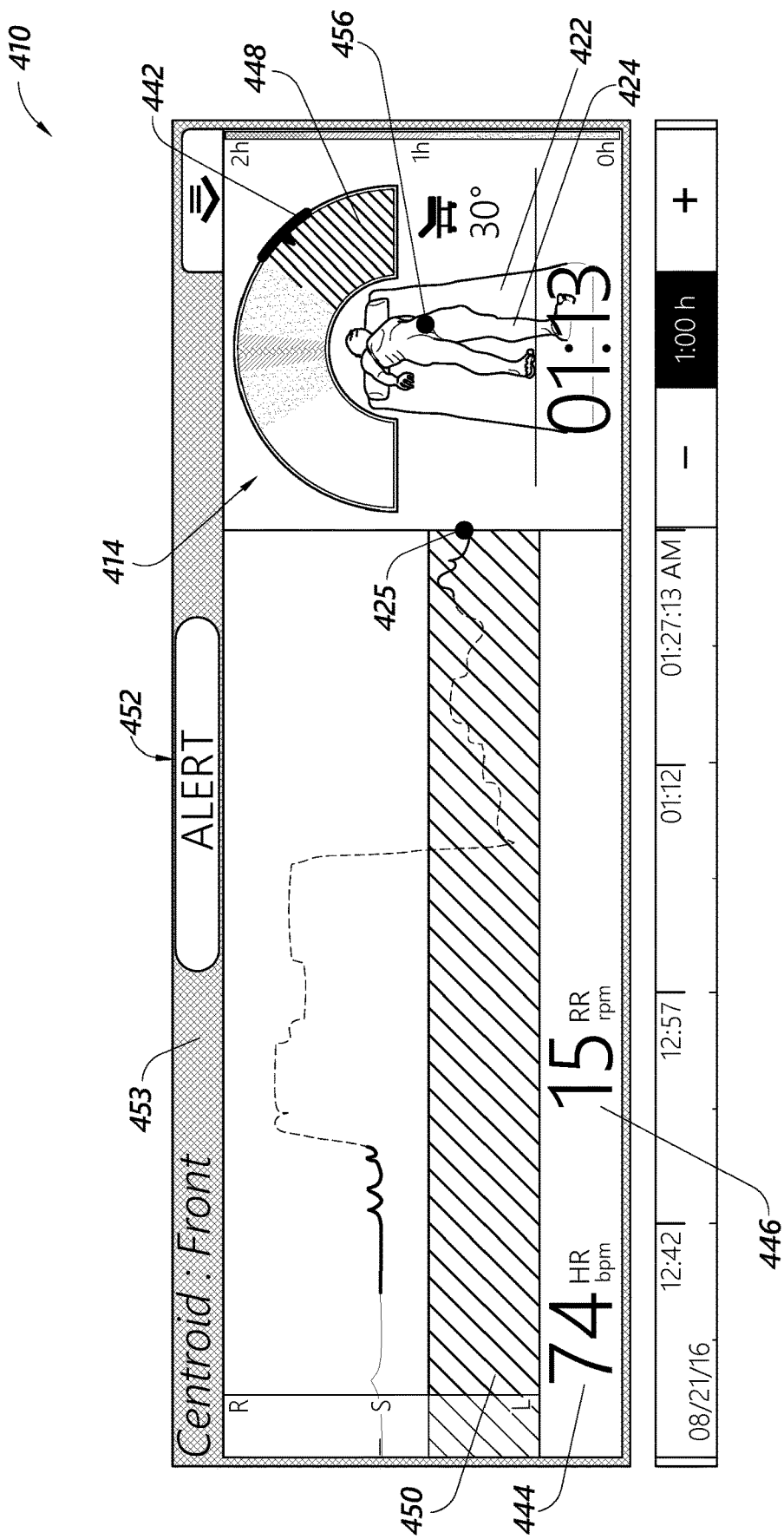
FIG. 7 illustrates an embodiment of a structured display on a display screen of a patient monitor in accordance with aspects of this disclosure.
Figure 8D:
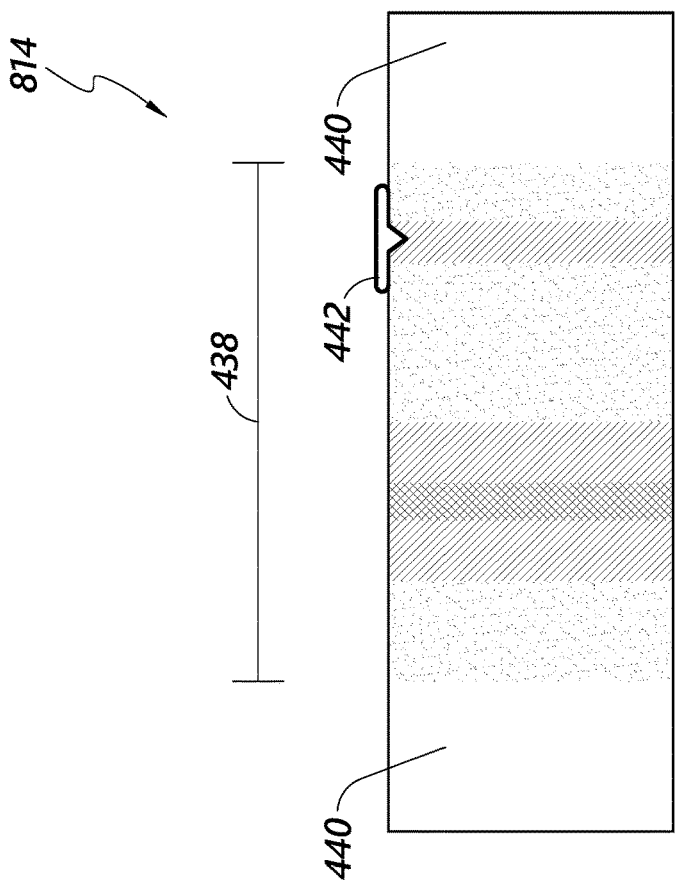
Figure 8C:
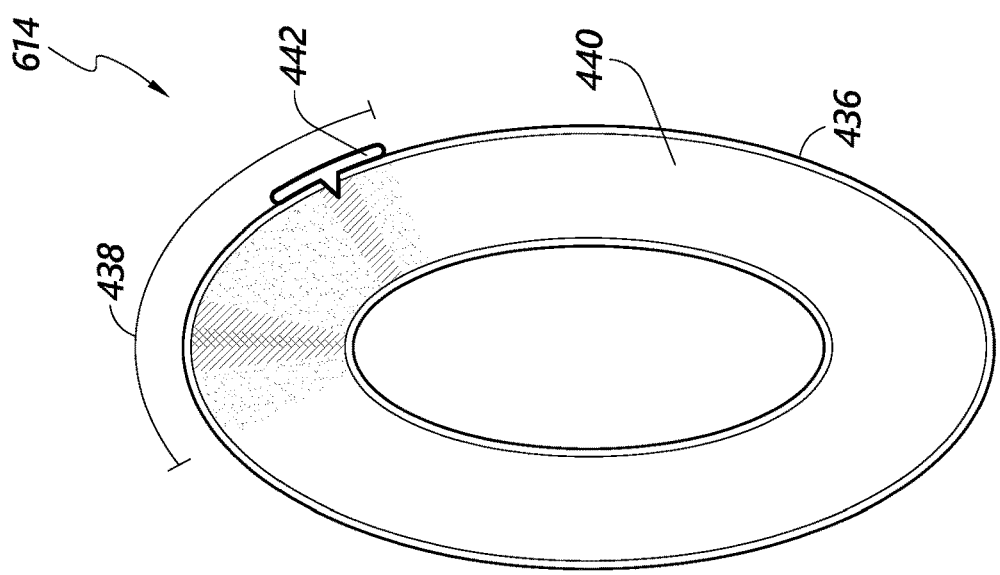

While FIGS. 6, 7, and 8A, illustrate a heat map 414 having an arch-shaped interior region, the heat map 414 can have a variety of other shapes and/or designs, yet still have all the features described above. For example, as shown in FIGS. 8B, 8C, 8D, and 9A, the heat maps 514, 614, 814, and 714 can have a circle shape, ellipse shape, box shape (e.g., rectangular), and/or half-circle shape, among other shapes. Each of the heat maps 514, 614, 714, and 814 can have any or all the features described above with respect to heat map 414.

In addition or as an alternative to the heat map 414, 514, 614, 714, 814, the orientation trend of the structured display 410 can include an orientation graph 433. The orientation graph 433 can illustrate a history of the patient's orientation over a recent time range. The orientation graph 433 can include a first axis, which can be a position axis 432, and a second axis, which can be a time axis 434. The position axis 432 can include one or more markers indicative of patient orientations or positions. For example, the position axis 432 can include one, two, three, four, five, six, seven, or eight or more markers indicative of patient orientations or positions. As shown in FIG. 6, the position axis 432 includes three markers, each associated with one of a right side orientation, left side orientation, and supine (back) orientation of the patient. The one or more markers can act as a reference point by which data and/or information in the orientation graph 433 can be measured against. Instead of and/or in addition to showing right, left, and/or supine position markers on position axis 432, the position axis 432 can include markers showing one or more orientation degrees, which can be utilized as reference points for data appearing in the orientation graph. For example, instead of displaying "R", "S", and "L" on the position axis 432 as shown in FIG. 6, these markers could be labeled as "−90°", "0°", and "+90°", and/or other degree values. Further, more markers can be included in between these values. For example, the position axis 432 can include markers at every 5, 10, 15, 20, 25, 30, 35 or 45 degree interval. Regardless of the precise number and/or position of the markers, such markers can be a useful tool for a caregiver to quickly compare data from the orientation graph 433 to the markers for reference purposes.

The time axis 434 can display one or more markers (such as one, two, three, four, five, six, seven, or eight or more markers) which can, similar to markers in the position axis 432, act as a reference point for data appearing in the orientation graph 433. Advantageously, the amount and/or position of the one or more markers of the time axis 434 can correspond with a time range which can appear in and/or be adjusted by time range adjuster 428. For example, where the time range is selected to be 1:00 hour using the range adjuster 428, the time axis 434 can be configured to display a 1 hour recent time range and/or can designate one or more markers spaced equally or unequally along this 1 hour recent time range on the time axis 434. The range adjuster 428 can allow a caregiver to increase the time range and/or decrease the time range using buttons or icons, which can be "+" or "−" icons as shown in FIG. 6. As shown in FIG. 6, the time range can be set at 1:00 hour. However, the time range can be adjusted to other values using range adjuster 428.

As discussed above, monitoring of the patient and/or orientation of the patient by the patient monitor 106 and the sensor 102 can be intermittent or continuous. Where the monitoring is continuous, the recent time range (defined by the time axis 434 of orientation graph 433) can be continuously updated to follow the current time. As the patient is continuously monitored, data regarding the patient's current orientation—represented in the orientation graph 433 with orientation data point 425—can be measured, processed, and plotted within the orientation graph 433, and the recent time range of the time axis 434 tracks along with such plotting. Thus, the patient's orientation over the recent time defined by the time axis 434 provides a reference by which newly measured orientation data can be measured and/or compared against.

As discussed above, the position axis 432 and/or the time axis 434 of the orientation graph 433 can act as a reference by which data regarding the patient's orientation can be compared, for example, by a caregiver. As orientation data is received by the patient monitor 106 from the sensor 102, such data can be associated with time and orientation values and is plotted in the orientation graph 433. Such data can be continuously plotted as a continuous line in the orientation graph 433, as shown in FIG. 6. Such data can be the same as the data used for purposes of the heat map 414, 514, 614, 714, 814. For example, orientation data processed by the one or more hardware processors of the patient monitor 106 from the sensor 102 can be associated with a plurality of available positions and a plurality of timers which can keep track of the accumulated/de-accumulated time of the patient in various orientations. The one or more hardware processors can also keep a record of the orientations of the patient over time, for example, by recording the orientation at continuous and/or intermittent time stamps. Such data can be utilized to generate the plot line 430.

Advantageously, the plot line 430 in the orientation graph can vary in contrast according to accumulated time in a given orientation. Based on the accumulated/de-accumulated time of the patient in one or more of the plurality of available positions as monitored by the plurality of timers, the one or more hardware processors can vary the contrast of the plot line 430. The orientation graph 433 of the structured display 410 of FIG. 6 illustrates how the one or more hardware processors can vary the contrast or style of the plot line 430 based on processed data discussed above. As can be seen in the plot line 430 of FIG. 6, a first portion of the plot line (on the far left of the graph) is solid, followed by a bolded line, followed by a dotted line, followed by another bolded line. The bolded lines may represent a greater time in a given orientation than the dotted and/or solid portions of the plot line 430. The varying of contrast of the plot line 430 can be, for example, varying of color of data points of the plot line 430. For example, based on the accumulated/de-accumulated time of the patient in the plurality of available positions as monitored by the plurality of timers, the one or more hardware processors can vary the color of the data points of the plot line 430 associated with the plurality of available positions and plurality of timers. The one or more hardware processors can vary the color of the data points based on a color spectrum. For example, the one or more hardware processors can vary the color of the data points between purple or blue to red, and/or vary the color based on a wavelength range, such as from 380-450 nm (representing violet/purple wavelength) to 625-750 nm (representing red wavelength.

As another example, the one or more hardware processors can vary the color of the data points in the orientation graph 433 from green (at or near a wavelength of 520-560 nm) to red. For example, the color of the data points can be green when the patient has some minimum accumulated time in an orientation but less than a first threshold, and the color can be varied from green to red as the patient's time in such orientation increases. For example, after the accumulated time the patient has been in a given orientation increases beyond the first threshold, the color of a data point or a set of data points associated with and/or near such orientation can increase in wavelength from a wavelength associated with the color green to a wavelength associated with the color red. When the color is red, such color can indicate that the patient has accumulated time in the orientation at and/or greater than a second threshold (for example, a maximum time limit or threshold). The minimum accumulated time in the orientation sufficient to trigger the green color designation can be, for example, 5 seconds, 2 seconds, 1 second, or some other value. The first threshold can be, for example 30 minutes, 20 minutes, 10 minutes, 5 minutes, or some other value. The second threshold can be similar and/or identical to the maximum time limit that can be preset and/or predetermined by a caregiver and which is discussed further above. The structured display 410 can include a color legend 418, which can include a range of utilized colors/wavelengths and reference time markers proximate to the legend (e.g., "2 h", "1 h", "0 h") to provide the caregiver with guidance as to what the varying colors mean. Utilization of a color spectrum associated with accumulated time in orientations in the plot line 430 of structured display 410 can be significantly advantageous for caregivers. Caregivers monitor a great number of patients in clinical environments, and such monitoring involves keeping track of a high number of patient parameters and other data. Further, caregivers often employ multiple devices for monitoring such patients and patient parameters. The ability of the caregiver to simply glance at the plot line 430 and instantly obtain a holistic sense of the patient's recent orientation history and condition gives the caregiver a realistic opportunity to prevent and/or treat potentially life-threatening pressure ulcers.

Additionally, the orientation graph 433 can provide other valuable information to the caregiver regarding the patient's wellbeing and condition. For example, the variability in shape of the plot line 430 can provide information to the caregiver regarding the patient's movement and/or rotation, and can also provide insight into what orientations the patient prefers or does not prefer, especially since the orientation graph 433 can display the orientation history over a variable time range. For example, if the time axis 434 is configured to display the patient's orientation history over a 4-hour time range, the caregiver may be able to asses a wider range of the patient's orientation and/or preference/lack of preference for a given position. Such information can be helpful to a caregiver, for example, in determining if there are other afflictions and/or conditions affecting the patient. For example, if analysis of the orientation graph over a wide time range reveals that the patient never assumes a 45° degree orientation, the patient may have an injury or other issue on a portion of its body that would be pressured if the patient assumed such orientation. As another example, a high degree of fluctuations in the plot line 430 as displayed in the orientation graph 433 may be indicative of conditions such as seizures, falls, pain/discomfort, or other conditions or events, especially if such fluctuations occur in a high frequency over a small time range. In some embodiments, the one or more hardware processors can determine whether the patient's orientation has changed more than a threshold amount of a given time period, and can issue an alarm, alert, and/or notification if such scenario occurs. For example, the one or more hardware processors can determine whether the patient has not maintained a given orientation (for example, degree of orientation or degree range) for more than a threshold time (for example, 5 seconds) over a 10 minute time period, and issue an alarm, alert, and/or notification if such scenario occurs. Thus, the orientation graph can advantageously provide valuable insight to a caregiver regarding the patient's wellbeing and/or conditions affecting the patient.

The orientation graph 433 and heat map 414, 514, 614, 714, 814 can be generated alone or in combination with each other in structured display 410. Where the structured display includes both, each can be partitioned into a different area of the structured display 410. For example, the orientation graph 433 can be partitioned into a first portion 415 of structured display 410 and the heat map(s) 414, 514, 614, 714, 814 can be partitioned into a second portion 412 of structured display 410. Where both are shown and partitioned in the structured display 410, the first portion 415 can be larger than the second portion 412, which can give the orientation graph more real estate so as to allow for larger time ranges to be displayed (and thus a larger history of the patient's orientation). Advantageously, the orientation graph and the heat map 414, 514, 614, 714, 814 can work in tandem with one another, and as discussed above, can be generated based on the same data received and processed by the hardware processors of the patient monitor 106.

The structured display 410 can include a drop down bar 416 which can provide various functionality. For example, drop down bar 416 can allow a user or caregiver to place the patient monitor 106 and/or the sensor 102 coupled to the patient monitor 106 in a stand-by mode, which will temporarily stop the transmission and/or reception of data from the sensor 102 to the patient monitor 106 and/or stop analysis of data from the sensor 102. Drop down bar 416 can also allow a user or caregiver to replace or switch the sensor 102 with another sensor, by breaking the pairing or communication between the sensor 102 and pairing with another sensor. Such pairing is described further in U.S. Pat. No. 10,383,527, which is incorporated by reference in its entirety.

The orientation graph 433 and/or heat map 414, 514, 614, 714, 814 of structured display 410 can include features that illustrate orientations that are pre-determined (e.g., by a caregiver) as un-allowed. Caregivers may desire to limit or prevent the patient from utilizing a particular orientation for a variety of reasons. Such reasons may include avoiding pressure on an injury point 456 caused by surgery or a wound and/or or may include trying to force the patient to utilize un-preferred orientations (see FIG. 7). Such un-allowed orientations can be displayed to the caregiver by displaying region 448 within the heat map 414, 514, 614,

714, 814 and/or by displaying region 450 within the orientation graph 433. Region 448 and/or region 450 can be displayed within heat map 414, 514, 614, 714, 814 and/or orientation graph 433 using the techniques described above with reference to shading, hatching, and/or varying the color of one or more of a plurality of lines within the heat map(s) and/or data points of the orientation graph 433 associated with one or more orientations. As shown in FIG. 7, regions 448, 450 can be hatched with a bold line so as to stand out from other features of the structured display 410. The patient monitor 106 can be configured to generate an alert if the patient rotates to or is assuming an orientation that falls within regions 448, 450 (which can be defined by one or more degrees or degree ranges), and is thus deemed un-allowed. For example, the structured display 410 can be configured to display a visual alert 452 when such situation occurs. Such visual alert 452 may include varying the contrast of a portion of the structured display 410, as exemplified by the change in shading/hatching of border 453. The indicator 442 can also be configured to change contrast when the patient rotates to or is assuming an orientation that is un-allowed, as shown in FIG. 7. The structured display 410 can additionally or alternatively be configured to display an alert message or notification to the caregiver, as shown by notification 452 in FIGS. 7 and 11 ("ALERT"). Incorporation of the un-allowed regions 448, 450 and/or the visual alert 452 can advantageously assist caregivers in preventing further injury to the patient which can occur in typical orientation management and monitoring techniques in clinical settings.

As shown by FIG. 7, the structured display 410 can include other patient parameter or information, such as heart rate information 444 and/or respiratory rate information 446.

Figure 11:
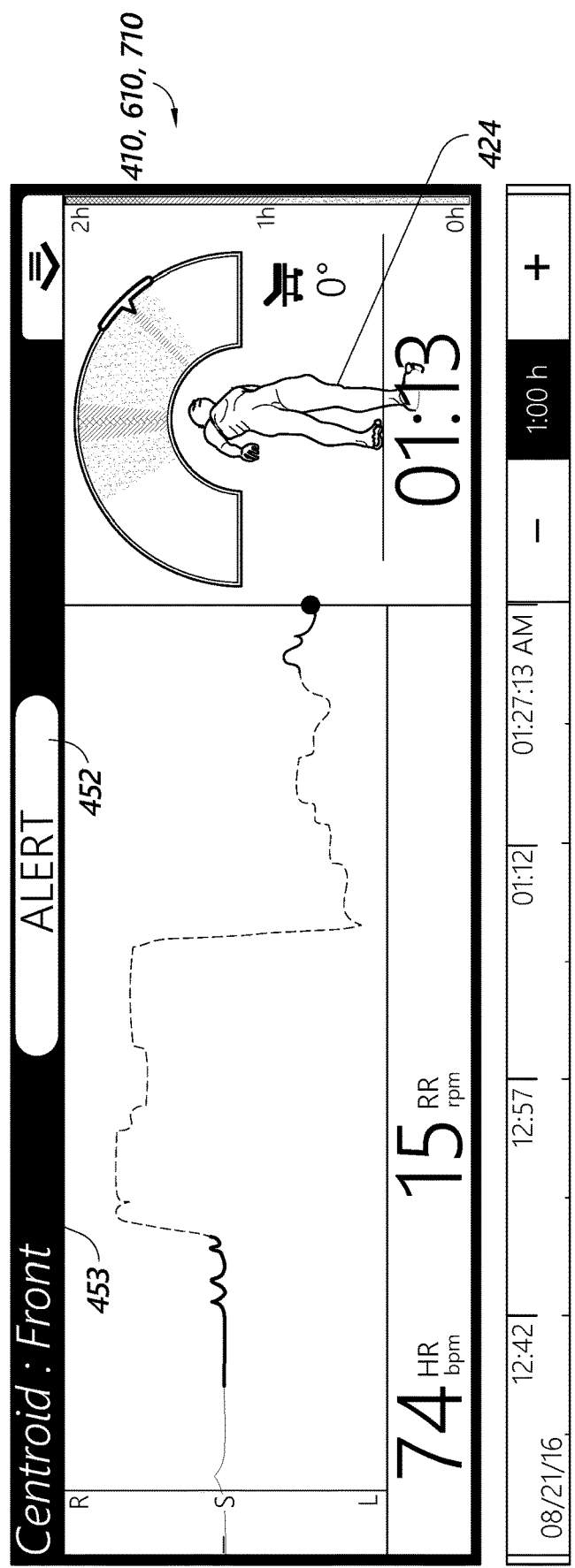
FIG. 11 illustrates an embodiment of a structured display on a display screen of patient monitor in accordance with aspects of this disclosure.

As discussed above, structured display 410 can include a model or image of a bed 422 underneath a patient representation 424. As illustrated in FIG. 11, structured display 410, 610, 710 can be configured to display a visual alert 452 when the sensor 102 and/or patient monitor 106 detects that the patient is not in the bed and/or has fallen out of the bed. Techniques and/or systems for determining fall detection are described in U.S. Pat. No. 10,383,527, which is incorporated by reference in its entirety. When the sensor 102 and/or patient monitor 106 detects that the patient is not in the bed and/or has fallen out of the bed, the structured display 410, 610, 710 can be configured to not show the bed 422 underneath the patient representation 424 or can cause the bed 422 to blink, which can notify a caregiver of the incident. Alternatively and/or additionally, such situation can trigger visual alerts 452 as discussed above with reference to FIG. 7.

Figure 9A:
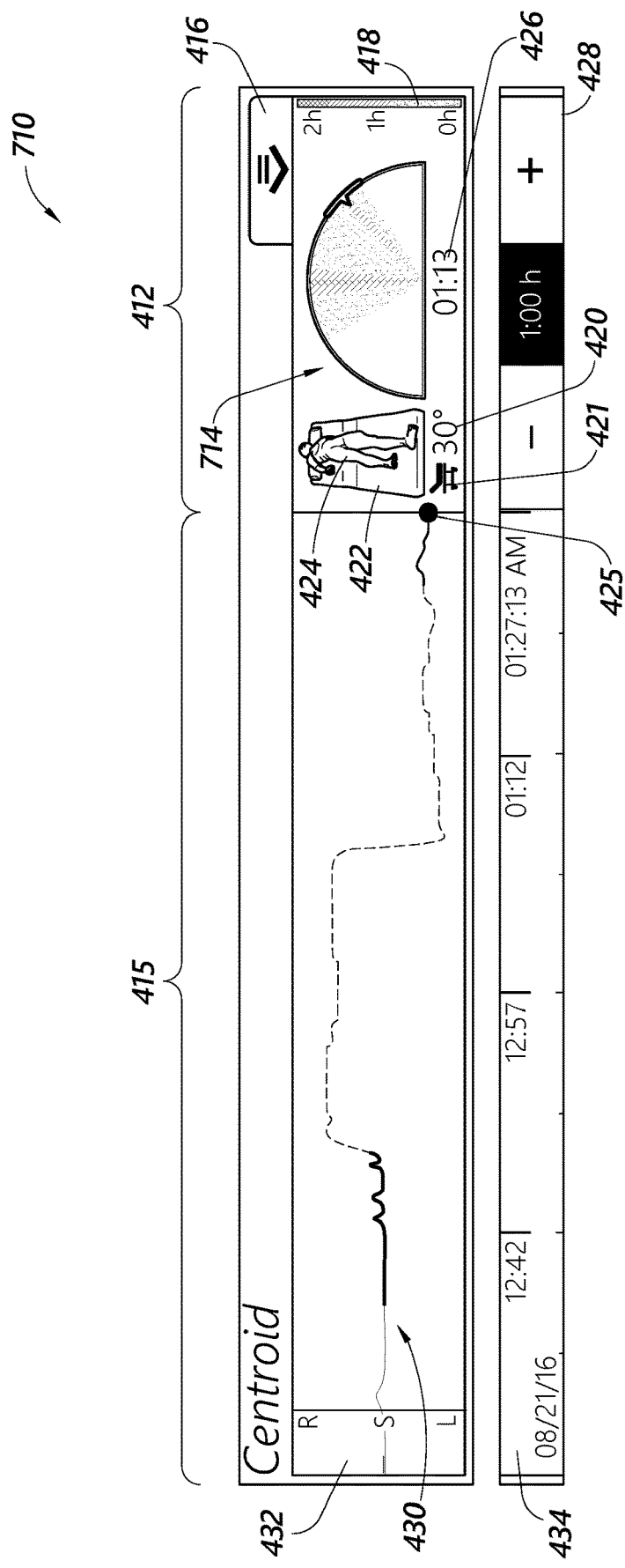
FIG. 9A illustrates an embodiment of a structured display on a display screen of a patient monitor in accordance with aspects of this disclosure.
Figure 9B:
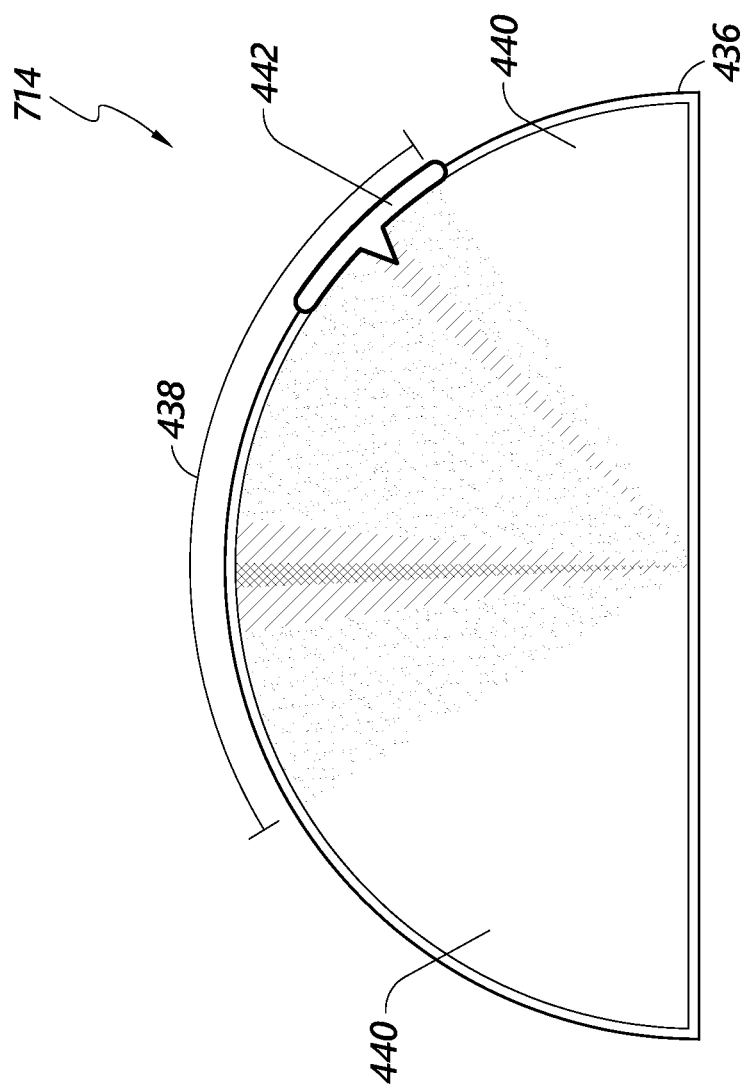
FIG. 9B illustrates an embodiment of a heat map of the structured display of FIG. 9A in accordance with aspects of this disclosure.

FIG. 9A illustrates another embodiment of a structured display 710 on a display screen of patient monitor 106. Structured display 710 is the same as structured display 410 in every way except with respect to the overall size and shape of the heat map 714. As shown, the patient representation 424 is placed to the left of the heat map 714. This allows the structured display 710 to have a smaller height than structured display 410, which can be advantageous where structured display 710 is combined with other displays on a display screen of patient monitor 106 (see, for example, FIG. 18). As discussed above, heat map 714 has all the features described with respect to heat map 414 except that heat map 714 has a half-circle shape. FIG. 9B shows an enlarged view of heat map 714.

Figure 10:
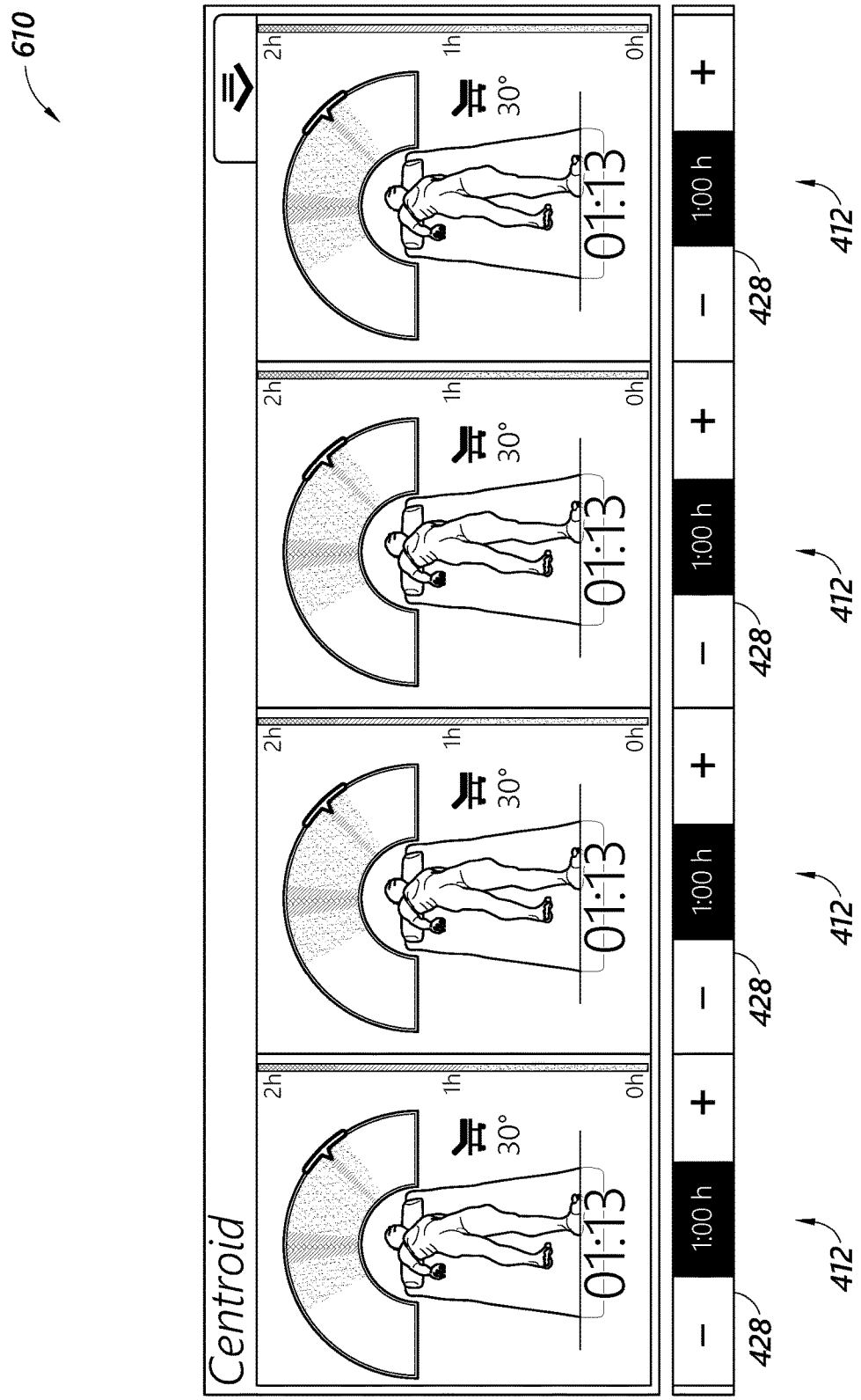
FIG. 10 illustrates an embodiment of a structured display on a display screen of a patient monitor in accordance with aspects of this disclosure.

The structured displays discussed herein can include one or both of the orientation graph 433 and heat map 414, 514, 614, 714, 814. FIG. 10 illustrates an embodiment of a structured display 610 which shows multiple first portions 412. Structured display 610 does not include an orientation graph 433 in order to accommodate the multiple heat maps 414 for multiple patients. The first portions 412 include the features shown, labeled, and described with reference to FIG. 6. Structured display 610 can advantageously allow caregivers to monitor the "heat maps" of multiple patients at once.

Figure 12:
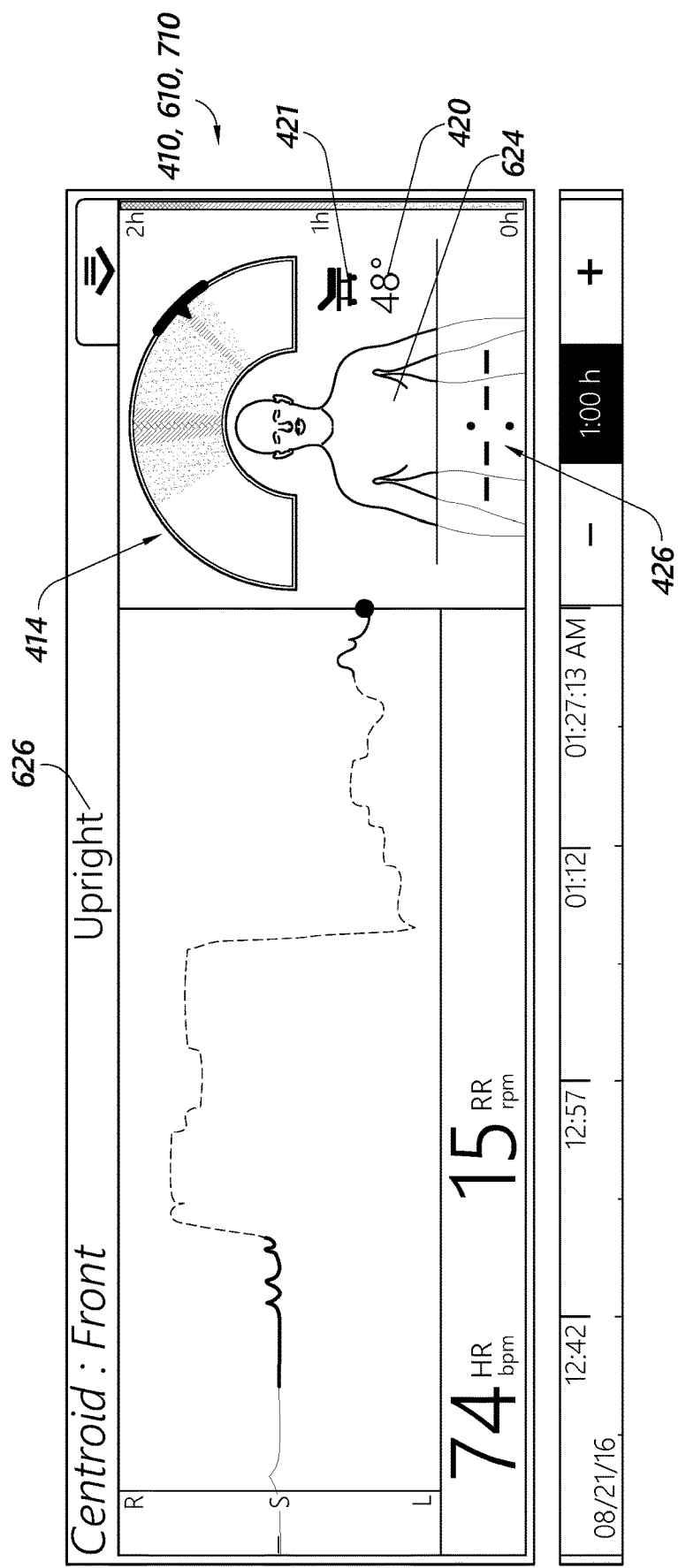
FIG. 12 illustrates an embodiment of a structured display on a display screen of patient monitor in accordance with aspects of this disclosure.

As discussed above, the structured display 410, 610, 710 can include a patient representation 424 to illustrate the position or orientation of a patient. FIG. 12 illustrates a patient presentation 624 generated by the one or more hardware processors in the structured display 410, 610, 710 when it is determined that the patient is in an upright position. Advantageously, patient representation 624 can quickly notify a monitoring caregiver that the patient is not laying in a hospital bed, but rather, is inclined with respect to the hospital bed. The structured display 410, 610, 710 can be configured to display patient representation 624 when the patient's body (e.g., upper body) is oriented at a threshold degree with respect to a horizontal plane and/or the hospital bed. This threshold degree can be for example, 70, 80, or 90 degrees. Techniques and/or systems for determining a patient's orientation are described in U.S. Patent Pub. No. 2017/0055896, which is incorporated by reference herein in its entirety. Structured display 410, 610, 710 can also be configured to display a notification 626 alerting a caregiver of the patient's change to an upright position. As shown in FIG. 12, timer 426 can be configured to display no time when the patient is in an upright position, which represents that the patient is not assuming one of the available orientations.

Figure 13:
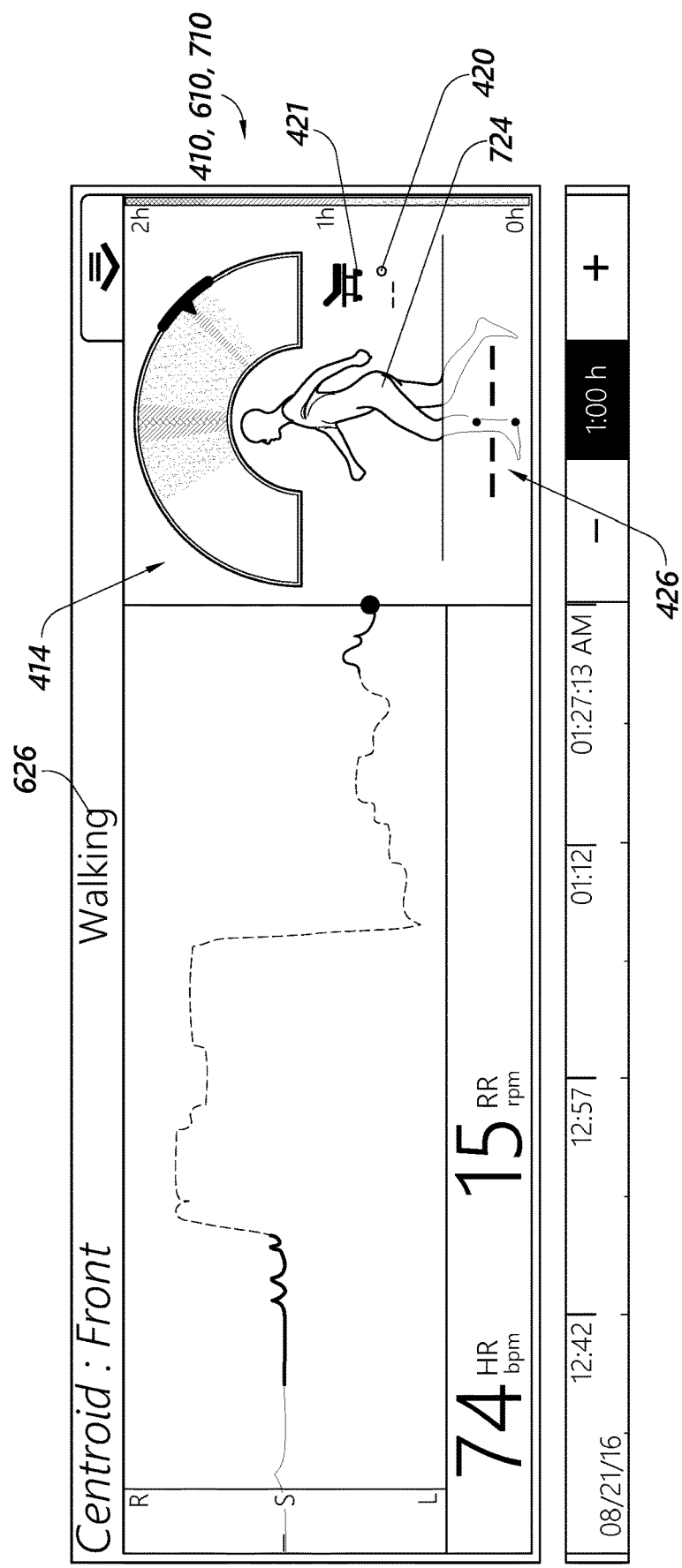
FIG. 13 illustrates an embodiment of a structured display on a display screen of patient monitor in accordance with aspects of this disclosure.

FIG. 13 illustrates a patient presentation 724 generated by the one or more hardware processors in the structured display 410, 610, 710 when it is determined that the patient is in a walking or running position. Advantageously, patient representation 724 can quickly notify a monitoring caregiver that the patient is not laying in a hospital bed, but rather, moving around in a manner which could be dangerous and/or life threatening. The structured display 410, 610, 710 can be configured to display patient representation 724 when sensor 102 and/or patient monitor 106 detects that the patient's acceleration is above a threshold value, for example. Techniques and/or systems for determining a patient's position and/or movement are described in U.S. Pat. No. 10,226,187 and U.S. Patent Pub. No. 2017/0055896, which are incorporated by reference herein in their entireties. Structured display 410, 610, 710 can also be configured to display a notification 626 alerting a caregiver of the patient's change to a walking or running position. As shown in FIG. 13, timer 426 can be—configured to display no time when the patient is in an upright position, which represents that the patient is not assuming one of the available orientations. Further, since the patient is not in the hospital bed when running or walking, the patient inclination degree indicator 420 can be configured to display no degree value.

Figure 14:
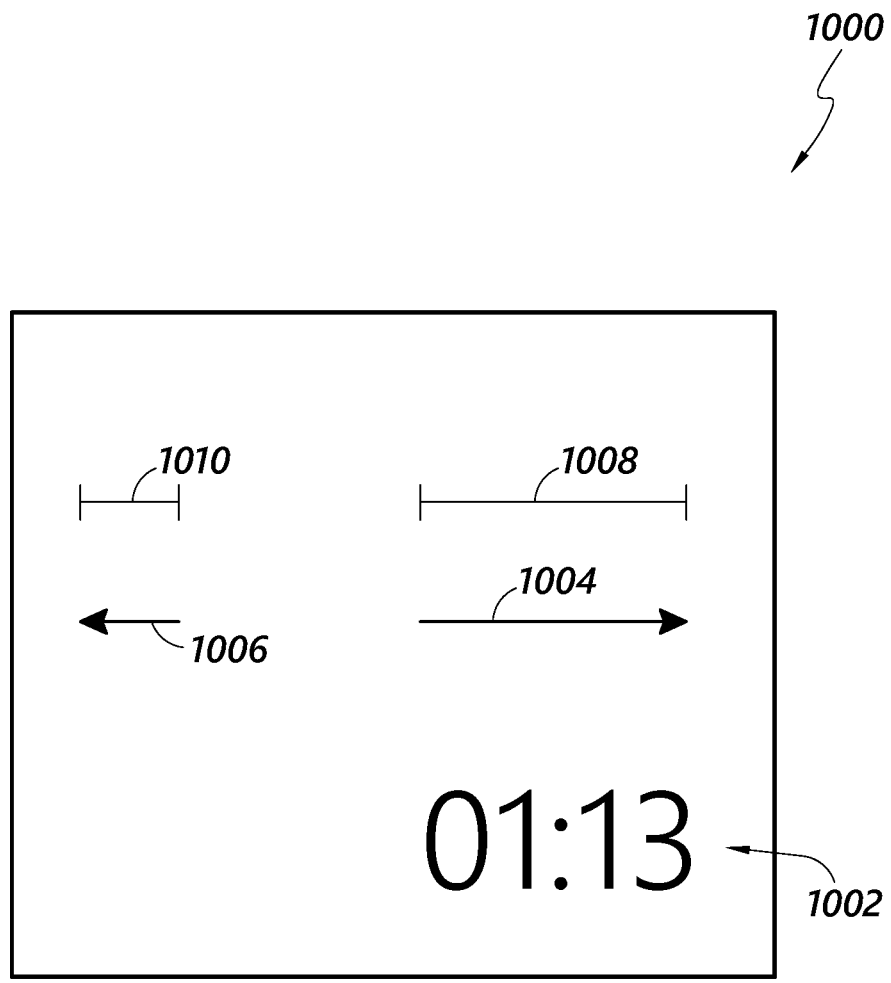
FIG. 14 illustrates an embodiment of a simplified display which can be generated on a patient monitor in accordance with aspects of this disclosure.

FIG. 14 illustrates a simplified display 1000 which can be generated on a patient monitor 106 to illustrate information regarding the patient's orientation to a caregiver. Simplified display 1000 can include a current orientation arrow 1004 which displays the current orientation of the patient. The direction and/or angle of arrow 1004 can vary depending on and/or association with a degree of orientation of the patient in a hospital bed, such as is discussed above. Simplified display 1000 can also include a previous orientation arrow 1006 which displays the previous orientation of the patient.

The direction and/or angle of arrow 1006 can vary depending on and/or association with a degree of orientation of the patient in a hospital bed, such as is discussed above. For example, the direction of arrow 1004 can indicate that the patient is currently in a right side orientation, and the direction of arrows 1006 can indicate that the patient was previously in a left side orientation. The length of arrows 1004, 1006 can vary depending on the length of time and/or accumulation of time the patient was in or is in the orientation. For example, as shown, arrow 1004 has a length 1008 that is longer than a length 1010 of arrow 1006, which can indicate that the length of time the patient has been in the current orientation is greater than the length of time that the patient was in the previous orientation, or it could represent that the accumulated time the patient has been in the current orientation is greater than the accumulated time that the patient was in the previous orientation. Simplified display 1000 can also include a timer 1002, which can be the same in some, many, or all respects as timer 426 described above.

Figure 15:
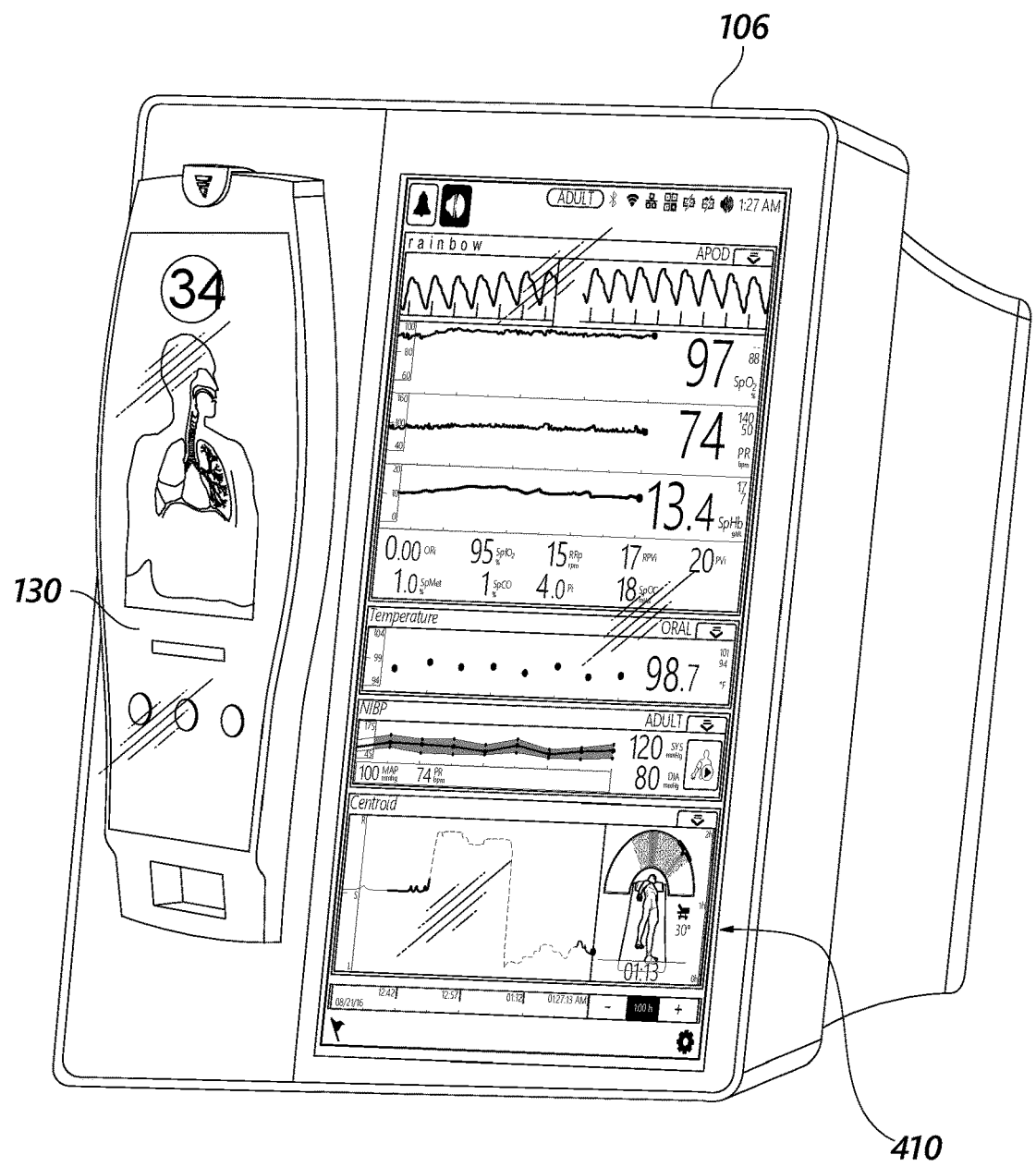
FIGS. 15-22 illustrate various embodiments of a display screen of a patient monitor having multiple display portions in accordance with aspects of this disclosure.
Figure 16:
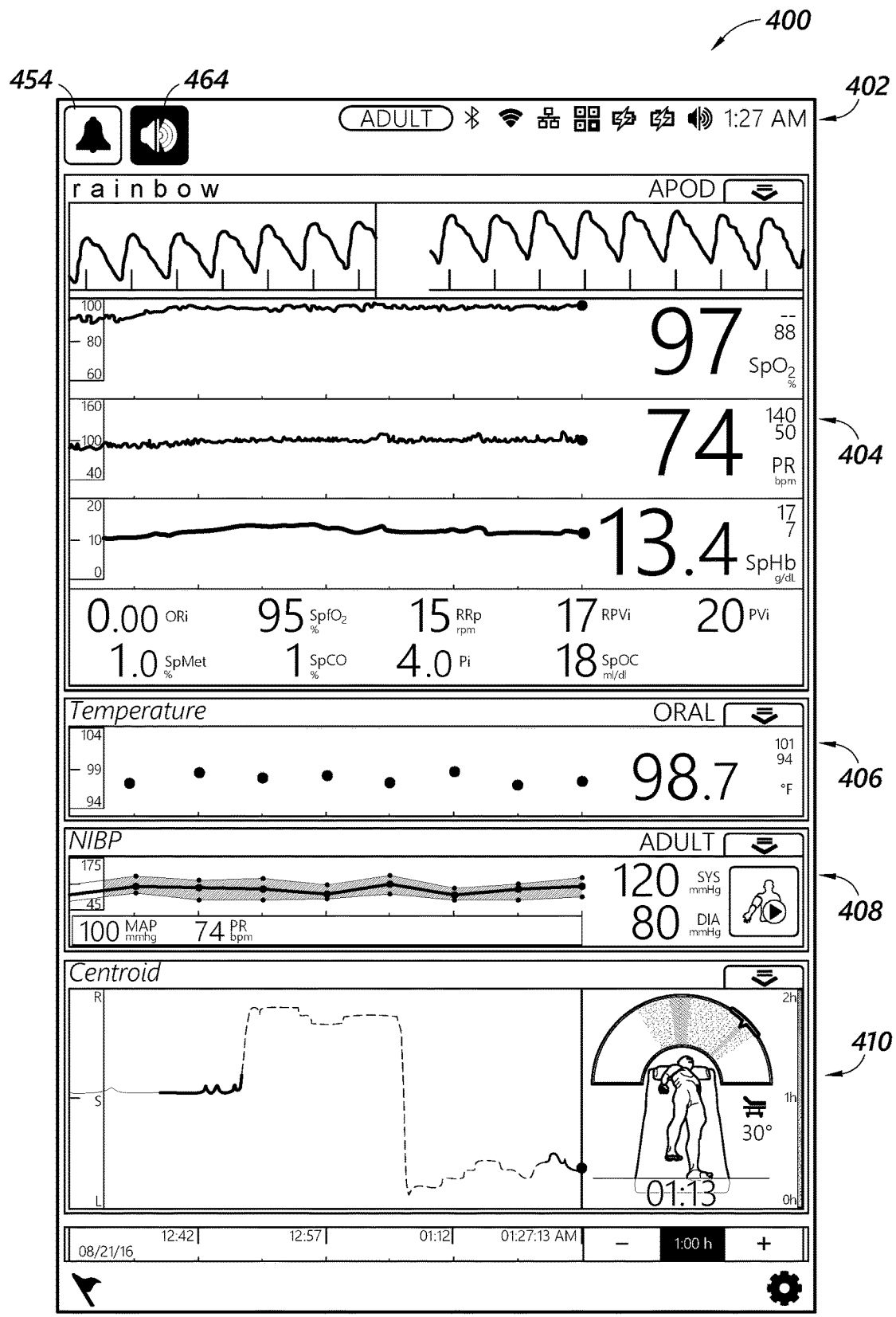

FIGS. 15-16 illustrate patient monitor 106 with a different configuration of a display screen 400, wherein the display screen 400 includes structured display 410 in addition to other display portions 402, 404, 406, and 408. FIGS. 15-16 thus illustrate what the structured display 410 of FIG. 6 looks like when combined with other display portions 402, 404, 406, and 408. Display portion 402 can include information relate to connectivity battery life, notifications and alerts, and/or other information. Display portion 404 can include information related to oxygen saturation, pulse rate, respiratory rate, among other physiological parameters. Display portion 406 can include information relate to a temperature of the patient. Display portion 408 can include information related to a non-invasive blood pressure of the patient.

Figure 17:
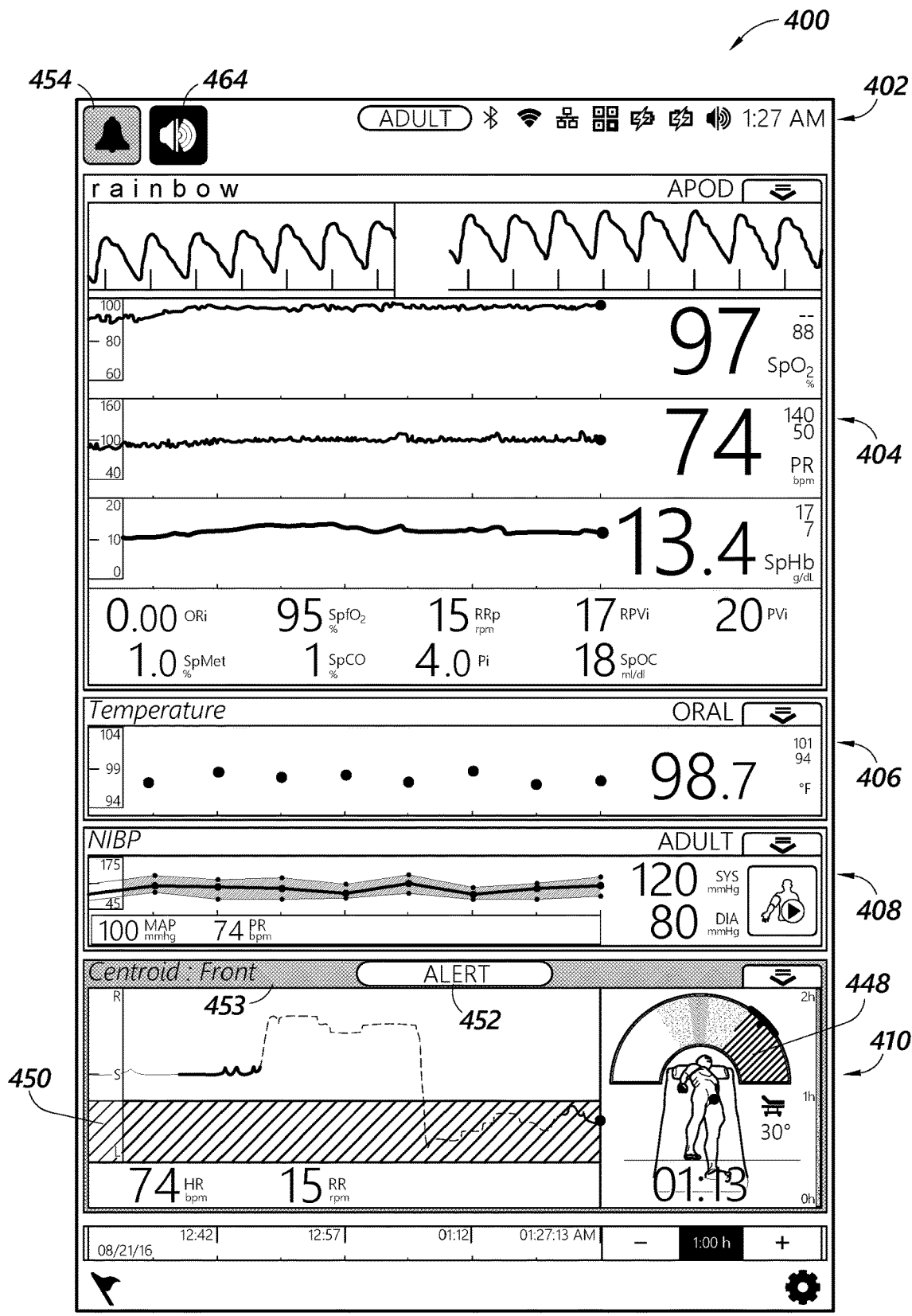
Figure 18:
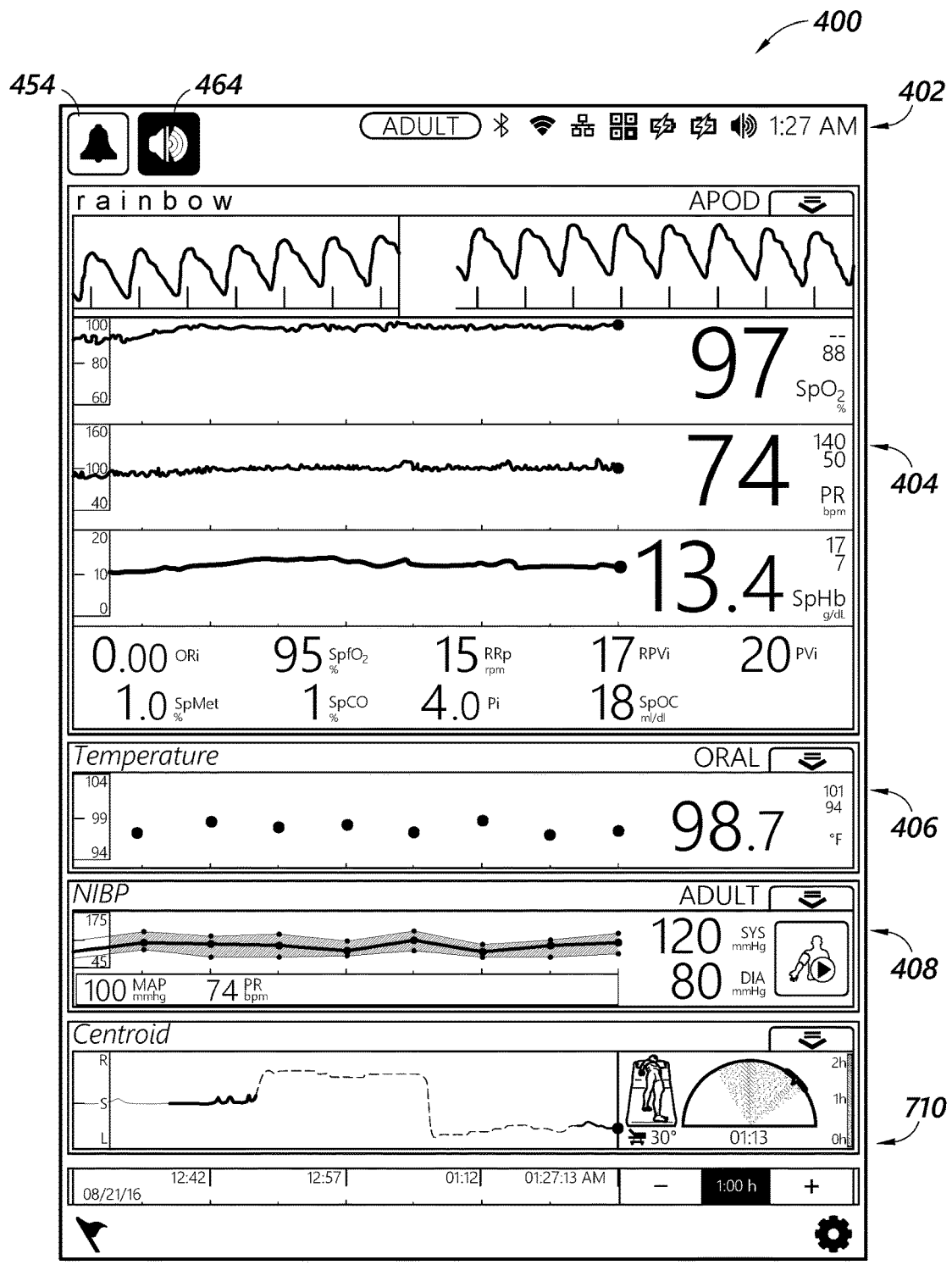
Figure 19:
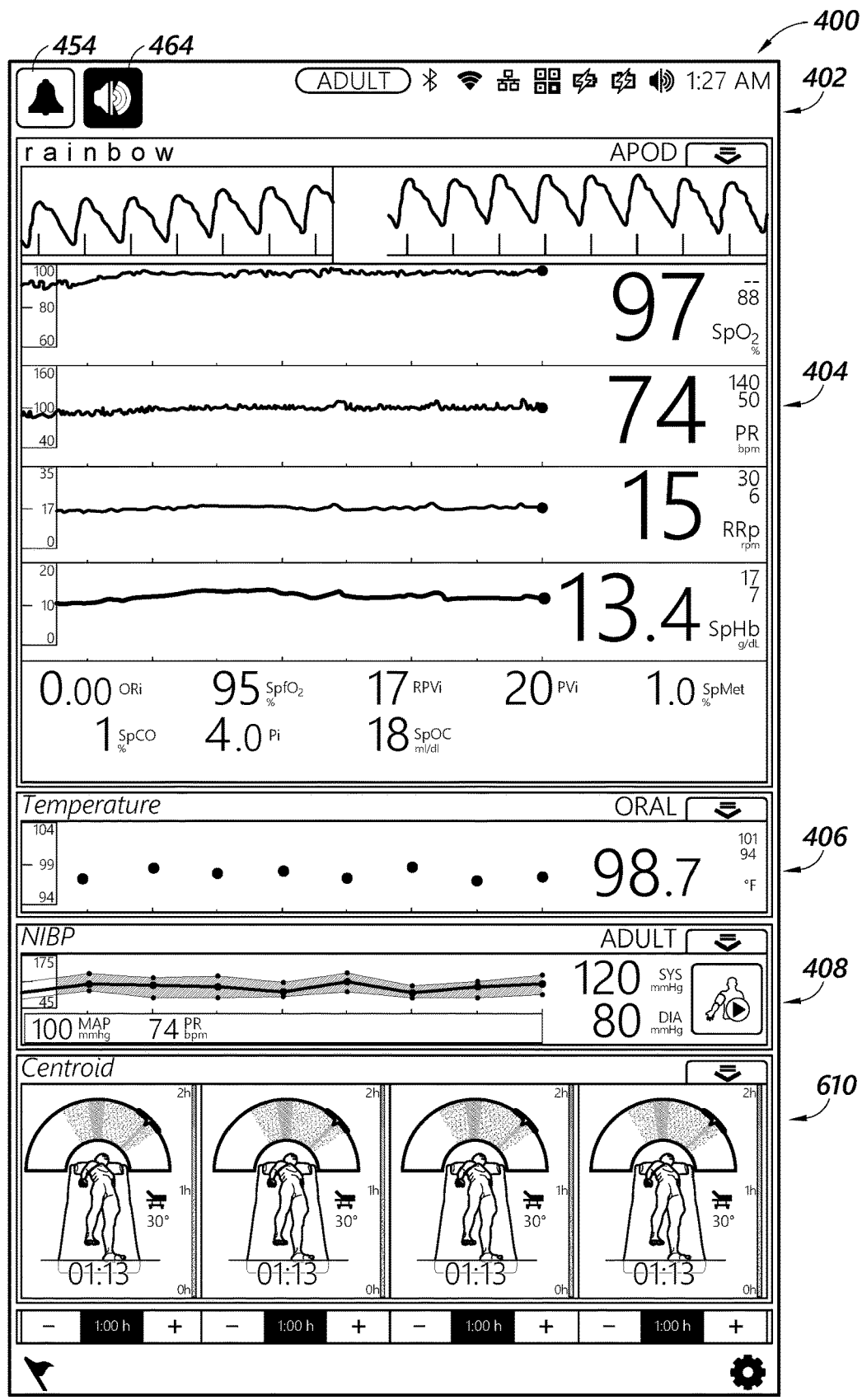
Figure 20:
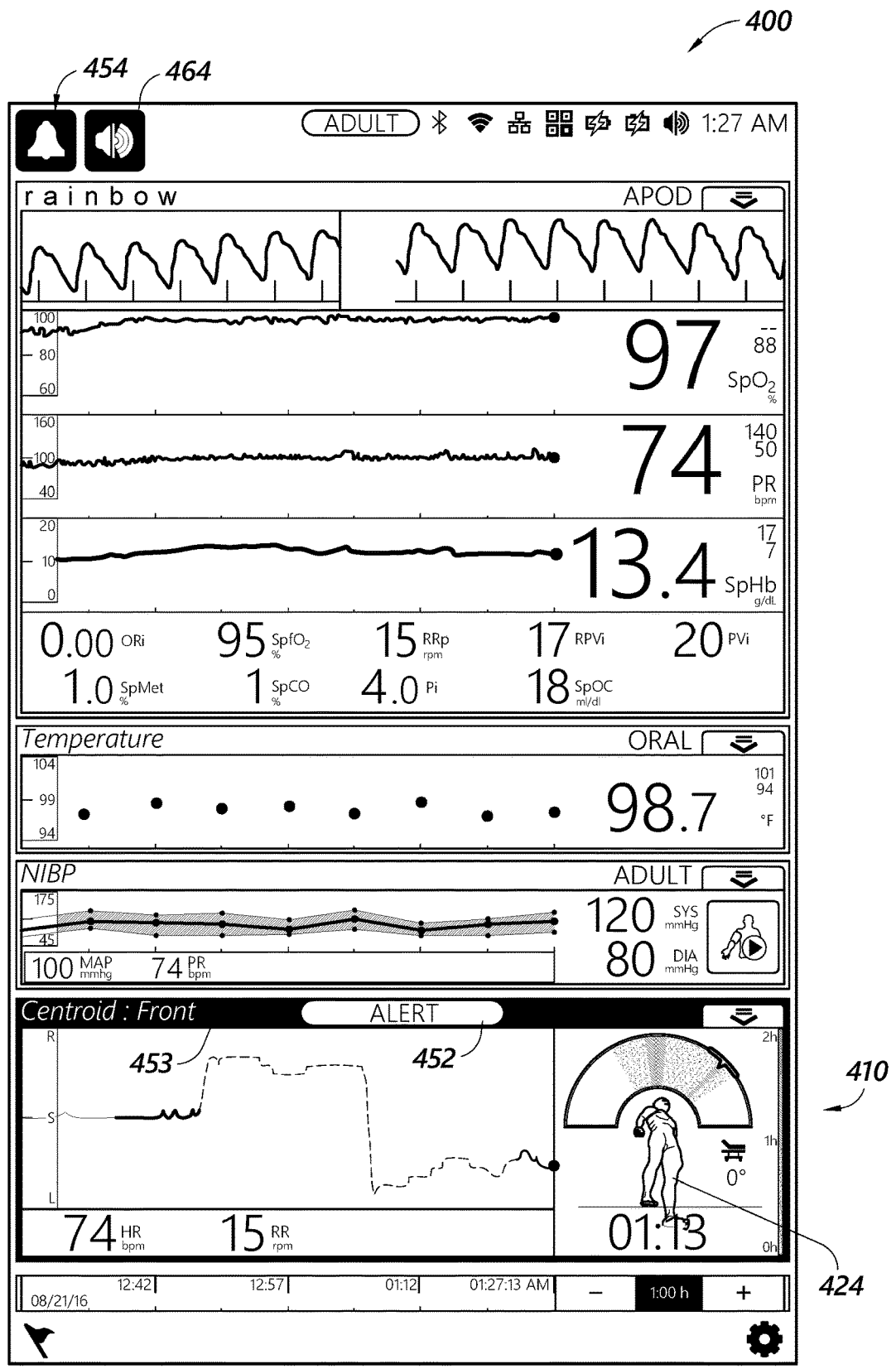
Figure 21:
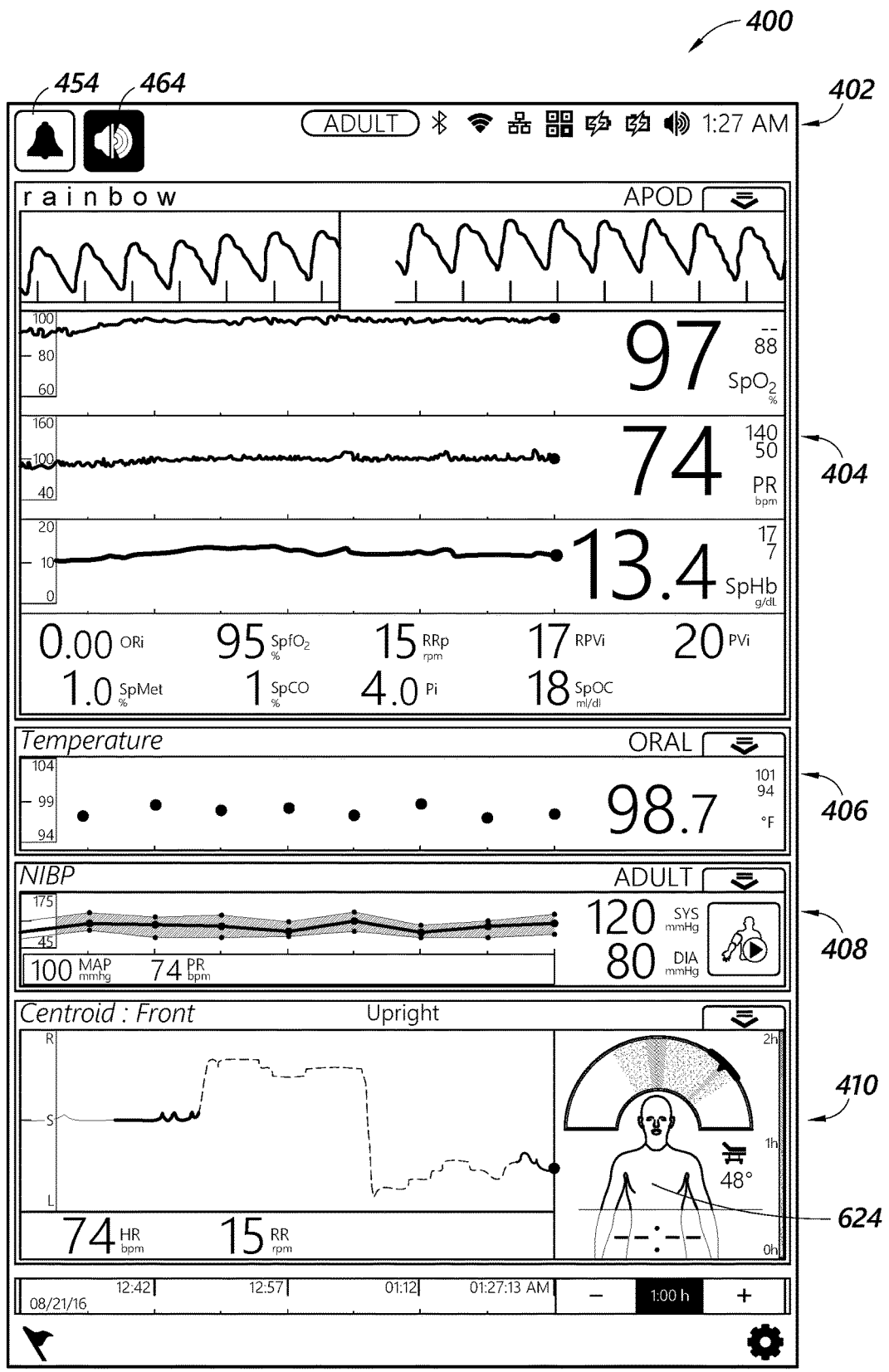
Figure 22:
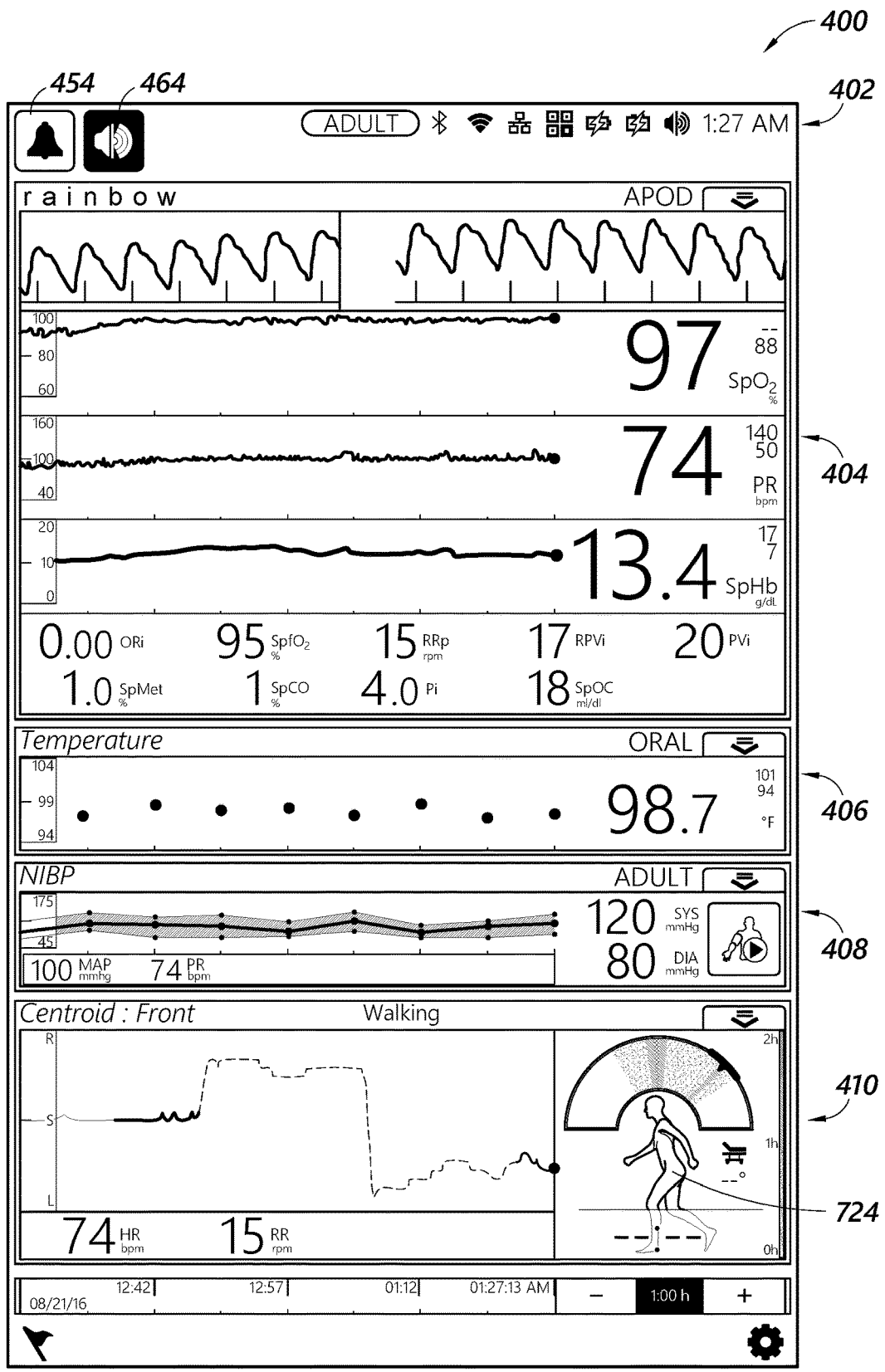

FIG. 17 illustrates what the structured display 410 of FIG. 7 looks like when combined with other display portions 402, 404, 406, and 408. FIG. 18 illustrates what the structured display 710 of FIG. 9A looks like when combined with other display portions 402, 404, 406, and 408. FIG. 19 illustrates what the structured display 610 of FIG. 10 looks like when combined with other display portions 402, 404, 406, and 408. FIG. 20 illustrates what the structured display 410, 610, 710 of FIG. 11 looks like when combined with other display portions 402, 404, 406, and 408. FIG. 20 illustrates what the structured display 410, 610, 710 of FIG. 11 looks like when combined with other display portions 402, 404, 406, and 408. FIG. 21 illustrates what the structured display 410, 610, 710 of FIG. 12 looks like when combined with other display portions 402, 404, 406, and 408. FIG. 22 illustrates what the structured display 410, 610, 710 of FIG. 13 looks like when combined with other display portions 402, 404, 406, and 408. The visual alert/icon 454 and audio alert/icon 464 can operate alone or in combination with the alerts described above.

Caregivers face increasing demands and pressures in modern healthcare settings. Consequentially, such caregivers can dedicate only a small fraction of their time to each individual patient. Furthermore, as technological advances in the medical field continue to be made, caregivers are tasked with employing an increasing number of physiological monitoring devices, each of which measure enormous amounts of physiological information and transmit such information to patient monitors for display. Such physiological information often continuously fluctuates and it is often impossible, or at least extraordinarily difficult, for a caregiver to monitor, let alone react to, such information. As a result, caregivers are often unable to prevent or satisfactorily treat a number of medical conditions, such as pressure ulcers. As discussed above with respect to pressure ulcer formation, it is incredibly difficult for caregivers to quickly obtain information regarding a patient's orientation at any given time, let alone evaluate such information and determine if the patient's orientation needs to be adjusted. Given that patient orientation is just one of a significant number of patient physiological parameters that caregivers continuously monitor via patient monitors that have limited visual real estate, improvements in displaying orientation-related information via user interfaces are desperately needed so that caregivers can properly care for, and treat, their patients.

The disclosed structured displays and components thereof provide notable improvements to the current state of patient monitoring, especially with respect to monitoring a patient's orientation. The disclosed structured displays and components thereof also provide practical solutions to technical problems associated with displaying a large amount of patient physiological information on graphical user interfaces of patient monitoring devices. More specifically, the disclosed structured displays and components thereof can display a significant amount of orientation-related information while taking up only minimal visual real estate on a display and/or user interface of a patient monitor. Further, the structured displays and components thereof disclosed herein can present such orientation-related information in an efficient and easily "digestible" manner so as to enable caregivers to quickly assess and treat patients at risk of developing, or suffering from, pressure ulcers. For example, the disclosed heat maps 414, 514, 614, 714, 814 and/or orientation graph 433, alone or in combination with the disclosed patient representation 424, can provide a caregiver with a holistic sense of a patient's recent orientation history and/or current orientation in a matter of seconds. At the same time, as discussed and shown herein, such components (and others discussed herein) can be organized and/or configured as part of a structured display which takes up minimal space on a user interface of a display screen. As discussed, such minimal utilization of visual real estate can be critical where the user interface and/or display screen is small (for example, handheld devices or mobile phones) or where the user interface is cluttered with a significant number of displays related to other physiological parameters (for example, see FIGS. 15-22).

ADDITIONAL CONSIDERATIONS

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by one or more hardware processors, such as microprocessor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. Hardware processors can include electrical circuitry configured to process computer-executable instructions. In another embodiment, a hardware processor includes an FPGA or other programmable device that performs logic operations without processing computer-executable instructions. A hardware processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the hardware processor such that the hardware processor can read information from, and write information to, the storage medium. In the alternative, the storage medium can be integral to the hardware processor. The storage medium can be volatile or nonvolatile.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or methods illustrated can be made without departing from the spirit of the disclosure. As will be recognized, certain embodiments described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses, systems, and/or methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

What is claimed is:

1. A system for monitoring an orientation of a patient, the system comprising:
one or more hardware processors configured to:
receive one or more signals from a sensor attached to the patient;
process said one or more signals to determine the patient's orientation;
generate a graphic for display on a display of a patient monitor, the graphic comprising a plurality of lines, each line of the plurality of lines being associated with an orientation of a plurality of orientations assumable by the patient, each line of the plurality of lines having a same thickness, wherein the plurality of lines are uniformly spaced within the graphic at fixed positions relative to each other to spatially correspond to the orientations of the plurality of orientations, wherein one of said plurality of lines is associated with a supine orientation of the plurality of orientations and is positioned in a middle of the plurality of lines extending vertically from a bottom of the graphic to a top of the graphic; and
modify an appearance of the plurality of lines based upon an amount of time the patient has been oriented in respective orientations of the plurality of orientations.

2. The system of claim 1, wherein the one or more hardware processors are further configured to generate a 3D representation of a model body corresponding to the patient for display adjacent to the graphic.

3. The system of claim 1, wherein the one or more hardware processors are further configured to:
cause the plurality of lines to have a first color in response to determining that the patient has been oriented in an orientation associated with the plurality of lines for less than a first threshold; and
cause the plurality of lines to have a second color in response to determining that the patient has been oriented in an orientation associated with the plurality of lines for less than a second threshold and for more than the first threshold; and
cause the plurality of lines to have a first color in response to determining that the patient has been oriented in an orientation associated with the plurality of lines for more than the second threshold.

4. The system of claim 1, wherein the one or more hardware processors are further configured to generate an alert in response to determining that the patient has been oriented in an orientation for more than a threshold.

5. The system of claim 1, wherein the graphic further comprises a border, wherein the border comprises a first edge, a second edge opposite the first edge, a third edge, and a fourth edge opposite the third edge, each of the third and fourth edges connected to the first and second edges, and wherein said plurality of lines extend between the first and second edges.

6. The system of claim 1, wherein the one or more hardware processors are further configured to generate an indicator for display located adjacent to the graphic and configured to indicate a current orientation of the patient, wherein the one or more hardware processors are further configured to move the indicator as the current orientation of the patient changes.

7. The system of claim 1, wherein the sensor includes at least one or more of an accelerometer or gyroscope.

8. The system of claim 1, wherein the one or more hardware processors are further configured to generate for display a hatched pattern within the graphic, the hatched pattern representing an un-allowed patient orientation.

9. The system of claim 8, wherein the one or more hardware processors are further configured to generate an alert in response to determining that an orientation of the patient corresponds to the un-allowed patient orientation.

10. The system of claim 8, wherein the un-allowed patient orientation is pre-determined by a caregiver.

11. A computing system comprising:
a computer readable storage medium having program instructions embodied therewith; and
one or more processors configured to execute the program instructions to cause the computing system to:
receive one or more signals from a sensor attached to a patient;
process said one or more signals to determine the patient's orientation;
generate user interface data for rendering an interactive graphical user interface, the user interface comprising a graphic comprising a plurality of lines, each line of the plurality of lines being associated with an orientation of a plurality of orientations, each line of the plurality of lines having a same thickness, wherein the plurality of lines are uniformly spaced within the graphic at fixed positions relative to each other to spatially correspond to the orientations of the plurality of orientations, wherein one of said plurality of lines is associated with a supine orientation of the plurality of orientations and is positioned in a middle of the plurality of lines extending vertically between a bottom of the graphic and a top of the graphic; and
modify an appearance of the plurality of lines based upon an amount of time the patient has been oriented in respective orientations of the plurality of orientations.

12. The computing system of claim 11, wherein the user interface further comprises an indicator located adjacent to the graphic and configured to indicate a current orientation of the patient, wherein the one or more hardware processors are further configured to move the indicator as the current orientation of the patient changes.

13. The computing system of claim 11, wherein the user interface further comprises a 3D representation of a model body to the patient for display adjacent to the graphic.

14. The computing system of claim 11, wherein the one or more hardware processors are further configured to:
display a hatched pattern within the graphic, the hatched pattern representing an un-allowed patient orientation; and
generate an alert in response to determining that an orientation of the patient corresponds to the un-allowed patient orientation.

15. The computing system of claim 14, wherein the un-allowed patient orientation is pre-determined by a caregiver.

16. A computer-implemented method comprising:
receiving one or more signals from a sensor attached to a patient;
processing said one or more signals to determine the patient's orientation;
generating user interface data for rendering an interactive graphical user interface, the user interface comprising a graphic comprising a plurality of lines, each line of the plurality of lines being associated with an orientation of a plurality of orientations assumable by the patient, each line of the plurality of lines having a same thickness, wherein the plurality of lines are uniformly spaced within the graphic at fixed positions relative to each other to spatially correspond to the orientations of the plurality of orientations, wherein one of said plurality of lines is associated with a supine orientation of the plurality of orientations and is positioned in a middle of the plurality of lines extending vertically from a bottom of the graphic to a top of the graphic; and
modifying an appearance of the plurality of lines based upon an amount of time the patient has been oriented in respective orientations of the plurality of orientations.

17. The method of claim 16, wherein the user interface further comprises an indicator located adjacent to the graphic and configured to indicate a current orientation of the patient.

18. The method of claim 16, wherein the one or more hardware processors are further configured to generate a 3D representation of a model body to the patient for display adjacent to the graphic.

19. The method of claim 16, wherein the graphic further includes a hatched pattern representing an un-allowed patient orientation, the method further comprising generating an alert in response to determining that an orientation of the patient corresponds to the un-allowed patient orientation.

20. The method of claim 19, wherein the un-allowed patient orientation is pre-determined by a caregiver.

* * * * *